US 12,403,190 B2

(12) United States Patent
Gill

(10) Patent No.: US 12,403,190 B2
(45) Date of Patent: Sep. 2, 2025

(54) CORONAVIRUS VACCINE AND METHODS OF USE THEREOF

(71) Applicant: Davinder Gill, Andover, MA (US)

(72) Inventor: Davinder Gill, Andover, MA (US)

( * ) Notice: Subject to any disclaimer, the term of this patent is extended or adjusted under 35 U.S.C. 154(b) by 1105 days.

(21) Appl. No.: 17/341,928

(22) Filed: Jun. 8, 2021

(65) Prior Publication Data

US 2021/0393769 A1 Dec. 23, 2021

Related U.S. Application Data

(60) Provisional application No. 63/037,367, filed on Jun. 10, 2020.

(51) Int. Cl.
A61K 39/215 (2006.01)
A61P 31/14 (2006.01)
C12N 7/00 (2006.01)
A61K 39/00 (2006.01)

(52) U.S. Cl.
CPC ............ A61K 39/215 (2013.01); A61P 31/14 (2018.01); C12N 7/00 (2013.01); A61K 2039/5258 (2013.01); C12N 2730/10123 (2013.01); C12N 2730/10134 (2013.01); C12N 2770/20023 (2013.01); C12N 2770/20034 (2013.01)

(58) Field of Classification Search
None
See application file for complete search history.

(56) References Cited

U.S. PATENT DOCUMENTS

| | | | |
|---|---|---|---|
| 2005/0130127 A1* | 6/2005 | Rottier | A61P 31/00 435/235.1 |
| 2006/0257852 A1* | 11/2006 | Rappuoli | A61K 39/215 435/69.3 |
| 2008/0171062 A1* | 7/2008 | Sala-Schaeffer | A61K 39/12 435/254.2 |

OTHER PUBLICATIONS

Issued_Patents_AA database sequence alignment of instant SEQ ID No. 151 with SEQ ID No. 125 in U.S. Pat. No. 10,973,909 Apr.-Jul. 2020.*
Issued_Patents_AA database sequence alignment of instant SEQ ID No. 153 with SEQ ID No. 125 in U.S. Pat. No. 10,973,909 Apr.-Jul. 2020.*
Marini et al. (Frontiers in immunology. Dec. 12, 2019;10:2931).*
Ling et al. (Peptides. May 2020; 170328).*
Creative Biolabs: sars-cov-2.creative-biolabs.com, May 5, 2020.
CORDIS:cordis.europa.edu/project/id/101003608 Apr. 1, 2020.
Contact Pharma website: contractpharma.com/contents/view_breaking-news/2020-04-27.
Swann et al: "Minimal system for assembly of SARS-CoV-2 virus like particles". BioRxiv, doi.org/10.1101/2020.06.06.128058.

(Continued)

*Primary Examiner* — Shanon A. Foley
(74) *Attorney, Agent, or Firm* — WCF IP

(57) ABSTRACT

An immunogenic composition effective for eliciting an immune response against cells that present coronavirus S protein and/or coronavirus M protein derived antigens on a virus-like-particle (VLP) system. In a method embodiment, the antigen presenting VLP is administered to a mammal, such as a human, to elicit an immune response against coronavirus S protein and/or coronavirus M protein. A preferred method embodiment may include at least one additional dose of immunogenic composition to enhance the immune response effectiveness of the coronavirus vaccine.

3 Claims, 5 Drawing Sheets

Specification includes a Sequence Listing.

(56) References Cited

OTHER PUBLICATIONS

Xia et al: "Inhibition of SARS-CoV-2 (previously 2019-nCoV) infection by a highly potent pan-coronavirus fusion inhibitor targeting Its spike protein that harbors a high capacity to mediate membrane fusion", Cell Research, vol. 30 pp. 343-355, 2020-03-30.
Lip et al: "Inhibition of SARS-CoV-2 (previously 2019-nCoV) infection by a highly potent pan-coronavirus fusion inhibitor targeting its spike protein that harbors a high capacity to mediate membrane fusion", Journal of Virology, vol. 80 pp. 941-950, Jan. 2006.

* cited by examiner

| Domain | Variant residues |
|---|---|
| NTD | Phe32, Ser50, Thr76, Gln218 |
| RBD | Arg346, Ala372, Arg403, Asn439, Asn440, Leu441, Ser443, Val445, Tyr449, Ser459, Thr478, Val483, Glu484, Phe486, Phe490, Gln493, Ser494, Gln498, Asn501, Tyr505, His619 |
| SD1 | Glu324 |
| SD2 | Thr604 |
| S1/S2 | 682-PRRA-685 (insertion) |
| S2 | Asn1125, Val1228 |

FIG.3A
FIG.3B
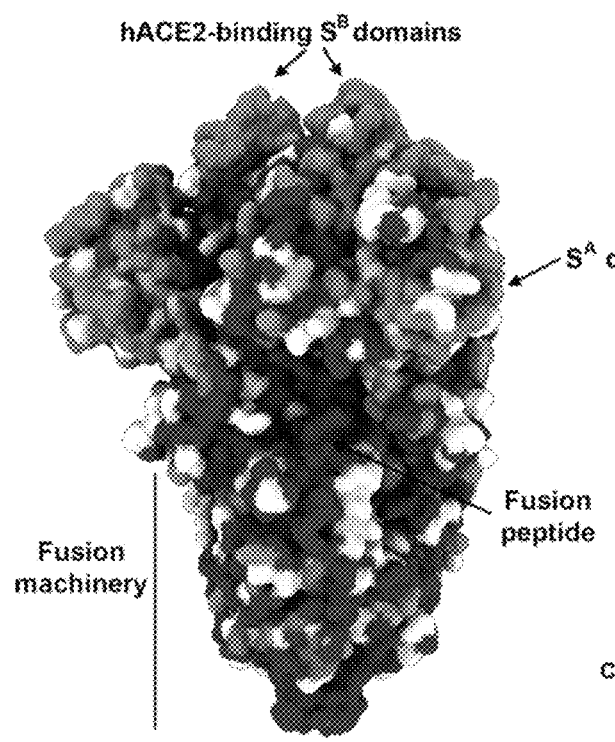
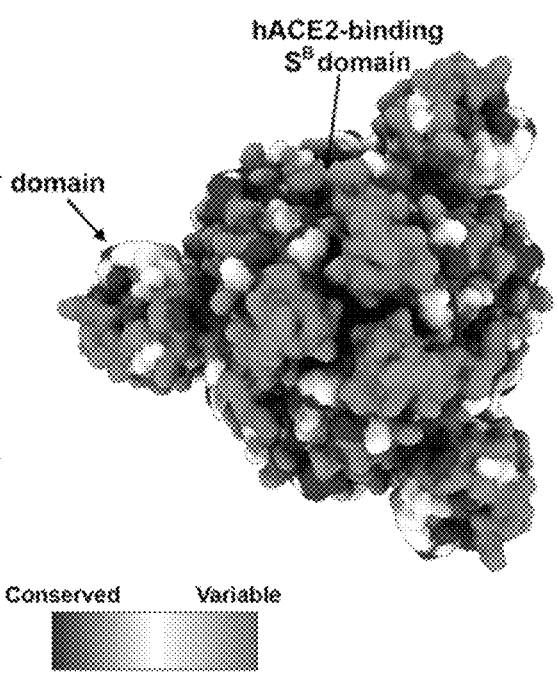

```
                        SEQUENCE LISTING

<160> NUMBER OF SEQ ID NOS: 168

<210> SEQ ID NO 1
<211> LENGTH: 15
<212> TYPE: PRT
<213> ORGANISM: Artificial Sequence
<220> FEATURE:
<223> OTHER INFORMATION: Synthetic: 41014

<400> SEQUENCE: 1

Met Ala Asp Asn Gly Thr Ile Thr Val Glu Glu Leu Lys Gln Leu
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic: 41015

<400> SEQUENCE: 2

Met Ala Asp Asn Gly Thr Ile Thr Val Glu Glu Leu Lys Gln Leu Leu
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: Synthetic: 41016

<400> SEQUENCE: 3

Met Ala Asp Asn Gly Thr Ile Thr Val Glu Glu Leu Lys Gln Leu Leu
1               5                   10                  15

Glu Gln

<210> SEQ ID NO 4
<211> LENGTH: 20
<212> TYPE: PRT
<213> ORGANISM: Artificial Sequence
<220> FEATURE:
<223> OTHER INFORMATION: Synthetic: 41017

<400> SEQUENCE: 4

Met Ala Asp Asn Gly Thr Ile Thr Val Glu Glu Leu Lys Gln Leu Leu
1               5                   10                  15

Glu Gln Trp Asn
            20

<210> SEQ ID NO 5
<211> LENGTH: 31
<212> TYPE: PRT
<213> ORGANISM: Artificial Sequence
<220> FEATURE:
<223> OTHER INFORMATION: Synthetic: 41018
```

<400> SEQUENCE: 5

Met Ala Asp Asn Gly Thr Ile Thr Val Glu Glu Leu Lys Gln Leu Leu
1               5                   10                  15

Glu Gln Trp Asn Leu Val Ile Gly Phe Leu Phe Leu Ala Trp Ile
            20                  25                  30

<210> SEQ ID NO 6
<211> LENGTH: 8
<212> TYPE: PRT
<213> ORGANISM: Artificial Sequence
<220> FEATURE:
<223> OTHER INFORMATION: Synthetic: 29128

<400> SEQUENCE: 6

Ile Thr Val Glu Glu Leu Lys Gln
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic: 29129

<400> SEQUENCE: 7

Ile Thr Val Glu Glu Leu Lys Gln Leu Leu Glu Gln Trp Asn Leu Val
1               5                   10                  15

Ile

<210> SEQ ID NO 8
<211> LENGTH: 18
<212> TYPE: PRT
<213> ORGANISM: Artificial Sequence
<220> FEATURE:
<223> OTHER INFORMATION: Synthetic: 32059

<400> SEQUENCE: 8

Lys Leu Asn Thr Asp His Ala Gly Ser Asn Asp Asn Ile Ala Leu Leu
1               5                   10                  15

Val Gln

<210> SEQ ID NO 9
<211> LENGTH: 15
<212> TYPE: PRT
<213> ORGANISM: Artificial Sequence
<220> FEATURE:
<223> OTHER INFORMATION: Synthetic: 63165

<400> SEQUENCE: 9

Thr Asp His Ala Gly Ser Asn Asp Asn Ile Ala Leu Leu Val Gln
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: Synthetic: 12417

<400> SEQUENCE: 10

Glu Ile Asp Lys Gly Ile Tyr Gln Thr Ser Asn Phe Arg Val Val Pro
1               5                   10                  15

Ser

```
<210> SEQ ID NO 11
<211> LENGTH: 20
<212> TYPE: PRT
<213> ORGANISM: Artificial Sequence
<220> FEATURE:
<223> OTHER INFORMATION: Synthetic: 30988

<400> SEQUENCE: 11

Lys Gly Ile Tyr Gln Thr Ser Asn Phe Arg Val Val Pro Ser Gly Asp
1               5                   10                  15

Val Val Arg Phe
            20

<210> SEQ ID NO 12
<211> LENGTH: 8
<212> TYPE: PRT
<213> ORGANISM: Artificial Sequence
<220> FEATURE:
<223> OTHER INFORMATION: Synthetic: 30987

<400> SEQUENCE: 12

Lys Gly Ile Tyr Gln Thr Ser Asn
1               5

<210> SEQ ID NO 13
<211> LENGTH: 18
<212> TYPE: PRT
<213> ORGANISM: Artificial Sequence
<220> FEATURE:
<223> OTHER INFORMATION: Synthetic: 29666

<400> SEQUENCE: 13

Ile Tyr Gln Thr Ser Asn Phe Arg Val Val Pro Ser Gly Asp Val Val
1               5                   10                  15

Arg Phe

<210> SEQ ID NO 14
<211> LENGTH: 17
<212> TYPE: PRT
<213> ORGANISM: Artificial Sequence
<220> FEATURE:
<223> OTHER INFORMATION: Synthetic: 66337

<400> SEQUENCE: 14

Thr Ser Asn Phe Arg Val Val Pro Ser Gly Asp Val Val Arg Phe Pro
1               5                   10                  15

Asn

<210> SEQ ID NO 15
<211> LENGTH: 17
<212> TYPE: PRT
<213> ORGANISM: Artificial Sequence
<220> FEATURE:
<223> OTHER INFORMATION: Synthetic: 58001

<400> SEQUENCE: 15

Ser Gly Asp Val Val Arg Phe Pro Asn Ile Thr Asn Leu Cys Pro Phe
1               5                   10                  15

Gly

<210> SEQ ID NO 16
<211> LENGTH: 17
<212> TYPE: PRT
<213> ORGANISM: Artificial Sequence
```

<220> FEATURE:
<223> OTHER INFORMATION: Synthetic: 70719

<400> SEQUENCE: 16

Val Arg Phe Pro Asn Ile Thr Asn Leu Cys Pro Phe Gly Glu Val Phe
1               5                   10                  15

Asn

<210> SEQ ID NO 17
<211> LENGTH: 17
<212> TYPE: PRT
<213> ORGANISM: Artificial Sequence
<220> FEATURE:
<223> OTHER INFORMATION: Synthetic: 35083

<400> SEQUENCE: 17

Leu Cys Pro Phe Gly Glu Val Phe Asn Ala Thr Lys Phe Pro Ser Val
1               5                   10                  15

Tyr

<210> SEQ ID NO 18
<211> LENGTH: 8
<212> TYPE: PRT
<213> ORGANISM: Artificial Sequence
<220> FEATURE:
<223> OTHER INFORMATION: Synthetic: 15972

<400> SEQUENCE: 18

Phe Gly Glu Val Phe Asn Ala Thr
1               5

<210> SEQ ID NO 19
<211> LENGTH: 17
<212> TYPE: PRT
<213> ORGANISM: Artificial Sequence
<220> FEATURE:
<223> OTHER INFORMATION: Synthetic: 17132

<400> SEQUENCE: 19

Phe Asn Ala Thr Lys Phe Pro Ser Val Tyr Ala Trp Glu Arg Lys Lys
1               5                   10                  15

Ile

<210> SEQ ID NO 20
<211> LENGTH: 20
<212> TYPE: PRT
<213> ORGANISM: Artificial Sequence
<220> FEATURE:
<223> OTHER INFORMATION: Synthetic: 64563

<400> SEQUENCE: 20

Thr Lys Phe Pro Ser Val Tyr Ala Trp Glu Arg Lys Lys Ile Ser Asn
1               5                   10                  15

Cys Val Ala Asp
            20

<210> SEQ ID NO 21
<211> LENGTH: 17
<212> TYPE: PRT
<213> ORGANISM: Artificial Sequence
<220> FEATURE:
<223> OTHER INFORMATION: Synthetic: 49557

<400> SEQUENCE: 21

Pro Ser Val Tyr Ala Trp Glu Arg Lys Lys Ile Ser Asn Cys Val Ala
1               5                   10                  15

Asp

<210> SEQ ID NO 22
<211> LENGTH: 17
<212> TYPE: PRT
<213> ORGANISM: Artificial Sequence
<220> FEATURE:
<223> OTHER INFORMATION: Synthetic: 62403

<400> SEQUENCE: 22

Ser Val Tyr Ala Trp Glu Arg Lys Lys Ile Ser Asn Cys Val Ala Asp
1               5                   10                  15

Tyr

<210> SEQ ID NO 23
<211> LENGTH: 24
<212> TYPE: PRT
<213> ORGANISM: Artificial Sequence
<220> FEATURE:
<223> OTHER INFORMATION: Synthetic: 118676

<400> SEQUENCE: 23

Val Tyr Ala Trp Glu Arg Lys Lys Ile Ser Asn Cys Val Ala Asp Tyr
1               5                   10                  15

Ser Val Leu Tyr Asn Ser Thr Phe
            20

<210> SEQ ID NO 24
<211> LENGTH: 18
<212> TYPE: PRT
<213> ORGANISM: Artificial Sequence
<220> FEATURE:
<223> OTHER INFORMATION: Synthetic: 31582

<400> SEQUENCE: 24

Lys Lys Ile Ser Asn Cys Val Ala Asp Tyr Ser Val Leu Tyr Asn Ser
1               5                   10                  15

Thr Phe

<210> SEQ ID NO 25
<211> LENGTH: 17
<212> TYPE: PRT
<213> ORGANISM: Artificial Sequence
<220> FEATURE:
<223> OTHER INFORMATION: Synthetic: 31581

<400> SEQUENCE: 25

Lys Lys Ile Ser Asn Cys Val Ala Asp Tyr Ser Val Leu Tyr Asn Ser
1               5                   10                  15

Thr

<210> SEQ ID NO 26
<211> LENGTH: 9
<212> TYPE: PRT
<213> ORGANISM: Artificial Sequence
<220> FEATURE:
<223> OTHER INFORMATION: Synthetic: 7247

<400> SEQUENCE: 26

Cys Val Ala Asp Tyr Ser Val Leu Tyr
1               5

```
<210> SEQ ID NO 27
<211> LENGTH: 17
<212> TYPE: PRT
<213> ORGANISM: Artificial Sequence
<220> FEATURE:
<223> OTHER INFORMATION: Synthetic: 75920

<400> SEQUENCE: 27

Tyr Ser Val Leu Tyr Asn Ser Thr Phe Phe Ser Thr Phe Lys Cys Tyr
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: Synthetic: 61598

<400> SEQUENCE: 28

Ser Thr Phe Phe Ser Thr Phe Lys Cys Tyr Gly Val Ser Ala Thr Lys
1               5                   10                  15

Leu

<210> SEQ ID NO 29
<211> LENGTH: 17
<212> TYPE: PRT
<213> ORGANISM: Artificial Sequence
<220> FEATURE:
<223> OTHER INFORMATION: Synthetic: 15903

<400> SEQUENCE: 29

Phe Phe Ser Thr Phe Lys Cys Tyr Gly Val Ser Ala Thr Lys Leu Asn
1               5                   10                  15

Asp

<210> SEQ ID NO 30
<211> LENGTH: 10
<212> TYPE: PRT
<213> ORGANISM: Artificial Sequence
<220> FEATURE:
<223> OTHER INFORMATION: Synthetic: 30098

<400> SEQUENCE: 30

Lys Cys Tyr Gly Val Ser Ala Thr Lys Leu
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Synthetic: 7382

<400> SEQUENCE: 31

Cys Tyr Gly Val Ser Ala Thr Lys Leu
1               5

<210> SEQ ID NO 32
<211> LENGTH: 17
<212> TYPE: PRT
<213> ORGANISM: Artificial Sequence
<220> FEATURE:
<223> OTHER INFORMATION: Synthetic: 7383
```

```
<400> SEQUENCE: 32

Cys Tyr Gly Val Ser Ala Thr Lys Leu Asn Asp Leu Cys Phe Ser Asn
1               5                   10                  15

Val

<210> SEQ ID NO 33
<211> LENGTH: 8
<212> TYPE: PRT
<213> ORGANISM: Artificial Sequence
<220> FEATURE:
<223> OTHER INFORMATION: Synthetic: 181163

<400> SEQUENCE: 33

Tyr Gly Val Ser Ala Thr Lys Leu
1               5

<210> SEQ ID NO 34
<211> LENGTH: 17
<212> TYPE: PRT
<213> ORGANISM: Artificial Sequence
<220> FEATURE:
<223> OTHER INFORMATION: Synthetic: 32037

<400> SEQUENCE: 34

Lys Leu Asn Asp Leu Cys Phe Ser Asn Val Tyr Ala Asp Ser Phe Val
1               5                   10                  15

Val

<210> SEQ ID NO 35
<211> LENGTH: 20
<212> TYPE: PRT
<213> ORGANISM: Artificial Sequence
<220> FEATURE:
<223> OTHER INFORMATION: Synthetic: 118609

<400> SEQUENCE: 35

Ser Asn Val Tyr Ala Asp Ser Phe Val Val Lys Gly Asp Asp Val Arg
1               5                   10                  15

Gln Ile Ala Pro
            20

<210> SEQ ID NO 36
<211> LENGTH: 17
<212> TYPE: PRT
<213> ORGANISM: Artificial Sequence
<220> FEATURE:
<223> OTHER INFORMATION: Synthetic: 46522

<400> SEQUENCE: 36

Asn Val Tyr Ala Asp Ser Phe Val Val Lys Gly Asp Asp Val Arg Gln
1               5                   10                  15

Ile

<210> SEQ ID NO 37
<211> LENGTH: 17
<212> TYPE: PRT
<213> ORGANISM: Artificial Sequence
<220> FEATURE:
<223> OTHER INFORMATION: Synthetic: 25378

<400> SEQUENCE: 37

Ile Ala Pro Gly Gln Thr Gly Val Ile Ala Asp Tyr Asn Tyr Lys Leu
1               5                   10                  15
```

Pro

<210> SEQ ID NO 38
<211> LENGTH: 17
<212> TYPE: PRT
<213> ORGANISM: Artificial Sequence
<220> FEATURE:
<223> OTHER INFORMATION: Synthetic: 25250

<400> SEQUENCE: 38

Ile Ala Asp Tyr Asn Tyr Lys Leu Pro Asp Asp Phe Met Gly Cys Val
1               5                   10                  15

Leu

<210> SEQ ID NO 39
<211> LENGTH: 17
<212> TYPE: PRT
<213> ORGANISM: Artificial Sequence
<220> FEATURE:
<223> OTHER INFORMATION: Synthetic: 32070

<400> SEQUENCE: 39

Lys Leu Pro Asp Asp Phe Met Gly Cys Val Leu Ala Trp Asn Thr Arg
1               5                   10                  15

Asn

<210> SEQ ID NO 40
<211> LENGTH: 10
<212> TYPE: PRT
<213> ORGANISM: Artificial Sequence
<220> FEATURE:
<223> OTHER INFORMATION: Synthetic: 32069

<400> SEQUENCE: 40

Lys Leu Pro Asp Asp Phe Met Gly Cys Val
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Synthetic: 7280

<400> SEQUENCE: 41

Cys Val Leu Ala Trp Asn Thr Arg Asn Ile Asp Ala Thr Ser Thr Gly
1               5                   10                  15

Asn

<210> SEQ ID NO 42
<211> LENGTH: 12
<212> TYPE: PRT
<213> ORGANISM: Artificial Sequence
<220> FEATURE:
<223> OTHER INFORMATION: Synthetic: 46242

<400> SEQUENCE: 42

Asn Thr Arg Asn Ile Asp Ala Thr Ser Thr Gly Asn
1               5                   10

<210> SEQ ID NO 43
<211> LENGTH: 18
<212> TYPE: PRT
<213> ORGANISM: Artificial Sequence
<220> FEATURE:

<223> OTHER INFORMATION: Synthetic: 44199

<400> SEQUENCE: 43

Asn Ile Asp Ala Thr Ser Thr Gly Asn Tyr Asn Tyr Lys Tyr Arg Tyr
1               5                   10                  15

Leu Arg

<210> SEQ ID NO 44
<211> LENGTH: 17
<212> TYPE: PRT
<213> ORGANISM: Artificial Sequence
<220> FEATURE:
<223> OTHER INFORMATION: Synthetic: 44198

<400> SEQUENCE: 44

Asn Ile Asp Ala Thr Ser Thr Gly Asn Tyr Asn Tyr Lys Tyr Arg Tyr
1               5                   10                  15

Leu

<210> SEQ ID NO 45
<211> LENGTH: 15
<212> TYPE: PRT
<213> ORGANISM: Artificial Sequence
<220> FEATURE:
<223> OTHER INFORMATION: Synthetic: 66460

<400> SEQUENCE: 45

Thr Ser Thr Gly Asn Tyr Asn Tyr Lys Tyr Arg Tyr Leu Arg His
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic: 21552

<400> SEQUENCE: 46

Gly Asn Tyr Asn Tyr Lys Tyr Arg Tyr Leu Arg His Gly Lys Leu
1               5                   10                  15

<210> SEQ ID NO 47
<211> LENGTH: 20
<212> TYPE: PRT
<213> ORGANISM: Artificial Sequence
<220> FEATURE:
<223> OTHER INFORMATION: Synthetic: 21553

<400> SEQUENCE: 47

Gly Asn Tyr Asn Tyr Lys Tyr Arg Tyr Leu Arg His Gly Lys Leu Arg
1               5                   10                  15

Pro Phe Glu Arg
            20

<210> SEQ ID NO 48
<211> LENGTH: 10
<212> TYPE: PRT
<213> ORGANISM: Artificial Sequence
<220> FEATURE:
<223> OTHER INFORMATION: Synthetic: 46680

<400> SEQUENCE: 48

Asn Tyr Asn Tyr Lys Tyr Arg Tyr Leu Arg
1               5                   10

<210> SEQ ID NO 49
<211> LENGTH: 17
<212> TYPE: PRT
<213> ORGANISM: Artificial Sequence
<220> FEATURE:
<223> OTHER INFORMATION: Synthetic: 46681

<400> SEQUENCE: 49

Asn Tyr Asn Tyr Lys Tyr Arg Tyr Leu Arg His Gly Lys Leu Arg Pro
1               5                   10                  15

Phe

<210> SEQ ID NO 50
<211> LENGTH: 8
<212> TYPE: PRT
<213> ORGANISM: Artificial Sequence
<220> FEATURE:
<223> OTHER INFORMATION: Synthetic: 75237

<400> SEQUENCE: 50

Tyr Asn Tyr Lys Tyr Arg Tyr Leu
1               5

<210> SEQ ID NO 51
<211> LENGTH: 20
<212> TYPE: PRT
<213> ORGANISM: Artificial Sequence
<220> FEATURE:
<223> OTHER INFORMATION: Synthetic: 75239

<400> SEQUENCE: 51

Tyr Asn Tyr Lys Tyr Arg Tyr Leu Arg His Gly Lys Leu Arg Pro Phe
1               5                   10                  15

Glu Arg Asp Ile
            20

<210> SEQ ID NO 52
<211> LENGTH: 8
<212> TYPE: PRT
<213> ORGANISM: Artificial Sequence
<220> FEATURE:
<223> OTHER INFORMATION: Synthetic: 187223

<400> SEQUENCE: 52

His Asn Tyr Lys Tyr Arg Tyr Leu
1               5

<210> SEQ ID NO 53
<211> LENGTH: 15
<212> TYPE: PRT
<213> ORGANISM: Artificial Sequence
<220> FEATURE:
<223> OTHER INFORMATION: Synthetic: 75238

<400> SEQUENCE: 53

Tyr Asn Tyr Lys Tyr Arg Tyr Leu Arg His Gly Lys Leu Arg Pro
1               5                   10                  15

<210> SEQ ID NO 54
<211> LENGTH: 23
<212> TYPE: PRT
<213> ORGANISM: Artificial Sequence
<220> FEATURE:
<223> OTHER INFORMATION: Synthetic: 46641

<400> SEQUENCE: 54

Asn Tyr Lys Tyr Arg Tyr Leu Arg His Gly Lys Leu Arg Pro Phe Glu
1               5                   10                  15

Arg Asp Ile Ser Asn Val Pro
            20

<210> SEQ ID NO 55
<211> LENGTH: 16
<212> TYPE: PRT
<213> ORGANISM: Artificial Sequence
<220> FEATURE:
<223> OTHER INFORMATION: Synthetic: 34589

<400> SEQUENCE: 55

Lys Tyr Arg Tyr Leu Arg His Gly Lys Leu Arg Pro Phe Glu Arg Asp
1               5                   10                  15

<210> SEQ ID NO 56
<211> LENGTH: 17
<212> TYPE: PRT
<213> ORGANISM: Artificial Sequence
<220> FEATURE:
<223> OTHER INFORMATION: Synthetic: 74895

<400> SEQUENCE: 56

Tyr Leu Arg His Gly Lys Leu Arg Pro Phe Glu Arg Asp Ile Ser Asn
1               5                   10                  15

Val

<210> SEQ ID NO 57
<211> LENGTH: 18
<212> TYPE: PRT
<213> ORGANISM: Artificial Sequence
<220> FEATURE:
<223> OTHER INFORMATION: Synthetic: 100664

<400> SEQUENCE: 57

Tyr Leu Arg His Gly Lys Leu Arg Pro Phe Glu Arg Asp Ile Ser Asn
1               5                   10                  15

Val Pro

<210> SEQ ID NO 58
<211> LENGTH: 17
<212> TYPE: PRT
<213> ORGANISM: Artificial Sequence
<220> FEATURE:
<223> OTHER INFORMATION: Synthetic: 39110

<400> SEQUENCE: 58

Leu Arg His Gly Lys Leu Arg Pro Phe Glu Arg Asp Ile Ser Asn Val
1               5                   10                  15

Pro

<210> SEQ ID NO 59
<211> LENGTH: 9
<212> TYPE: PRT
<213> ORGANISM: Artificial Sequence
<220> FEATURE:
<223> OTHER INFORMATION: Synthetic: 32138

<400> SEQUENCE: 59

Lys Leu Arg Pro Phe Glu Arg Asp Ile
1               5

```
<210> SEQ ID NO 60
<211> LENGTH: 12
<212> TYPE: PRT
<213> ORGANISM: Artificial Sequence
<220> FEATURE:
<223> OTHER INFORMATION: Synthetic: 148529

<400> SEQUENCE: 60

Lys Leu Arg Pro Phe Glu Arg Asp Ile Ser Asn Val
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic: 55148

<400> SEQUENCE: 61

Arg Pro Phe Glu Arg Asp Ile Ser Asn Val
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic: 100481

<400> SEQUENCE: 62

Arg Pro Phe Glu Arg Asp Ile Ser Asn Val Pro Phe Ser
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Synthetic: 55149

<400> SEQUENCE: 63

Arg Pro Phe Glu Arg Asp Ile Ser Asn Val Pro Phe Ser Pro Asp Gly
1               5                   10                  15

Lys

<210> SEQ ID NO 64
<211> LENGTH: 17
<212> TYPE: PRT
<213> ORGANISM: Artificial Sequence
<220> FEATURE:
<223> OTHER INFORMATION: Synthetic: 59944

<400> SEQUENCE: 64

Ser Asn Val Pro Phe Ser Pro Asp Gly Lys Pro Cys Thr Pro Pro Ala
1               5                   10                  15

Leu

<210> SEQ ID NO 65
<211> LENGTH: 12
<212> TYPE: PRT
<213> ORGANISM: Artificial Sequence
<220> FEATURE:
<223> OTHER INFORMATION: Synthetic: 47565

<400> SEQUENCE: 65

Pro Phe Ser Pro Asp Gly Lys Pro Cys Thr Pro Pro
```

```
<210> SEQ ID NO 66
<211> LENGTH: 17
<212> TYPE: PRT
<213> ORGANISM: Artificial Sequence
<220> FEATURE:
<223> OTHER INFORMATION: Synthetic: 125415

<400> SEQUENCE: 66

Phe Ser Pro Asp Gly Lys Pro Cys Thr Pro Pro Ala Leu Asn Cys Tyr
1               5                   10                  15
Trp

<210> SEQ ID NO 67
<211> LENGTH: 17
<212> TYPE: PRT
<213> ORGANISM: Artificial Sequence
<220> FEATURE:
<223> OTHER INFORMATION: Synthetic: 60014

<400> SEQUENCE: 67

Ser Pro Asp Gly Lys Pro Cys Thr Pro Pro Ala Leu Asn Cys Tyr Trp
1               5                   10                  15
Pro

<210> SEQ ID NO 68
<211> LENGTH: 17
<212> TYPE: PRT
<213> ORGANISM: Artificial Sequence
<220> FEATURE:
<223> OTHER INFORMATION: Synthetic: 7193

<400> SEQUENCE: 68

Cys Thr Pro Pro Ala Leu Asn Cys Tyr Trp Pro Leu Asn Asp Tyr Gly
1               5                   10                  15
Phe

<210> SEQ ID NO 69
<211> LENGTH: 33
<212> TYPE: PRT
<213> ORGANISM: Artificial Sequence
<220> FEATURE:
<223> OTHER INFORMATION: Synthetic: 558386

<400> SEQUENCE: 69

Ala Leu Asn Cys Tyr Trp Pro Leu Asn Asp Tyr Gly Phe Tyr Thr Thr
1               5                   10                  15
Thr Gly Ile Gly Tyr Gln Pro Tyr Arg Val Val Val Leu Ser Phe Glu
            20                  25                  30
Leu

<210> SEQ ID NO 70
<211> LENGTH: 33
<212> TYPE: PRT
<213> ORGANISM: Artificial Sequence
<220> FEATURE:
<223> OTHER INFORMATION: Synthetic: 2770

<400> SEQUENCE: 70

Ala Leu Asn Cys Tyr Trp Pro Leu Asn Asp Tyr Gly Phe Tyr Thr Thr
1               5                   10                  15
Thr Gly Ile Gly Tyr Gln Pro Tyr Arg Val Val Val Leu Ser Phe Glu
```

20                  25                  30
Leu

<210> SEQ ID NO 71
<211> LENGTH: 6
<212> TYPE: PRT
<213> ORGANISM: Artificial Sequence
<220> FEATURE:
<223> OTHER INFORMATION: Synthetic: 2769

<400> SEQUENCE: 71

Ala Leu Asn Cys Tyr Trp
1               5

<210> SEQ ID NO 72
<211> LENGTH: 17
<212> TYPE: PRT
<213> ORGANISM: Artificial Sequence
<220> FEATURE:
<223> OTHER INFORMATION: Synthetic: 7452

<400> SEQUENCE: 72

Cys Tyr Trp Pro Leu Asn Asp Tyr Gly Phe Tyr Thr Thr Thr Gly Ile
1               5                   10                  15
Gly

<210> SEQ ID NO 73
<211> LENGTH: 17
<212> TYPE: PRT
<213> ORGANISM: Artificial Sequence
<220> FEATURE:
<223> OTHER INFORMATION: Synthetic: 19657

<400> SEQUENCE: 73

Gly Phe Tyr Thr Thr Thr Gly Ile Gly Tyr Gln Pro Tyr Arg Val Val
1               5                   10                  15
Val

<210> SEQ ID NO 74
<211> LENGTH: 7
<212> TYPE: PRT
<213> ORGANISM: Artificial Sequence
<220> FEATURE:
<223> OTHER INFORMATION: Synthetic: 125586

<400> SEQUENCE: 74

Thr Thr Gly Ile Gly Tyr Gln
1               5

<210> SEQ ID NO 75
<211> LENGTH: 21
<212> TYPE: PRT
<213> ORGANISM: Artificial Sequence
<220> FEATURE:
<223> OTHER INFORMATION: Synthetic: 23438

<400> SEQUENCE: 75

Gly Tyr Gln Pro Tyr Arg Val Val Val Leu Ser Phe Glu Leu Leu Asn
1               5                   10                  15
Ala Pro Ala Thr Val
            20

<210> SEQ ID NO 76
<211> LENGTH: 17

```
<212> TYPE: PRT
<213> ORGANISM: Artificial Sequence
<220> FEATURE:
<223> OTHER INFORMATION: Synthetic: 23437

<400> SEQUENCE: 76

Gly Tyr Gln Pro Tyr Arg Val Val Val Leu Ser Phe Glu Leu Leu Asn
1               5                   10                  15

Ala

<210> SEQ ID NO 77
<211> LENGTH: 10
<212> TYPE: PRT
<213> ORGANISM: Artificial Sequence
<220> FEATURE:
<223> OTHER INFORMATION: Synthetic: 51999

<400> SEQUENCE: 77

Gln Pro Tyr Arg Val Val Val Leu Ser Phe
1               5                   10

<210> SEQ ID NO 78
<211> LENGTH: 18
<212> TYPE: PRT
<213> ORGANISM: Artificial Sequence
<220> FEATURE:
<223> OTHER INFORMATION: Synthetic: 71751

<400> SEQUENCE: 78

Val Val Leu Ser Phe Glu Leu Leu Asn Ala Pro Ala Thr Val Cys Gly
1               5                   10                  15

Pro Lys

<210> SEQ ID NO 79
<211> LENGTH: 17
<212> TYPE: PRT
<213> ORGANISM: Artificial Sequence
<220> FEATURE:
<223> OTHER INFORMATION: Synthetic: 69760

<400> SEQUENCE: 79

Val Leu Ser Phe Glu Leu Leu Asn Ala Pro Ala Thr Val Cys Gly Pro
1               5                   10                  15

Lys

<210> SEQ ID NO 80
<211> LENGTH: 17
<212> TYPE: PRT
<213> ORGANISM: Artificial Sequence
<220> FEATURE:
<223> OTHER INFORMATION: Synthetic: 43264

<400> SEQUENCE: 80

Asn Ala Pro Ala Thr Val Cys Gly Pro Lys Leu Ser Thr Asp Leu Ile
1               5                   10                  15

Lys

<210> SEQ ID NO 81
<211> LENGTH: 17
<212> TYPE: PRT
<213> ORGANISM: Artificial Sequence
<220> FEATURE:
<223> OTHER INFORMATION: Synthetic: 6332

<400> SEQUENCE: 81
```

```
Cys Gly Pro Lys Leu Ser Thr Asp Leu Ile Lys Asn Gln Cys Val Asn
1               5                   10                  15
Phe

<210> SEQ ID NO 82
<211> LENGTH: 17
<212> TYPE: PRT
<213> ORGANISM: Artificial Sequence
<220> FEATURE:
<223> OTHER INFORMATION: Synthetic: 69865

<400> SEQUENCE: 82

Val Leu Tyr Glu Asn Gln Lys Gln Ile Ala Asn Gln Phe Asn Lys Ala
1               5                   10                  15
Ile

<210> SEQ ID NO 83
<211> LENGTH: 17
<212> TYPE: PRT
<213> ORGANISM: Artificial Sequence
<220> FEATURE:
<223> OTHER INFORMATION: Synthetic: 51043

<400> SEQUENCE: 83

Gln Ile Ala Asn Gln Phe Asn Lys Ala Ile Ser Gln Ile Gln Glu Ser
1               5                   10                  15
Leu

<210> SEQ ID NO 84
<211> LENGTH: 17
<212> TYPE: PRT
<213> ORGANISM: Artificial Sequence
<220> FEATURE:
<223> OTHER INFORMATION: Synthetic: 29832

<400> SEQUENCE: 84

Lys Ala Ile Ser Gln Ile Gln Glu Ser Leu Thr Thr Thr Ser Thr Ala
1               5                   10                  15
Leu

<210> SEQ ID NO 85
<211> LENGTH: 17
<212> TYPE: PRT
<213> ORGANISM: Artificial Sequence
<220> FEATURE:
<223> OTHER INFORMATION: Synthetic: 14208

<400> SEQUENCE: 85

Glu Ser Leu Thr Thr Thr Ser Thr Ala Leu Gly Lys Leu Gln Asp Val
1               5                   10                  15
Val

<210> SEQ ID NO 86
<211> LENGTH: 17
<212> TYPE: PRT
<213> ORGANISM: Artificial Sequence
<220> FEATURE:
<223> OTHER INFORMATION: Synthetic: 62908

<400> SEQUENCE: 86

Thr Ala Leu Gly Lys Leu Gln Asp Val Val Asn Gln Asn Ala Gln Ala
1               5                   10                  15
```

Leu

<210> SEQ ID NO 87
<211> LENGTH: 17
<212> TYPE: PRT
<213> ORGANISM: Artificial Sequence
<220> FEATURE:
<223> OTHER INFORMATION: Synthetic: 10778

<400> SEQUENCE: 87

Asp Val Val Asn Gln Asn Ala Gln Ala Leu Asn Thr Leu Val Lys Gln
1               5                   10                  15

Leu

<210> SEQ ID NO 88
<211> LENGTH: 17
<212> TYPE: PRT
<213> ORGANISM: Artificial Sequence
<220> FEATURE:
<223> OTHER INFORMATION: Synthetic: 50311

<400> SEQUENCE: 88

Gln Ala Leu Asn Thr Leu Val Lys Gln Leu Ser Ser Asn Phe Gly Ala
1               5                   10                  15

Ile

<210> SEQ ID NO 89
<211> LENGTH: 9
<212> TYPE: PRT
<213> ORGANISM: Artificial Sequence
<220> FEATURE:
<223> OTHER INFORMATION: Synthetic: 2801

<400> SEQUENCE: 89

Ala Leu Asn Thr Leu Val Lys Gln Leu
1               5

<210> SEQ ID NO 90
<211> LENGTH: 17
<212> TYPE: PRT
<213> ORGANISM: Artificial Sequence
<220> FEATURE:
<223> OTHER INFORMATION: Synthetic: 33032

<400> SEQUENCE: 90

Lys Gln Leu Ser Ser Asn Phe Gly Ala Ile Ser Ser Val Leu Asn Asp
1               5                   10                  15

Ile

<210> SEQ ID NO 91
<211> LENGTH: 18
<212> TYPE: PRT
<213> ORGANISM: Artificial Sequence
<220> FEATURE:
<223> OTHER INFORMATION: Synthetic: 1309661

<400> SEQUENCE: 91

Ala Ile Ser Ser Val Leu Asn Asp Ile Leu Ser Arg Leu Asp Lys Val
1               5                   10                  15

Glu Ala

<210> SEQ ID NO 92
<211> LENGTH: 17
<212> TYPE: PRT

```
<213> ORGANISM: Artificial Sequence
<220> FEATURE:
<223> OTHER INFORMATION: Synthetic: 2092

<400> SEQUENCE: 92

Ala Ile Ser Ser Val Leu Asn Asp Ile Leu Ser Arg Leu Asp Lys Val
1               5                   10                  15

Glu

<210> SEQ ID NO 93
<211> LENGTH: 9
<212> TYPE: PRT
<213> ORGANISM: Artificial Sequence
<220> FEATURE:
<223> OTHER INFORMATION: Synthetic: 62221

<400> SEQUENCE: 93

Ser Val Leu Asn Asp Ile Leu Ser Arg
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic: 69657

<400> SEQUENCE: 94

Val Leu Asn Asp Ile Leu Ser Arg Leu
1               5

<210> SEQ ID NO 95
<211> LENGTH: 17
<212> TYPE: PRT
<213> ORGANISM: Artificial Sequence
<220> FEATURE:
<223> OTHER INFORMATION: Synthetic: 27357

<400> SEQUENCE: 95

Ile Leu Ser Arg Leu Asp Lys Val Glu Ala Glu Val Gln Ile Asp Arg
1               5                   10                  15

Leu

<210> SEQ ID NO 96
<211> LENGTH: 9
<212> TYPE: PRT
<213> ORGANISM: Artificial Sequence
<220> FEATURE:
<223> OTHER INFORMATION: Synthetic: 54507

<400> SEQUENCE: 96

Arg Leu Asp Lys Val Glu Ala Glu Val
1               5

<210> SEQ ID NO 97
<211> LENGTH: 17
<212> TYPE: PRT
<213> ORGANISM: Artificial Sequence
<220> FEATURE:
<223> OTHER INFORMATION: Synthetic: 11038

<400> SEQUENCE: 97

Glu Ala Glu Val Gln Ile Asp Arg Leu Ile Thr Gly Arg Leu Gln Ser
1               5                   10                  15

Leu
```

```
<210> SEQ ID NO 98
<211> LENGTH: 9
<212> TYPE: PRT
<213> ORGANISM: Artificial Sequence
<220> FEATURE:
<223> OTHER INFORMATION: Synthetic: 1220

<400> SEQUENCE: 98

Ala Glu Val Gln Ile Asp Arg Leu Ile
1               5

<210> SEQ ID NO 99
<211> LENGTH: 17
<212> TYPE: PRT
<213> ORGANISM: Artificial Sequence
<220> FEATURE:
<223> OTHER INFORMATION: Synthetic: 54599

<400> SEQUENCE: 99

Arg Leu Ile Thr Gly Arg Leu Gln Ser Leu Gln Thr Tyr Val Thr Gln
1               5                   10                  15

Gln

<210> SEQ ID NO 100
<211> LENGTH: 9
<212> TYPE: PRT
<213> ORGANISM: Artificial Sequence
<220> FEATURE:
<223> OTHER INFORMATION: Synthetic: 36723

<400> SEQUENCE: 100

Leu Ile Thr Gly Arg Leu Ala Ala Leu
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic: 36724

<400> SEQUENCE: 101

Leu Ile Thr Gly Arg Leu Gln Ser Leu
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic: 54725

<400> SEQUENCE: 102

Arg Leu Gln Ser Leu Gln Thr Tyr Val
1               5

<210> SEQ ID NO 103
<211> LENGTH: 17
<212> TYPE: PRT
<213> ORGANISM: Artificial Sequence
<220> FEATURE:
<223> OTHER INFORMATION: Synthetic: 59425

<400> SEQUENCE: 103

Ser Leu Gln Thr Tyr Val Thr Gln Gln Leu Ile Arg Ala Ala Glu Ile
```

```
1               5                   10                  15
Arg

<210> SEQ ID NO 104
<211> LENGTH: 18
<212> TYPE: PRT
<213> ORGANISM: Artificial Sequence
<220> FEATURE:
<223> OTHER INFORMATION: Synthetic: 100428

<400> SEQUENCE: 104

Gln Leu Ile Arg Ala Ala Glu Ile Arg Ala Ser Ala Asn Leu Ala Ala
1               5                   10                  15

Thr Lys

<210> SEQ ID NO 105
<211> LENGTH: 17
<212> TYPE: PRT
<213> ORGANISM: Artificial Sequence
<220> FEATURE:
<223> OTHER INFORMATION: Synthetic: 51379

<400> SEQUENCE: 105

Gln Leu Ile Arg Ala Ala Glu Ile Arg Ala Ser Ala Asn Leu Ala Ala
1               5                   10                  15

Thr

<210> SEQ ID NO 106
<211> LENGTH: 17
<212> TYPE: PRT
<213> ORGANISM: Artificial Sequence
<220> FEATURE:
<223> OTHER INFORMATION: Synthetic: 53202

<400> SEQUENCE: 106

Arg Ala Ser Ala Asn Leu Ala Ala Thr Lys Met Ser Glu Cys Val Leu
1               5                   10                  15

Gly

<210> SEQ ID NO 107
<211> LENGTH: 17
<212> TYPE: PRT
<213> ORGANISM: Artificial Sequence
<220> FEATURE:
<223> OTHER INFORMATION: Synthetic: 462

<400> SEQUENCE: 107

Ala Ala Thr Lys Met Ser Glu Cys Val Leu Gly Gln Ser Lys Arg Val
1               5                   10                  15

Asp

<210> SEQ ID NO 108
<211> LENGTH: 17
<212> TYPE: PRT
<213> ORGANISM: Artificial Sequence
<220> FEATURE:
<223> OTHER INFORMATION: Synthetic: 69513

<400> SEQUENCE: 108

Val Leu Gly Gln Ser Lys Arg Val Asp Phe Cys Gly Lys Gly Tyr His
1               5                   10                  15

Leu
```

<210> SEQ ID NO 109
<211> LENGTH: 9
<212> TYPE: PRT
<213> ORGANISM: Artificial Sequence
<220> FEATURE:
<223> OTHER INFORMATION: Synthetic: 56252

<400> SEQUENCE: 109

Arg Val Asp Phe Cys Gly Lys Gly Tyr
1               5

<210> SEQ ID NO 110
<211> LENGTH: 17
<212> TYPE: PRT
<213> ORGANISM: Artificial Sequence
<220> FEATURE:
<223> OTHER INFORMATION: Synthetic: 8239

<400> SEQUENCE: 110

Asp Phe Cys Gly Lys Gly Tyr His Leu Met Ser Phe Pro Gln Ala Ala
1               5                   10                  15

Pro

<210> SEQ ID NO 111
<211> LENGTH: 17
<212> TYPE: PRT
<213> ORGANISM: Artificial Sequence
<220> FEATURE:
<223> OTHER INFORMATION: Synthetic: 38118

<400> SEQUENCE: 111

Leu Met Ser Phe Pro Gln Ala Ala Pro His Gly Val Val Phe Leu His
1               5                   10                  15

Val

<210> SEQ ID NO 112
<211> LENGTH: 10
<212> TYPE: PRT
<213> ORGANISM: Artificial Sequence
<220> FEATURE:
<223> OTHER INFORMATION: Synthetic: 3589

<400> SEQUENCE: 112

Ala Pro His Gly Val Val Phe Leu His Val
1               5                   10

<210> SEQ ID NO 113
<211> LENGTH: 17
<212> TYPE: PRT
<213> ORGANISM: Artificial Sequence
<220> FEATURE:
<223> OTHER INFORMATION: Synthetic: 47823

<400> SEQUENCE: 113

Pro His Gly Val Val Phe Leu His Val Thr Tyr Val Pro Ser Gln Glu
1               5                   10                  15

Arg

<210> SEQ ID NO 114
<211> LENGTH: 9
<212> TYPE: PRT
<213> ORGANISM: Artificial Sequence
<220> FEATURE:
<223> OTHER INFORMATION: Synthetic: 23200

<400> SEQUENCE: 114

Gly Val Val Phe Leu His Val Thr Tyr
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic: 71663

<400> SEQUENCE: 115

Val Val Phe Leu His Val Thr Tyr Val
1               5

<210> SEQ ID NO 116
<211> LENGTH: 17
<212> TYPE: PRT
<213> ORGANISM: Artificial Sequence
<220> FEATURE:
<223> OTHER INFORMATION: Synthetic: 71589

<400> SEQUENCE: 116

Val Thr Tyr Val Pro Ser Gln Glu Arg Asn Phe Thr Thr Ala Pro Ala
1               5                   10                  15

Ile

<210> SEQ ID NO 117
<211> LENGTH: 18
<212> TYPE: PRT
<213> ORGANISM: Artificial Sequence
<220> FEATURE:
<223> OTHER INFORMATION: Synthetic: 79810

<400> SEQUENCE: 117

Glu Arg Asn Phe Thr Thr Ala Pro Ala Ile Cys His Glu Gly Lys Ala
1               5                   10                  15

Tyr Phe

<210> SEQ ID NO 118
<211> LENGTH: 17
<212> TYPE: PRT
<213> ORGANISM: Artificial Sequence
<220> FEATURE:
<223> OTHER INFORMATION: Synthetic: 54989

<400> SEQUENCE: 118

Arg Asn Phe Thr Thr Ala Pro Ala Ile Cys His Glu Gly Lys Ala Tyr
1               5                   10                  15

Phe

<210> SEQ ID NO 119
<211> LENGTH: 33
<212> TYPE: PRT
<213> ORGANISM: Artificial Sequence
<220> FEATURE:
<223> OTHER INFORMATION: Synthetic: 46822

<400> SEQUENCE: 119

Pro Ala Ile Cys His Glu Gly Lys Ala Tyr Phe Pro Arg Glu Gly Val
1               5                   10                  15

Phe Val Phe Asn Gly Thr Ser Trp Phe Ile Thr Gln Arg Asn Phe Phe
            20                  25                  30

Ser

```
<210> SEQ ID NO 120
<211> LENGTH: 12
<212> TYPE: PRT
<213> ORGANISM: Artificial Sequence
<220> FEATURE:
<223> OTHER INFORMATION: Synthetic: 23685

<400> SEQUENCE: 120

His Glu Gly Lys Ala Tyr Phe Pro Arg Glu Gly Val
1               5                   10

<210> SEQ ID NO 121
<211> LENGTH: 17
<212> TYPE: PRT
<213> ORGANISM: Artificial Sequence
<220> FEATURE:
<223> OTHER INFORMATION: Synthetic: 5773

<400> SEQUENCE: 121

Ala Tyr Phe Pro Arg Glu Gly Val Phe Val Phe Asn Gly Thr Ser Trp
1               5                   10                  15

Phe

<210> SEQ ID NO 122
<211> LENGTH: 17
<212> TYPE: PRT
<213> ORGANISM: Artificial Sequence
<220> FEATURE:
<223> OTHER INFORMATION: Synthetic: 18161

<400> SEQUENCE: 122

Phe Val Phe Asn Gly Thr Ser Trp Phe Ile Thr Gln Arg Asn Phe Phe
1               5                   10                  15

Ser

<210> SEQ ID NO 123
<211> LENGTH: 15
<212> TYPE: PRT
<213> ORGANISM: Artificial Sequence
<220> FEATURE:
<223> OTHER INFORMATION: Synthetic: 532052

<400> SEQUENCE: 123

Gly Thr Ser Trp Phe Ile Thr Gln Arg Asn Phe Phe Ser Pro Gln
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Synthetic: 100537

<400> SEQUENCE: 124

Ser Trp Phe Ile Thr Gln Arg Asn Phe Phe Ser Pro Gln Ile Ile
1               5                   10                  15

<210> SEQ ID NO 125
<211> LENGTH: 17
<212> TYPE: PRT
<213> ORGANISM: Artificial Sequence
<220> FEATURE:
<223> OTHER INFORMATION: Synthetic: 43834
```

```
<400> SEQUENCE: 125

Asn Phe Phe Ser Pro Gln Ile Ile Thr Thr Asp Asn Thr Phe Val Ser
1               5                   10                  15

Gly

<210> SEQ ID NO 126
<211> LENGTH: 40
<212> TYPE: PRT
<213> ORGANISM: Artificial Sequence
<220> FEATURE:
<223> OTHER INFORMATION: Synthetic: 15899

<400> SEQUENCE: 126

Phe Phe Ser Pro Gln Ile Ile Thr Thr Asp Asn Thr Phe Val Ser Gly
1               5                   10                  15

Asn Cys Asp Val Val Ile Gly Ile Ile Asn Asn Thr Val Tyr Asp Pro
            20                  25                  30

Leu Gln Pro Glu Leu Asp Ser Phe
        35                  40

<210> SEQ ID NO 127
<211> LENGTH: 9
<212> TYPE: PRT
<213> ORGANISM: Artificial Sequence
<220> FEATURE:
<223> OTHER INFORMATION: Synthetic: 26710

<400> SEQUENCE: 127

Ile Ile Thr Thr Asp Asn Thr Phe Val
1               5

<210> SEQ ID NO 128
<211> LENGTH: 17
<212> TYPE: PRT
<213> ORGANISM: Artificial Sequence
<220> FEATURE:
<223> OTHER INFORMATION: Synthetic: 29108

<400> SEQUENCE: 128

Ile Thr Thr Asp Asn Thr Phe Val Ser Gly Asn Cys Asp Val Val Ile
1               5                   10                  15

Gly

<210> SEQ ID NO 129
<211> LENGTH: 18
<212> TYPE: PRT
<213> ORGANISM: Artificial Sequence
<220> FEATURE:
<223> OTHER INFORMATION: Synthetic: 79833

<400> SEQUENCE: 129

Phe Val Ser Gly Asn Cys Asp Val Val Ile Gly Ile Ile Asn Asn Thr
1               5                   10                  15

Val Tyr

<210> SEQ ID NO 130
<211> LENGTH: 17
<212> TYPE: PRT
<213> ORGANISM: Artificial Sequence
<220> FEATURE:
<223> OTHER INFORMATION: Synthetic: 58143

<400> SEQUENCE: 130
```

-continued

Ser Gly Asn Cys Asp Val Val Ile Gly Ile Ile Asn Asn Thr Val Tyr
1               5                   10                  15

Asp

<210> SEQ ID NO 131
<211> LENGTH: 20
<212> TYPE: PRT
<213> ORGANISM: Artificial Sequence
<220> FEATURE:
<223> OTHER INFORMATION: Synthetic: 68972

<400> SEQUENCE: 131

Val Ile Gly Ile Ile Asn Asn Thr Val Tyr Asp Pro Leu Gln Pro Glu
1               5                   10                  15

Leu Asp Ser Phe
            20

<210> SEQ ID NO 132
<211> LENGTH: 17
<212> TYPE: PRT
<213> ORGANISM: Artificial Sequence
<220> FEATURE:
<223> OTHER INFORMATION: Synthetic: 68971

<400> SEQUENCE: 132

Val Ile Gly Ile Ile Asn Asn Thr Val Tyr Asp Pro Leu Gln Pro Glu
1               5                   10                  15

Leu

<210> SEQ ID NO 133
<211> LENGTH: 17
<212> TYPE: PRT
<213> ORGANISM: Artificial Sequence
<220> FEATURE:
<223> OTHER INFORMATION: Synthetic: 67220

<400> SEQUENCE: 133

Thr Val Tyr Asp Pro Leu Gln Pro Glu Leu Asp Ser Phe Lys Glu Glu
1               5                   10                  15

Leu

<210> SEQ ID NO 134
<211> LENGTH: 17
<212> TYPE: PRT
<213> ORGANISM: Artificial Sequence
<220> FEATURE:
<223> OTHER INFORMATION: Synthetic: 47341

<400> SEQUENCE: 134

Pro Glu Leu Asp Ser Phe Lys Glu Glu Leu Asp Lys Tyr Phe Lys Asn
1               5                   10                  15

His

<210> SEQ ID NO 135
<211> LENGTH: 32
<212> TYPE: PRT
<213> ORGANISM: Artificial Sequence
<220> FEATURE:
<223> OTHER INFORMATION: Synthetic: 10113

<400> SEQUENCE: 135

Asp Ser Phe Lys Glu Glu Leu Asp Lys Tyr Phe Lys Asn His Thr Ser
1               5                   10                  15

Pro Asp Val Asp Leu Gly Asp Ile Ser Gly Ile Asn Ala Ser Val Val
            20                  25                  30

<210> SEQ ID NO 136
<211> LENGTH: 10
<212> TYPE: PRT
<213> ORGANISM: Artificial Sequence
<220> FEATURE:
<223> OTHER INFORMATION: Synthetic: 10112

<400> SEQUENCE: 136

Asp Ser Phe Lys Glu Glu Leu Asp Lys Tyr
1               5                   10

<210> SEQ ID NO 137
<211> LENGTH: 17
<212> TYPE: PRT
<213> ORGANISM: Artificial Sequence
<220> FEATURE:
<223> OTHER INFORMATION: Synthetic: 11740

<400> SEQUENCE: 137

Glu Glu Leu Asp Lys Tyr Phe Lys Asn His Thr Ser Pro Asp Val Asp
1               5                   10                  15

Leu

<210> SEQ ID NO 138
<211> LENGTH: 16
<212> TYPE: PRT
<213> ORGANISM: Artificial Sequence
<220> FEATURE:
<223> OTHER INFORMATION: Synthetic: 9007

<400> SEQUENCE: 138

Asp Lys Tyr Phe Lys Asn His Thr Ser Pro Asp Val Asp Leu Gly Asp
1               5                   10                  15

<210> SEQ ID NO 139
<211> LENGTH: 17
<212> TYPE: PRT
<213> ORGANISM: Artificial Sequence
<220> FEATURE:
<223> OTHER INFORMATION: Synthetic: 32508

<400> SEQUENCE: 139

Lys Asn His Thr Ser Pro Asp Val Asp Leu Gly Asp Ile Ser Gly Ile
1               5                   10                  15

Asn

<210> SEQ ID NO 140
<211> LENGTH: 15
<212> TYPE: PRT
<213> ORGANISM: Artificial Sequence
<220> FEATURE:
<223> OTHER INFORMATION: Synthetic: 60024

<400> SEQUENCE: 140

Ser Pro Asp Val Asp Leu Gly Asp Ile Ser Gly Ile Asn Ala Ser
1               5                   10                  15

<210> SEQ ID NO 141
<211> LENGTH: 9
<212> TYPE: PRT
<213> ORGANISM: Artificial Sequence
<220> FEATURE:
<223> OTHER INFORMATION: Synthetic: 1311514

<400> SEQUENCE: 141

Val Asp Leu Gly Asp Ile Ser Gly Ile
1               5

<210> SEQ ID NO 142
<211> LENGTH: 17
<212> TYPE: PRT
<213> ORGANISM: Artificial Sequence
<220> FEATURE:
<223> OTHER INFORMATION: Synthetic: 9094

<400> SEQUENCE: 142

Asp Leu Gly Asp Ile Ser Gly Ile Asn Ala Ser Val Val Asn Ile Gln
1               5                   10                  15

Lys

<210> SEQ ID NO 143
<211> LENGTH: 15
<212> TYPE: PRT
<213> ORGANISM: Artificial Sequence
<220> FEATURE:
<223> OTHER INFORMATION: Synthetic: 36075

<400> SEQUENCE: 143

Leu Gly Asp Ile Ser Gly Ile Asn Ala Ser Val Val Asn Ile Gln
1               5                   10                  15

<210> SEQ ID NO 144
<211> LENGTH: 20
<212> TYPE: PRT
<213> ORGANISM: Artificial Sequence
<220> FEATURE:
<223> OTHER INFORMATION: Synthetic: 28512

<400> SEQUENCE: 144

Ile Ser Gly Ile Asn Ala Ser Val Val Asn Ile Gln Lys Glu Ile Asp
1               5                   10                  15

Arg Leu Asn Glu
            20

<210> SEQ ID NO 145
<211> LENGTH: 42
<212> TYPE: PRT
<213> ORGANISM: Artificial Sequence
<220> FEATURE:
<223> OTHER INFORMATION: Synthetic: 28513

<400> SEQUENCE: 145

Ile Ser Gly Ile Asn Ala Ser Val Val Asn Ile Gln Lys Glu Ile Asp
1               5                   10                  15

Arg Leu Asn Glu Val Ala Lys Asn Leu Asn Glu Ser Leu Ile Asp Leu
            20                  25                  30

Gln Glu Leu Gly Lys Tyr Glu Gln Tyr Ile
            35                  40

<210> SEQ ID NO 146
<211> LENGTH: 17
<212> TYPE: PRT
<213> ORGANISM: Artificial Sequence
<220> FEATURE:
<223> OTHER INFORMATION: Synthetic: 30435

<400> SEQUENCE: 146

```
Lys Glu Ile Asp Arg Leu Asn Glu Val Ala Lys Asn Leu Asn Glu Ser
1               5                   10                  15

Leu

<210> SEQ ID NO 147
<211> LENGTH: 28
<212> TYPE: PRT
<213> ORGANISM: Artificial Sequence
<220> FEATURE:
<223> OTHER INFORMATION: Synthetic: 558417

<400> SEQUENCE: 147

Glu Ile Asp Arg Leu Asn Glu Val Ala Lys Asn Leu Asn Glu Ser Leu
1               5                   10                  15

Ile Asp Leu Gln Glu Leu Gly Lys Tyr Glu Gln Tyr
            20                  25

<210> SEQ ID NO 148
<211> LENGTH: 28
<212> TYPE: PRT
<213> ORGANISM: Artificial Sequence
<220> FEATURE:
<223> OTHER INFORMATION: Synthetic: 12426

<400> SEQUENCE: 148

Glu Ile Asp Arg Leu Asn Glu Val Ala Lys Asn Leu Asn Glu Ser Leu
1               5                   10                  15

Ile Asp Leu Gln Glu Leu Gly Lys Tyr Glu Gln Tyr
            20                  25

<210> SEQ ID NO 149
<211> LENGTH: 9
<212> TYPE: PRT
<213> ORGANISM: Artificial Sequence
<220> FEATURE:
<223> OTHER INFORMATION: Synthetic: 54680

<400> SEQUENCE: 149

Arg Leu Asn Glu Val Ala Lys Asn Leu
1               5

<210> SEQ ID NO 150
<211> LENGTH: 17
<212> TYPE: PRT
<213> ORGANISM: Artificial Sequence
<220> FEATURE:
<223> OTHER INFORMATION: Synthetic: 14626

<400> SEQUENCE: 150

Glu Val Ala Lys Asn Leu Asn Glu Ser Leu Ile Asp Leu Gln Glu Leu
1               5                   10                  15

Gly

<210> SEQ ID NO 151
<211> LENGTH: 31
<212> TYPE: PRT
<213> ORGANISM: Artificial Sequence
<220> FEATURE:
<223> OTHER INFORMATION: Synthetic epitope

<400> SEQUENCE: 151

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp
```

<210> SEQ ID NO 152
<211> LENGTH: 93
<212> TYPE: DNA
<213> ORGANISM: Artificial Sequence
<220> FEATURE:
<223> OTHER INFORMATION: Synthetic epitope

<400> SEQUENCE: 152
atggctgatt ctaatgggac aattacagtc gaagagctta agaaactgct ggagcaatgg    60
aatcttgtta ttggctttct cttcctgacc tgg                                 93

<210> SEQ ID NO 153
<211> LENGTH: 31
<212> TYPE: PRT
<213> ORGANISM: Artificial Sequence
<220> FEATURE:
<223> OTHER INFORMATION: Synthetic epitope

<400> SEQUENCE: 153

Thr Arg Pro Leu Leu Glu Ser Glu Leu Val Ile Gly Ala Val Ile Leu
1               5                   10                  15
Arg Gly His Leu Arg Ile Ala Gly His His Leu Gly Arg Cys Asp
            20                  25                  30

<210> SEQ ID NO 154
<211> LENGTH: 93
<212> TYPE: DNA
<213> ORGANISM: Artificial Sequence
<220> FEATURE:
<223> OTHER INFORMATION: Synthetic epitope

<400> SEQUENCE: 154
acccgacccc tccttgaatc cgaacttgtt attggcgctg tcattctccg cggacacctt    60
agaattgctg gacatcacct tggacgctgt gat                                 93

<210> SEQ ID NO 155
<211> LENGTH: 72
<212> TYPE: PRT
<213> ORGANISM: Artificial Sequence
<220> FEATURE:
<223> OTHER INFORMATION: Synthetic epitope

<400> SEQUENCE: 155

Gln Asn Val Leu Tyr Glu Asn Gln Lys Leu Ile Ala Asn Gln Phe Asn
1               5                   10                  15
Ser Ala Ile Gly Lys Ile Gln Asp Ser Leu Ser Ser Thr Ala Ser Ala
            20                  25                  30
Leu Gly Lys Leu Gln Asp Val Val Asn Gln Asn Ala Gln Ala Leu Asn
        35                  40                  45
Thr Leu Val Lys Gln Leu Ser Ser Asn Phe Gly Ala Ile Ser Ser Val
    50                  55                  60
Leu Asn Asp Ile Leu Ser Arg Leu
65                  70

<210> SEQ ID NO 156
<211> LENGTH: 216
<212> TYPE: DNA
<213> ORGANISM: Artificial Sequence
<220> FEATURE:
<223> OTHER INFORMATION: Synthetic epitope

<400> SEQUENCE: 156

```
cagaatgtcc tttacgaaaa tcagaaactc atcgcaaatc aattcaactc agcaatcgga        60
aaaattcaag attccctctc ttctaccgca tctgctcttg gcaagcttca agatgtcgtc       120
aatcaaaatg cccaagctct caacactctc gttaaacaac tctcttctaa ctttggtgcc       180
atatcctccg tcctcaatga tatcctttcc cgcctg                                 216
```

<210> SEQ ID NO 157
<211> LENGTH: 24
<212> TYPE: PRT
<213> ORGANISM: Artificial Sequence
<220> FEATURE:
<223> OTHER INFORMATION: Synthetic epitope

<400> SEQUENCE: 157

```
Ser Phe Lys Glu Glu Leu Asp Lys Tyr Phe Lys Asn His Thr Ser Pro
1               5                   10                  15

Asp Val Asp Leu Gly Asp Ile Ser
            20
```

<210> SEQ ID NO 158
<211> LENGTH: 72
<212> TYPE: DNA
<213> ORGANISM: Artificial Sequence
<220> FEATURE:
<223> OTHER INFORMATION: Synthetic epitope

<400> SEQUENCE: 158

```
agtttcaaag aagaacttga caaatacttt aaaaatcata cctcccctga cgtggacctt        60
ggcgatatct cc                                                            72
```

<210> SEQ ID NO 159
<211> LENGTH: 42
<212> TYPE: PRT
<213> ORGANISM: Artificial Sequence
<220> FEATURE:
<223> OTHER INFORMATION: Synthetic epitope

<400> SEQUENCE: 159

```
Gly Ile Asn Ala Ser Val Val Asn Ile Gln Lys Glu Ile Asp Arg Leu
1               5                   10                  15

Asn Glu Val Ala Lys Asn Leu Asn Glu Ser Leu Ile Asp Leu Gln Glu
            20                  25                  30

Leu Gly Lys Tyr Glu Gln Tyr Ile Lys Trp
        35                  40
```

<210> SEQ ID NO 160
<211> LENGTH: 126
<212> TYPE: DNA
<213> ORGANISM: Artificial Sequence
<220> FEATURE:
<223> OTHER INFORMATION: Synthetic epitope

<400> SEQUENCE: 160

```
ggaattaacg catccgtggt taacatacag aagaaaattg acagactgaa cgaagtggcc        60
aagaacctta cgaatctctc catagacctt caagagctgg aaagtacgaa acaatacata       120
aaatgg                                                                  126
```

<210> SEQ ID NO 161
<211> LENGTH: 66
<212> TYPE: PRT

```
<213> ORGANISM: Artificial Sequence
<220> FEATURE:
<223> OTHER INFORMATION: Synthetic epitope

<400> SEQUENCE: 161

Ser Phe Lys Glu Glu Leu Asp Lys Tyr Phe Lys Asn His Thr Ser Pro
1               5                   10                  15

Asp Val Asp Leu Gly Asp Ile Ser Gly Ile Asn Ala Ser Val Val Asn
            20                  25                  30

Ile Gln Lys Glu Ile Asp Arg Leu Asn Glu Val Ala Lys Asn Leu Asn
        35                  40                  45

Glu Ser Leu Ile Asp Leu Gln Glu Leu Gly Lys Tyr Glu Gln Tyr Ile
    50                  55                  60

Lys Trp
65

<210> SEQ ID NO 162
<211> LENGTH: 198
<212> TYPE: DNA
<213> ORGANISM: Artificial Sequence
<220> FEATURE:
<223> OTHER INFORMATION: Synthetic epitope

<400> SEQUENCE: 162
agttttaagg aagaactgga caaatatttc aagaatcata catctccaga cgtggacctg      60
ggcgacattt ctggcattaa cgcatccgtg gttaacattc aaaagaaat tgatagactg      120 aacgaagtgg ctaaaaatct gaacgagtcc cttatcgatc tgcaggaatt gggaaaatac    180
gagcaataca tcaaatgg                                                  198

<210> SEQ ID NO 163
<211> LENGTH: 265
<212> TYPE: PRT
<213> ORGANISM: Artificial Sequence
<220> FEATURE:
<223> OTHER INFORMATION: Synthetic epitope

<400> SEQUENCE: 163

Gly Phe Arg Val Gln Pro Thr Glu Ser Ile Val Arg Phe Pro Asn Ile
1               5                   10                  15

Thr Asn Leu Cys Pro Phe Gly Glu Val Phe Asn Ala Thr Arg Phe Ala
            20                  25                  30

Ser Val Tyr Ala Trp Asn Arg Lys Arg Ile Ser Asn Cys Val Ala Asp
        35                  40                  45

Tyr Ser Val Leu Tyr Asn Ser Ala Ser Phe Ser Thr Phe Lys Cys Tyr
    50                  55                  60

Gly Val Ser Pro Thr Lys Leu Asn Asp Leu Cys Phe Thr Asn Val Tyr
65                  70                  75                  80

Ala Asp Ser Phe Val Ile Arg Gly Asp Glu Val Arg Gln Ile Ala Pro
                85                  90                  95

Gly Gln Thr Gly Lys Ile Ala Asp Tyr Asn Tyr Lys Leu Pro Asp Asp
            100                 105                 110

Phe Thr Gly Cys Val Ile Ala Trp Asn Ser Asn Asn Leu Asp Ser Lys
        115                 120                 125

Val Gly Gly Asn Tyr Asn Tyr Leu Tyr Arg Leu Phe Arg Lys Ser Asn
    130                 135                 140

Leu Lys Pro Phe Glu Arg Asp Ile Ser Thr Glu Ile Tyr Gln Ala Gly
145                 150                 155                 160
```

Ser Thr Pro Cys Asn Gly Val Glu Gly Phe Asn Cys Tyr Phe Pro Leu
165                 170                 175

Gln Ser Tyr Gly Phe Gln Pro Thr Asn Gly Val Gly Tyr Gln Pro Tyr
        180                 185                 190

Arg Val Val Leu Ser Phe Glu Leu Leu His Ala Pro Ala Thr Val
            195                 200                 205

Cys Gly Pro Lys Lys Ser Thr Asn Leu Val Lys Asn Lys Cys Val Asn
        210                 215                 220

Phe Asn Phe Asn Gly Leu Thr Gly Thr Gly Val Leu Thr Glu Ser Asn
225                 230                 235                 240

Lys Lys Phe Leu Pro Phe Gln Gln Phe Gly Arg Asp Ile Ala Asp Thr
            245                 250                 255

Thr Asp Ala Val Arg Asp Pro Gln Thr
            260                 265

<210> SEQ ID NO 164
<211> LENGTH: 795
<212> TYPE: DNA
<213> ORGANISM: Artificial Sequence
<220> FEATURE:
<223> OTHER INFORMATION: Synthetic epitope

<400> SEQUENCE: 164
ggcttcagag tccaaccaac agagtccatc gtgaggttcc ccaatattac taatctgtgc      60
ccctttggtg aggtgtttaa tgctaccaga tttgcctctg tctatgcatg gaatcggaag     120
cggattagta actgcgtcgc cgactatagt gttctctata attccgctag tttctctacg     180
ttcaaatgct atggcgtctc cccgacaaag ctcaatgact tgtgtttcac taacgtctac     240
gctgattctt tcgtgatccg cggtgatgaa gtgcgccaga tcgccccagg acaaaccgga     300
aaaatcgctg attacaatta caaactcccc gacgacttca ccggctgcgt tattgcctgg     360
aactctaaca atctggacag caaggttggc ggcaattata actatctgta ccgcctgttt     420
cggaagtcaa atctcaaacc attcgaacgc gatattagta cagaaatcta tcaggctggc     480 agcacccct gtaacggtgt tgaagggttt aattgttatt ccctctcca atcatacggt      540 ttccagccca caaacggcgt tgggtaccaa ccataccgag tcgttgttct gtcttttgaa     600
cttctccatg ctccagctac tgtttgtgga ccgaagaaga gcaccaatct tgtcaaaaat     660
aaatgcgtga atttaacttt caatggtctt acaggtaccg cgtgcttac cgaaagtaac     720 aaaaaatttc tcccttttca gcagttcgga cgagacattg cagataccac cgacgccgtg     780
agagatccac agacc                                                      795

<210> SEQ ID NO 165
<211> LENGTH: 265
<212> TYPE: PRT
<213> ORGANISM: Artificial Sequence
<220> FEATURE:
<223> OTHER INFORMATION: Synthetic epitope

<400> SEQUENCE: 165

Gly Phe Arg Val Gln Pro Thr Glu Ser Ile Val Arg Phe Pro Asn Ile
1               5                   10                  15

Thr Asn Leu Cys Pro Phe Gly Glu Val Phe Asn Ala Thr Arg Phe Ala
            20                  25                  30

Ser Val Tyr Ala Trp Asn Arg Lys Arg Ile Ser Asn Cys Val Ala Asp
        35                  40                  45

Tyr Ser Val Leu Tyr Asn Ser Ala Ser Phe Ser Thr Phe Lys Cys Tyr

```
                50                  55                  60
Gly Val Ser Pro Thr Lys Leu Asn Asp Leu Cys Phe Thr Asn Val Tyr
 65                  70                  75                  80

Ala Asp Ser Phe Val Ile Arg Gly Asp Glu Val Arg Gln Ile Ala Pro
                 85                  90                  95

Gly Gln Thr Gly Asn Ile Ala Asp Tyr Asn Tyr Lys Leu Pro Asp Asp
                100                 105                 110

Phe Thr Gly Cys Val Ile Ala Trp Asn Ser Asn Asn Leu Asp Ser Lys
                115                 120                 125

Val Gly Gly Asn Tyr Asn Tyr Leu Tyr Arg Leu Phe Arg Lys Ser Asn
130                 135                 140

Leu Lys Pro Phe Glu Arg Asp Ile Ser Thr Glu Ile Tyr Gln Ala Gly
145                 150                 155                 160

Ser Thr Pro Cys Asn Gly Val Lys Gly Phe Asn Cys Tyr Phe Pro Leu
                165                 170                 175

Gln Ser Tyr Gly Phe Gln Pro Thr Tyr Gly Val Gly Tyr Gln Pro Tyr
                180                 185                 190

Arg Val Val Val Leu Ser Phe Glu Leu Leu His Ala Pro Ala Thr Val
                195                 200                 205

Cys Gly Pro Lys Lys Ser Thr Asn Leu Val Lys Asn Lys Cys Val Asn
                210                 215                 220

Phe Asn Phe Asn Gly Leu Thr Gly Thr Gly Val Leu Thr Glu Ser Asn
225                 230                 235                 240

Lys Lys Phe Leu Pro Phe Gln Gln Phe Gly Arg Asp Ile Ala Asp Thr
                245                 250                 255

Thr Asp Ala Val Arg Asp Pro Gln Thr
                260                 265
```

<210> SEQ ID NO 166
<211> LENGTH: 795
<212> TYPE: DNA
<213> ORGANISM: Artificial Sequence
<220> FEATURE:
<223> OTHER INFORMATION: Synthetic epitope

<400> SEQUENCE: 166

```
ggcttcagag tccaaccaac agagtccatc gtgaggttcc ccaatattac taatctgtgc    60
cccctttggtg aggtgtttaa tgctaccaga tttgcctctg tctatgcatg gaatcggaag   120
cggattagta actgcgtcgc cgactatagt gttctctata attccgctag tttctctacg   180
ttcaaatgct atggcgtctc cccgacaaag ctcaatgact gtgtttcac taacgtctac    240
gctgattctt tcgtgatccg cggtgatgaa gtgcgccaga tcgccccagg acaaaccgga   300
aatatcgctg attacaatta caaactcccc gacgacttca ccggctgcgt tattgcctgg   360
aactctaaca atctggacag caaggttggc ggcaattata actatctgta ccgcctgttt   420
cggaagtcaa atctcaaacc attcgaacgc gatattagta cagaaatcta tcaggctggc   480
agcacccct gtaacggtgt taagggtttt aattgttatt tccctctcca atcatacggt    540
ttccagccca catacggcgt tgggtaccaa ccataccgag tcgttgttct gtcttttgaa   600
cttctccatg ctccagctac tgtttgtgga ccgaagaaga gcaccaatct tgtcaaaaat   660
aaatgcgtga attttaactt caatggtctt acaggtaccg gcgtgcttac cgaaagtaac   720
aaaaaatttc tccttttca gcagttcgga cgagacattg cagataccac cgacgccgtg   780
agagatccac agacc                                                    795
```

<210> SEQ ID NO 167
<211> LENGTH: 232
<212> TYPE: PRT
<213> ORGANISM: Artificial Sequence
<220> FEATURE:
<223> OTHER INFORMATION: Synthetic VLP

<400> SEQUENCE: 167

```
Gly Gly Gly Gly Gly Met Glu Asn Ile Thr Ser Gly Phe Leu Gly
1               5                   10                  15

Pro Leu Leu Val Leu Gln Ala Gly Phe Phe Leu Leu Thr Arg Ile Leu
            20                  25                  30

Thr Ile Pro Gln Ser Leu Asp Ser Trp Trp Thr Ser Leu Asn Phe Leu
        35                  40                  45

Gly Gly Ser Pro Val Cys Leu Gly Gln Asn Ser Gln Ser Pro Thr Ser
    50                  55                  60

Asn His Ser Pro Thr Ser Cys Pro Pro Ile Cys Pro Gly Tyr Arg Trp
65                  70                  75                  80

Met Cys Arg Arg Arg Phe Ile Ile Phe Leu Phe Ile Leu Leu Leu Cys
                85                  90                  95

Leu Ile Phe Leu Leu Val Leu Leu Asp Tyr Gln Gly Met Leu Pro Val
            100                 105                 110

Cys Pro Leu Ile Pro Gly Ser Thr Thr Thr Ser Thr Gly Pro Cys Lys
        115                 120                 125

Thr Cys Thr Thr Pro Ala Gln Gly Asn Ser Met Phe Pro Ser Cys Cys
    130                 135                 140

Cys Thr Lys Pro Thr Asp Gly Asn Cys Thr Cys Ile Pro Ile Pro Ser
145                 150                 155                 160

Ser Trp Ala Phe Ala Lys Tyr Leu Trp Glu Trp Ala Ser Val Arg Phe
                165                 170                 175

Ser Trp Val Ser Leu Leu Val Pro Phe Val Gln Trp Phe Val Gly Leu
            180                 185                 190

Ser Pro Thr Val Trp Leu Ser Ala Ile Trp Met Met Trp Tyr Trp Gly
        195                 200                 205

Pro Ser Leu Tyr Ser Ile Val Ser Pro Phe Ile Pro Leu Leu Pro Ile
    210                 215                 220

Leu Phe Cys Leu Trp Val Tyr Ile
225                 230
```

<210> SEQ ID NO 168
<211> LENGTH: 705
<212> TYPE: DNA
<213> ORGANISM: Artificial Sequence
<220> FEATURE:
<223> OTHER INFORMATION: Synthetic VLP

<400> SEQUENCE: 168

```
ggcggcggcg gcggaggcat ggaaaatatc acttctggat ttctggggcc cctcctggtt      60
ctgcaggcag gcttttttcct tttgacacgc atcctgacta tcccacaatc ccttgactca    120
tggtggacat cactgaactt ccttggcggt tctcccgttt gccttggcca gaattcccag    180
tcacccactt ctaatcattc tcccacatct gccctcctca tctgcccagg ctaccgatgg    240
atgtgcagaa gacgcttcat tatcttcctg ttcatttttgc tgctgtgtct gatctttctc    300
ttggtcttgc ttgattatca aggcatgttg cccgtgtgtc ccctcattcc aggatcaaca    360
acgacttcca caggcccctg caaaacgtgc accacaccag cccaaggaaa tagcatgttc    420
```

```
ccctcttgct gttgcactaa acctacggac ggcaactgta cctgtatccc gataccctct    480
tcttgggctt ttgctaaata tctctgggaa tgggcttccg tcagattctc ttgggtgagc    540
cttcttgtcc ccttcgtgca atggttcgtt ggactcagtc ctaccgtttg gctcagcgca    600
atctggatga tgtggtactg gggaccatct ctctacagca ttgtttcacc ctttatcccc    660
ctgcttccaa tcttgttctg cttgtgggtt tatatataaa cgcgt                   705
```

CORONAVIRUS VACCINE AND METHODS OF USE THEREOF

CROSS-REFERENCE TO RELATED APPLICATIONS

This application claims priority to U.S. Provisional Application 63/037,367 filed on Jun. 10, 2020. The complete content thereof is herein incorporated by reference.

SEQUENCE LISTING

This document incorporates by reference an electronic sequence listing text file, which was electronically submitted along with this document. The text file is named 15660001AA_ST25, is 53 kilobytes, and was created on Jun. 7, 2021.

FIELD OF THE INVENTION

The invention generally relates to a coronavirus vaccine and particularly to an immunogenic composition comprising polypeptide antigens that are derived from conserved C-terminal domains of coronavirus spike protein (S protein). The composition may further comprise at least one polypeptide antigen derived from the first Heptad Repeat (HR1) and/or the second Heptad Repeat (HR2) domain of S protein and/or coronavirus membrane protein (M protein) and/or coronavirus receptor binding domain (RBD). The present invention also contemplates a vaccine composition comprising coronavirus antigens presented on a virus-like-particle (VLP). In addition, the invention relates to a method of inducing an immune response to coronavirus antigens to protect a subject from acquiring COVID-19.

BACKGROUND

The COVID-19 pandemic caused by severe acute respiratory syndrome coronavirus 2 (SARS-CoV-2) has caused untold devastation worldwide. Similar to other human coronaviruses, such as the Middle East respiratory syndrome coronavirus (MERS-CoV) and SARS-CoV-1, SARS-CoV-2 may have a zoonotic origin. To date, 160 million people have been infected and 3.3 million have died worldwide, with mortality and morbidity still rising in various parts of the world. Apart from the medical and public health havoc, the SARS-CoV-2 pandemic has also caused unprecedented social, economic and governmental upheaval unseen in modern times.

As a result, there has been a thrust towards rapid development of vaccines and therapeutics to tackle this urgent problem. The prophylactic vaccines are based on diverse platforms that include RNA technology, non-replicating viral vectors, inactivated virus, subunit vaccines, as well as DNA vaccines. A number of therapeutic approaches using monoclonal antibodies have also been reported. However, there are limited pre-clinical data published on the SARS-CoV-2 vaccines under development. Long range safety studies have not yet been reported with test vaccines against SARS-CoV-2. In the case of therapeutic antibodies, based on published research, focus has primarily been on isolation techniques, structural models and mechanism of action of therapeutic antibodies against SARS-CoV-2. Further investigation on the safety aspects of either vaccines or therapeutic antibodies against SARS-CoV-2 is needed.

SARS-CoV-2 pathophysiology shows that the COVID-19 disease clinically manifests in multiple forms. Mild to moderate disease has been reported in 80% of cases, severe disease in ~15% cases and critical disease in ~5% cases. Subjects with mild disease recover with little to no medical intervention while severe and critical disease require hospitalization and, in some cases, intensive care. Some patients may suffer from life-threatening acute respiratory distress syndrome (ARDS) with possible fatal outcomes. Severe disease is seen more often in males, particularly in those with co-morbidities such as cardiovascular disease and diabetes. Paradoxically, patients with severe disease have increased IgG response and higher titers of total antibodies against SARS-CoV-2, which are associated with worse outcomes. As such, the role of immune cells such as macrophages, dendritic cells and T cells in COVID-19 disease has not been systematically studied. Antibody dependent enhancement (ADE) of SARS-CoV-2 may result in potential side effects in those patients who produce undesirable non-neutralizing antibodies against the virus.

SARS-CoV-2 infects cells through the ACE2 receptor expressed on type II pneumocytes in the lung. However, ACE2 is also expressed in the heart, kidney, intestine as well as the vascular endothelium. The major determinant of the ACE2 cognate binding is the homotrimeric spike glycoprotein (S) expressed as 70-80 copies on the surface of SARS-CoV-2. The S protein consists of two domains—S1 and S2—that are linked by a fusion peptide FP. S1 domain contains the ACE2 receptor binding domain (RBD) while the S2 domain promotes fusion of the virus into the cell membrane using a polybasic furin cleavage site located within the S1-S2 boundary.

Majority of the vaccine candidates currently being clinically tested make use of the S protein of SARS-CoV-2 alone as the main immunogen, mostly in a non-specific manner. In the case of non-replicating virus vectors, the S protein is cloned and expressed in adenovirus vectors. Similarly, for RNA based vaccines, the S protein mRNA is encapsulated in lipid nanoparticles and used for intramuscular injections. The DNA based vaccine also encodes the S protein and is electroporated into subjects for vaccinations. Thus, while initial attempts at developing vaccines and therapeutic antibodies against SARS-CoV-2 focused solely on the use of S protein, it is increasingly becoming clear that without rational considerations into immunogen design, formulation and manufacturer, clinical trials could get entrapped in safety pitfalls, thereby jeopardizing global efforts at controlling the pandemic.

Three major areas of concerns regarding safety of current vaccines against SARS-CoV-2 have emerged. One of the concerns of the currently developed vaccines is that some of the vaccines may trigger antibody dependent enhancement (ADE) of viral infection. ADE is a phenomenon wherein antibodies that are elicited against a viral antigen actually enhance the uptake of the virus, causing more severe disease. The enhancement is typically the result of non-neutralizing or sub-neutralizing antibodies generated against viral antigen (Iwasaki et. al., 2020). While the role of ADE in SARS-CoV-2 has not been fully established, several lines of evidence suggest that it could potentially be of significant safety concern in the clinic (Kamikubo et. al., 2020).

A second challenge to developing a safe vaccine is the need to reduce an off-target pathological activation of the immune cells. There is emerging evidence that TH17 responses can direct certain cellular responses upon vaccination with inactivated vaccines and those based on viral vectors, and that the TH17 activation leads to up-regulation of the pro-inflammatory cytokines IL-6 and IL-1β (Blanco-Melo et. al., 2020, Liu et. al., 2020). IL-6 upregulation has been prominently observed in patients with severe COVID-19 disease (Herold et. al., 2020). In rhesus macaques vaccinated with a modified vaccinia Ankara (MVA) virus encoding the SARS-CoV-1 S glycoprotein, anti-spike antibodies promoted MCP1 and IL-8 production in alveolar macrophages causing acute lung injury (Liu et. al., 2019). An exemplary mouse study showed that, when animals were challenged with SARS-CoV-1 after immunization with either an inactivated viral vaccine or rDNA-based vaccine with or without alum, the Th2-type pathology with prominent eosinophil infiltration with eosinophil scores were significantly lower for non-vaccine groups than for vaccine groups of across the tested mouse strains (Tseng et. al., 2012). Spleen atrophy and lymph node necrosis have also been reported to be deceased in COVID-19 patients suggesting immune mediated pathology in SARS-CoV-2 infections (Feng et. al., 2020).

A third concern regarding of some vaccines against SARS-CoV-2 is a possibility of triggering endothelium inflammation. Endothelial cells express ACE2, the receptor bound by SARS-CoV-2 to infect lung epithelial cells. Not surprisingly, in additional to pulmonary complications, additional clinical symptoms of COVID-19 include high blood pressure, thrombosis and pulmonary embolism. This raises the question of whether the endothelium is a key target organ of SARS-CoV-2 (Sardu et. al., 2020). Of note, supernatants from SARS-CoV-2 infected capillary organoid cultures could also infect Vero cells demonstrating that the production of viable progeny virus. Postmortem analysis of a SARS-CoV-2 patient with hypertension showed evidence of direct viral infection of the endothelial cell and diffused endothelial inflammation causing vascular dysfunction by shifting the equilibrium towards vasoconstriction, ischemia and a procoagulant state (Fox et. al., 2020; Tian et. al., 2020; Varga et. al., 2020).

Therapies such as afucosylated or defucosylated monoclonal antibodies have been proposed, however, in some instances, such therapies are pathogenic.

Additionally, there is a great need to quickly develop and verify efficacy and safety of a vaccine for the new emergent SARS-CoV-2 virus variants, and subsequently manufacture the vaccine on a very large scale, to meet immediate population demands. Use of shorter antigenic peptides that are developed from computer-based rational designs provide several advantages in comparison to conventional vaccines made of dead or attenuated pathogens or inactivated toxins. This version of polypeptide antigens may be synthesized rapidly and produced with much lower cost.

Thus, there is a need in the art for an improved SARS-CoV-2 vaccine with effective prophylactic properties and ability to control potential side effects to the lowest degree or to none. Further, there is a need for diversifying new SARS-CoV-2 vaccine targets and more specifically to new targets based on the conserved regions for being effective against other potential variants, in the most cost effective and safety-oriented manner.

SUMMARY OF THE INVENTION

The disclosure relates to the field of viral vaccines and methods of use of such vaccines to protect a subject from virus infection. In particular, the invention is an immunogenic composition comprising at least one antigenic polypeptide and methods of use to evoke an immune response to one or more coronavirus spike (S) protein and/or membrane (M) protein to protect an immunized subject from acquiring a viral-related disease such as COVID-19. The antigenic polypeptides or fragments derived from the S protein and/or M protein may be included in the composition separately or fused by a linker region. The antigens are presented on the surface of Virus-Like Particles (VLP) for inhibiting the fusion of coronavirus particles during the viral entry to a host cell. One of the main advantageous features of the present invention is to selectively target the viral fusion stage by introducing at least one antigenic polypeptide or fragment derived from at least one conserved domain of the S protein from SARS-CoV-2 or any other coronaviruses with the conserved domain, such as the first heptad repeat (HR1) and/or the second heptad repeat (HR2), in which the at least one antigenic polypeptide is presented on the surface of VLP as a path to develop a safe and affordable vaccine. By presenting rationally designed antigens on VLPs, host immune responses that block viral fusion will result in prevention of unwanted cytokine production and immunopathology. The S protein derived antigens may be manufactured in eukaryotic cells (e.g., mammalian cells, plant cells, fungal cells, etc.), more preferably in mammalian cells, to ensure proper folding and glycosylation of viral proteins as in the human system.

One aspect of the invention is a vaccine composition that is able to induce an immune response against a coronavirus, comprising a VLP presenting at least one polypeptide or fragment of the coronavirus as an immunogen, wherein the at least one antigenic polypeptide or fragment may be derived from HR1 domain and/or HR2 domain of S protein and/or M protein from the coronavirus. In some embodiments, the at least one antigenic polypeptide or fragment is derived from both HR1 and HR2 domains and/or the linker regions between the HR1 and HR2 domains. In other embodiments, the at least one antigenic polypeptide or fragment may be derived from N-terminal or C-terminal region of the coronavirus M protein.

Another aspect of the invention is a vaccine composition that is able to induce an immune response to coronavirus and to inhibit viral fusion, wherein the at least one antigenic polypeptide or fragment presented on VLP has a sequence selected from the group consisting of SEQ ID NOs:1 to 166. In some embodiments, the VLP has a sequence as set forth in SEQ ID NO: 167 or SEQ ID NO: 168. In some embodiments, the at least one antigenic polypeptide includes a plurality of polypeptides as set forth in SEQ ID Nos 1-7, 83-102, and 135-150

Another aspect of the invention is a method of inducing an immune response to at least one coronavirus antigen in a subject in need thereof, comprising the step of administering an immunogenic composition comprising a VLP presenting at least one antigenic polypeptide or fragment derived from S protein and/or M protein to the subject. In some embodiments, the method further comprises allowing a suitable period of time to elapse and administering at least one additional dose of the immunogenic composition. The immunogenic composition comprising the vaccine can be administered intramuscularly or intradermally with a hypodermic, transdermic or intradermal needle or with a needle-free device. In some embodiments, the immunogenic composition comprising the vaccine can be administered by intranasal and/or ocular delivery. In some embodiments, at least one adjuvant may be included in the vaccine composition. In other embodiments, 1-150 µg of the antigen presenting VLP is administered to the subject in each dose. In addition, a suitable period of time is defined as a time sufficient for producing antibodies against the immunogenic composition of the present invention in a subject.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The accompanying drawings, which are incorporated in and constitute a part of this specification, illustrate embodiments of the invention and, together with a general description of the invention given above and the detailed description given below serve to explain the invention.

FIG. 3A-B show a front view (A) and a top view (B) of sequence conservation within C-terminal domains of SARS-CoV-2 S protein.

DETAILED DESCRIPTION

Figure 1:
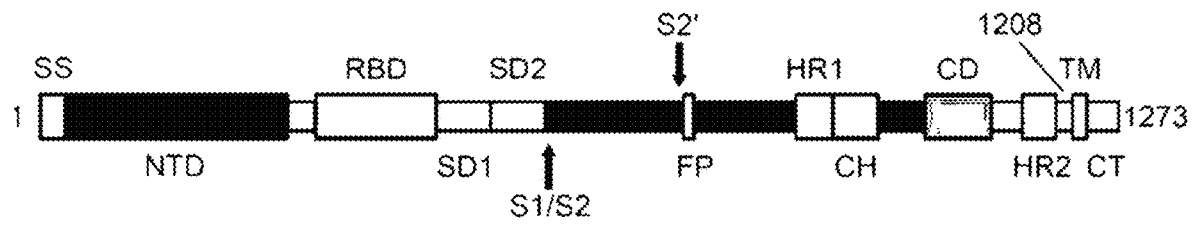
FIG. 1 shows a structural organization of various domains within SARS-CoV-2 S protein. SS, signal sequence; S2', S2' protease cleavage site; FP, fusion peptide; HR1, heptad repeat 1; CH, central helix CD, connector domain; HR2, heptad repeat 2; TM, transmembrane domain; CT, cytoplasmic tail. The S protein also contains a predicted set of 24 N-glycans and 4 O-glycan for each monomer of which 17 N-glycans have been confirmed using cryo-EM.

Embodiments of the invention relate to an immunogenic composition comprising at least one antigenic polypeptide or fragment thereof, wherein the at least one polypeptide or fragment antigen thereof is derived from coronavirus spike (S) protein and/or membrane (M) protein. In particular, HR1 domain and/or HR2 domain of SARS-CoV-2 S protein is contemplated as the protein in which at least one antigenic polypeptide or fragment thereof is derived from. When incorporated together, the polypeptide or fragment derived from HR1 and HR2 may be fused, chemical and/or bioconjugated to each other by a linker region and presented on the surface of Virus-Like-Particles (VLP) for inhibiting the fusion of SARS-CoV-2 virus during the viral entry to a host cell. The disclosure also relates to a method of use of such immunogenic composition to protect a subject from COVID-19 infection.

The vast majority of the vaccines that are currently being developed target the spike (S) protein of SARS-CoV-2 in a non-specific manner, opening the possibilities of unwanted immune responses and pathologies clinically reported in severe and critical cases of COVID-19. In particular, acute lung injury, immunopathology and endothelial dysfunction have been described in deceased patients, raising questions about the fundamental mechanism of COVID-19 etiology. In the present disclosure, an alternate strategy based on rational design that selectively targets blockade of viral fusion as a path to develop a safe and affordable vaccine against SARS-CoV-2 is described. The present invention displays antigenic polypeptides or fragments that are derived from specific, membrane-proximal, conserved domains within the SARS-CoV-2 S protein as well as from membrane glycoprotein as immunogens. By presenting rationally designed antigens on VLP, host immune responses that block viral fusion will result in prevention of unwanted cytokine production and immunopathology. Manufacture in mammalian cells ensures proper folding and glycosylation of viral proteins as in the human system, further strengthening vaccine safety. Combined with proven, scalable, cost-effective manufacturing technologies, the present invention may provide a shelf life and lower cost of goods for people living in low-income countries.

In preferred embodiments, a vaccine composition of the present invention induces an immune response to coronavirus and inhibits viral fusion. The immunogenic composition comprises at least one antigenic polypeptide or fragment thereof. In preferred embodiments, one or more antigens are presented on VLP. In other embodiments the antigens may be displayed or included in a VLP by a plurality of methods described below. In some embodiments, the antigenic polypeptide or fragment has 80% or more, preferably 90% or more, more preferably 95% or more sequence identity with a sequence selected from the group consisting of SEQ ID NOs:1 to 166. In some embodiments, the VLP has 80% or more, preferably 90% or more, more preferably 95% or more sequence identity with a sequence selected from the group consisting of SEQ ID NOs:167-168.

For each cDNA sequence presented herein, the invention includes the mRNA equivalent of the cDNA, meaning that the invention includes each cDNA sequence wherein each T is replaced by U. Exemplary antigenic peptide sequences include:

Amino Acids 1-31 Covering Amino Terminus of M Protein:

(SEQ ID NO: 151)
MADSNGTITVEELKKLLEQWNLVIGFLFLTW

Corresponding DNA Sequence:

(SEQ ID NO: 152)
ATGGCTGATTCTAATGGGACAATTACAGTCGAAGAGCTTAAGAAATC

GCTGGAGCAATGGAATCTTGTTATTGGCTTTCTCTTCCTGACCTGG

Amino Acids 130-160 from Carboxy Terminus of M Protein:

(SEQ ID NO: 153)
TRPLLESELVIGAVILRGHLRIAGHHLGRCD

Corresponding DNA Sequence:

(SEQ ID NO: 154)
ACCCGACCCCTCCTTGAATCCGAACTTGTTATTGGCGCTGTCATTCT

CCGCGGACACCTTAGAATTGCTGGACATCACCTTGGACGCTGTGAT

Amino Acids 913-984 Covering the First Heptad Repeat HR1 of S Protein:

(SEQ ID NO: 155)
QNVLYENQKLIANQFNSAIGKIQDSLSSTASALGKL

QDVVNQNAQALNTLVKQLSSNFGAISSVLNDILSRL

Corresponding DNA Sequence:

(SEQ ID NO: 156)
CAGAATGTCCTTTACGAAAATCAGAAA

CTCATCGCAAATCAATTCAACTCAGCA

ATCGGAAAAATTCAAGATTCCCTCTCT

TCTACCGCATCTGCTCTTGGCAAGCTT

CAAGATGTCGTCAATCAAAATGCCCAA

GCTCTCAACACTCTCGTTAAACAACTC

TCTTCTAACTTTGGTGCCATATCCTCC

GTCCTCAATGATATCCTTTCCCGCCTG

Amino Acids 1147-1170 Covering the Linker Region Connecting HR1 and HR2:

(SEQ ID NO: 157)
SFKEELDKYFKNHTSPDVDLGDIS

Corresponding DNA Sequence:

(SEQ ID NO: 158)
AGTTTCAAAGAAGAACTTGACAAATACT

TTAAAAATCATACCTCCCCTGACGTGG

ACCTTGGCGATATCTCC

Amino Acids 1171-1212 Covering the Second Heptad Repeat HR2 of S Protein:

(SEQ ID NO: 159)
GINASVVNIQKEIDRLNEVAKNLNESLIDLQELGKYEQYIKW

Corresponding DNA Sequence:

(SEQ ID NO: 160)
GGAATTAACGCATCCGTGGTTAACATA

CAGAAAGAAATTGACAGACTGAACGAA

GTGGCCAAGAACCTTAACGAATCTCTC

ATAGACCTTCAAGAGCTGGGAAAGTAC

GAACAATACATAAAATGG

Amino acids 1147-1212 covering both the linker as well as HR2 regions:

(SEQ ID NO: 161)
SFKEELDKYFKNHTSPDVDLGDLSGINASVVNIQ

KEIDRLNEVAKNLNESLIDLQELGKYEQYIKW

Corresponding DNA Sequence:

(SEQ ID NO: 162)
AGTTTTAAGGAAGAACTGGACAAATATTTCAAGAATCATA

CATCTCCAGACGTGGACCTGGGCGACATTTCTGGCATTAA

CGCATCCGTGGTTAACATTCAAAAAGAAATTGATAGACTG

AACGAAGTGGCTAAAAATCTGAACGAGTCCCTTATCGATC

TGCAGGAATTGGGAAAATACGAGCAATACATCAAATGG

Amino Acids 318-541 Representing RBD of S Protein:

(SEQ ID NO: 163)
GFRVQPTESIVRFPNITNLCPPGEVFNATRFASVYAWNR

KRISNCVADYSVLYNSASFSTFKCYGVSPTKLNDLCFTN

VYADSFVIRGDEVRQIAPGQTGKIADYNYKLPDDFTGCV

IAWNSNNLDSKVGGNYNYLYRLFRKSNLKPFERDISTEI

YQAGSTPCNGVEGFNCYFPLQSYGFQPTNGVGYQPYRVV

VLSFELLHAPATVCGPKKSTNLVKNFCCVNFNFNGLTGT

GVLTESNKKFLPFQQFGRDIADTTDAVRDPQT

Corresponding DNA Sequence:

(SEQ ID NO: 164)
GGCTTCAGAGTCCAACCAACAGAGTCCATCGTGAGGTTC

CCCAATATTACTAATCTGTGCCCCTTTGGTGAGGTGTTT

AATGCTACCAGATTTGCCTCTGTCTATGCATGGAATCGG

AAGCGGATTAGTAACTGCGTCGCCGACTATAGTGTTCTC

TATAATTCCGCTAGTTTCTCTACGTTCAAATGCTATGGC

GTCTCCCCGACAAAGCTCAATGACTTGTGTTTCACTAAC

GTCTACGCTGATTCTTTCGTGATCCGCGGTGATGAAGTG

CGCCAGATCGCCCCAGGACAAACCGGAAAAATCGCTGAT

TACAATTACAAACTCCCCGACGACTTCACCGGCTGCGTT

ATTGCCTGGAACTCTAACAATCTGGACAGCAAGGTTGGC

GGCAATTATAACTATCTGTACCGCCTGTTTCGGAAGTCA

AATCTCAAACCATTCGAACGCGATATTAGTACAGAAATC

TATCAGGCTGGCAGCACCCCCTGTAACGGTGTTGAAGGG

TTTAATTGTTATTTCCCTCTCCAATCATACGGTTTCCAG

CCCACAAACGGCGTTGGGTACCAACCATACCGAGTCGTT

GTTCTGTCTTTTGAACTTCTCCATGCTCCAGCTACTGTT

TGTGGACCGAAGAAGAGCACCAATCTTGTCAAAAATAAA

TGCGTGAATTTTAACTTCAATGGTCTTACAGGTACCGGC

GTGCTTACCGAAAGTAACAAAAAATTTCTCCCTTTTCAG

CAGTTCGGACGAGACATTGCAGATACCACCGACGCCGTG

AGAGATCCACAGACC

Amino Acids 318-541 Representing RBD of S Protein with K417N/E484K/N501Y Mutations:

(SEQ ID NO: 165)
GFRVQPTESIVRFPNITNLCPFGEVFNATRFASVYAWNR

KRISNCVADYSVLYNSASFSTFKCYGVSPTKLNDLCFTN

VYADSFVIRGDEVRQIAPGQTGNIADYNYKLPDDFTGCV

IAWNSNNLDSKVGGNYNYLYRLFRKSNLKPFERDISTEI

YQAGSTPCNGVKGFNCYFPLQSYGFQPTYGVGYQPYRVV

VLSFELLHAPATVCGPKKSTNLVKNKCVNFNFNGLTGTG

VLTESNKKFLPFQQFGRDIADTTDAVRDPQT

Corresponding DNA Sequence:

(SEQ ID NO: 166)
GGCTTCAGAGTCCAACCAACAGAGTCCATCGTGAGGTTC

CCCAATATTACTAATCTGTGCCCCTTTGGTGAGGTGTTT

AATGCTACCAGATTTGCCTCTGTCTATGCATGGAATCGG

AAGCGGATTAGTAACTGCGTCGCCGACTATAGTGTTCTC

TATAATTCCGCTAGTTTCTCTACGTTCAAATGCTATGGC

GTCTCCCCGACAAAGCTCAATGACTTGTGTTTCACTAAC

GTCTACGCTGATTCTTTCGTGATCCGCGGTGATGAAGTG

CGCCAGATCGCCCCAGGACAAACCGGAAATATCGCTGAT

TACAATTACAAACTCCCCGACGACTTCACCGGCTGCGTT

ATTGCCTGGAACTCTAACAATCTGGACAGCAAGGTTGGC

GGCAATTATAACTATCTGTACCGCCTGTTTCGGAAGTCA

AATCTCAAACCATTCGAACGCGATATTAGTACAGAAATC

TATCAGGCTGGCAGCACCCCCTGTAACGGTGTTAAAGGG

TTTAATTGTTATTTCCCTCTCCAATCATACGGTTTCCAG

CCCACATACGGCGTTGGGTACCAACCATACCGAGTCGTT

GTTCTGTCTTTTGAACTTCTCCATGCTCCAGCTACTGTT

TGTGGACCGAAGAAGAGCACCAATCTTGTCAAAAATAAA

TGCGTGAATTTTAACTTCAATGGTCTTACAGGTACCGGC

GTGCTTACCGAAAGTAACAAAAAATTTCTCCCTTTTCAG

CAGTTCGGACGAGACATTGCAGATACCACCGACGCCGTG

AGAGATCCACAGACC

Exemplary VLP Amino Acid Sequence:

(SEQ ID NO: 167)
GGGGGGMENITSGFLGPLLVLQAGFFLLTRILTIPQSLDSW

WTSLNFLGGSPVCLGQNSQSPTSNHSPTSCPPICPGYRWMC

RRRFIIFLFILLLCLIFLLVLLDYQGMLPVCPLIPGSTTTS

TGPCKTCTTPAQGNSMFPSCCCTKPTDGNCTCIPIPSSWAF

AKYLWEWASVRFSWVSLLVPFVQWFVGLSPTVWLSAIWMMW

YWGPSLYSIVSPFIPLLPILFCLWVYI

Exemplary VLP DNA Sequence:

(SEQ ID NO: 168)
GGCGGCGGCGGCGGAGGCATGGAAAATATCACTTCTGGATT

TCTGGGGCCCCTCCTGGTTCTGCAGGCAGGCTTTTTCCTTT

TGACACGCATCCTGACTATCCCACAATCCCTTGACTCATGG

TGGACATCACTGAACTTCCTTGGCGGTTCTCCCGTTTGCCT

TGGCCAGAATTCCCAGTCACCCACTTCTAATCATTCTCCCA

CATCTTGCCCTCCTATCTGCCCAGGCTACCGATGGATGTGC

AGAAGACGCTTCATTATCTTCCTGTTCATTTTGCTGCTGTG

TCTGATCTTTCTCTTGGTCTTGCTTGATTATCAAGGCATGT

TGCCCGTGTGTCCCCTCATTCCAGGATCAACAACGACTTCC

ACAGGCCCCTGCAAAACGTGCACCACACCAGCCCAAGGAAA

TAGCATGTTCCCCTCTTGCTGTTGCACTAAACCTACGGACG

GCAACTGTACCTGTATCCCGATACCCTCTTCTTGGGCTTTT

GCTAAATATCTCTGGGAATGGGCTTCCGTCAGATTCTCTTG

GGTGAGCCTTCTTGTCCCCTTCGTGCAATGGTTCGTTGGAC

TCAGTCCTACCGTTTGGCTCAGCGCAATCTGGATGATGTGG

TACTGGGGACCATCTCTCTACAGCATTGTTTCACCCTTTAT

CCCCCTGCTTCCAATCTTGTTCTGCTTGTGGGTTTATATAT

AAACGCGT

Coronaviruses constitute the subfamily Orthocoronavirinae, in the family Coronaviridae, order Nidovirales, and realm Riboviria. Coronaviruses have four genera: alpha-, beta-, gamma-, and delta-coronaviruses. They are enveloped viruses with a positive-sense single-stranded RNA genome and a nucleocapsid of helical symmetry. The genome size of coronaviruses ranges from approximately 26 to 32 kilobases. Exemplary coronaviruses that may be treated with the compositions of the disclosure include, but are not limited to, SARS-Cov, SARS-Cov-2, MERS-Cov, HCoV-OC43, HCoV-HKU1, HCoV-229E, and HCoV-NL63.

As used herein, the term "severe acute respiratory syndrome coronavirus 2 (SARS-CoV-2)", "2019 novel coronavirus (2019-nCoV)", "human coronavirus 2019 (HCoV-19)" or "severe acute respiratory syndrome-related coronavirus (SARSr-CoV)" refers to virus comprising a virion with 50-200 nanometers in diameter and a genomic size of about 30 kilobases, encoding multiple structural proteins, such as the S (spike), E (envelope), M (membrane) and N (nucleocapsid), and non-structural proteins. Coronaviruses are a group of related RNA viruses that cause diseases in mammals and birds. In humans and birds, they cause respiratory tract infections that can range from mild to lethal. Mild illnesses in humans include some cases of the common cold (which is also caused by other viruses, predominantly rhinoviruses), while more lethal varieties can cause SARS, MERS, and COVID-19.

Since SARS-CoV-2 shares 80% sequence homology with SARS-CoV-1, the antibodies against S protein in SARS-CoV-2 may also trigger immune response against SARS-Cov-1. Thus, other virus types such as SARS-CoV (i.e., SARS-CoV-1) and MERS-CoV that are similar in virion structure may also be subjected to the present invention. As used herein, the term "S protein" or "Spike protein" is used to refer to a knoblike structured (i.e., spikes) peplomer, which is composed of glycoprotein to project from the lipid bilayer of the surface envelope of an enveloped virus. The "spike protein" or "S protein" is interchangeably referred to a protein and/or a glycoprotein. Furthermore, the sequences encoding the SARS-CoV-2 glycoprotein may also be referred to as a peptide or amino acid sequence.

As used herein, the terms "polypeptide", "short protein", "fragment of protein", "polypeptide or fragment", "antigenic polypeptide or fragment" and "peptide" are used interchangeably and refer to chains of amino acids comprising between 2, or 3, or 4, or 5, or 6, or 7, or 8, or 9, or 10, or 11, or 12, or 13, or 14, or 15 and 10, or 11, or 12, or 13, or 14, or 15, or 20, or 25, or 30, or 35, or 40, or 45, or 50 or 55 or 60 or 100 or 150 or 200 or 300 or 350 or 400 or 500 amino acids. As used herein, the term "epitope" or "T cell epitope" refers to a sequence of contiguous amino acids contained within a protein antigen that possess a binding affinity to a T cell receptor when presented on the surface of antigen presenting cells. An epitope is antigen-specific but not individual specific. An epitope, a T cell epitope, a polypeptide, a fragment of a polypeptide or a composition comprising a polypeptide or a fragment thereof is "immunogenic" for a specific human individual if it is capable of inducing an immune cell response in that individual. In some embodiments, an "immune response", "T cell response" or "immunogenic response" are used interchangeably and may further include an antibody response. As used historically, the term "antigen" is used to designate an entity that is bound by an antigen-specific antibody or B-cell antigen receptor.

As used herein, the term "antigens", "proteins", "peptides", "polypeptides", "fragments", or "epitopes" may be used interchangeably. In particular, an "antigen" refers to a molecule containing one or more epitopes (either linear, conformational or both) that will stimulate a host's immune-system to make a humoral and/or cellular antigen-specific response. The term is used interchangeably with the term "immunogen". Further, antigenic polypeptide or fragment "derived from" a particular viral protein or protein domain refers to a full-length or near full-length viral protein or domain, as well as a fragment thereof, or a viral protein with internal deletions. Accordingly, the polypeptide may comprise the full-length sequence, fragments, truncated and partial sequences, as well as analogs and precursor forms of the reference molecule. In addition, the term "derived" may refer to construction of a peptide based on the knowledge of a representative protein domain sequence using any one of several suitable means, including, by way of example, isolation or synthesis. Thus, the term includes variations of the specified polypeptide.

In some embodiments, the antigenic peptides as described herein are 5 to 150 residues in length, e.g. 10 to 100 residues. The antigenic peptides may include consecutive or nonconsecutive sequences from the coronavirus viral domains.

The antigenic peptides described herein may comprise epitopes, i.e. amino acids that bind to an antibody generated in response to such sequence. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus, the term "epitope" encompasses sequences identical to the native sequence, as well as modifications to the native sequence, such as deletions, additions, and substitutions (generally conservative in nature).

As used herein, the term "conformational epitope" refers to a recombinant epitope having structural features native to the amino acid sequence encoding the epitope within the full-length natural protein. Native structural features include, but are not limited to, glycosylation and three-dimensional structure. The length of the epitope-defining sequence can be subject to wide variations as these epitopes are believed to be formed by the three-dimensional shape of the antigen (e.g., folding). Thus, amino acids defining the epitope can be relatively few in number, but widely dispersed along the length of the molecule (or even on different molecules in the case of dimers, etc.), being brought into correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g., cysteines involved in disulfide bonding, glycosylation sites, etc.).

As used herein, the term "Virus-Like Particle (VLP)" refers to molecules that closely resembles viruses but are lacking viral genetic materials. Use of VLPs derived from the Hepatitis B virus (HBV) and composed of the small HBV derived surface antigen (HBsAg) are well known in the art. A plurality of detailed VLP formation and release methods are described in U.S. Pat. Nos. 7,951,384 and 9,352,031, herein incorporated by reference. In some embodiments, the present invention includes VLP presenting S protein derived antigens on its surface. In other embodiments, the VLP displays S protein and M protein derived antigens. In other embodiments, the VLP displays two or more domains of S protein (i.e., HR1 and HR2 domains and the linker region between the HR1 and HR2 domains) and M protein derived antigens.

In order to increase the immunogenicity of the composition, in some embodiments, the immunogenic compositions comprise one or more adjuvants and/or cytokines. Suitable adjuvants include an aluminum salt such as aluminum hydroxide or aluminum phosphate, but may also be a salt of calcium, iron or zinc, or may be an insoluble suspension of acylated tyrosine, or acylated sugars, or may be cationically or anionically derivatized saccharides, polyphosphazenes, biodegradable microspheres, monophosphoryl lipid A (MPL), lipid A derivatives (e.g. of reduced toxicity), 3-O-deacylated MPL [3D-MPL], quil A, Saponin, QS21, Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides, bioadhesives and mucoadhesives, microparticles, liposomes, polyoxyethylene ether formulations, polyoxyethylene ester formulations, muramyl peptides or imidazoquinolone compounds (e.g. imiquamod and its homologues). Human immunomodulators suitable for use as adjuvants in the disclosure include cytokines such as interleukins (e.g. IL-1, IL-2, IL-4, IL-5, IL-6, IL-7, IL-12, etc), macrophage colony stimulating factor (M-CSF), tumor necrosis factor (TNF), granulocyte, macrophage colony stimulating factor (GM-CSF) may also be used as adjuvants.

In some embodiments, the compositions comprise an adjuvant selected from the group consisting of Montanide ISA-51 (Seppic, Inc., Fairfield, N.J., United States of America), QS-21 (Aquila Biopharmaceuticals, Inc., Lexington, Mass., United States of America), GM-CSF, cyclophosamide, *bacillus* Calmette-Guerin (BCG), corynbacterium *parvum*, levamisole, azimezone, isoprinisone, dinitrochlorobenezene (DNCB), keyhole limpet hemocyanins (KLH), Freunds adjuvant (complete and incomplete), mineral gels, aluminum hydroxide (Alum), lysolecithin, pluronic polyols, polyanions, oil emulsions, dinitrophenol, diphtheria toxin (DT). In some embodiments, the adjuvant is Montanide adjuvant. It is expected that an adjuvant or cytokine can be added in an amount of about 0.01 mg to about 10 mg per dose, preferably in an amount of about 0.2 mg to about 5 mg per dose. Alternatively, the adjuvant or cytokine may be at a concentration of about 0.01 to 50%, preferably at a concentration of about 2% to 30%.

In certain aspects, the immunogenic compositions of the disclosure are prepared by physically mixing the adjuvant and/or cytokine with peptides described herein under appropriate sterile conditions in accordance with known techniques to produce the final product. The dose may be determined according to various parameters, especially according to the substance used; the age, weight and condition of the individual to be treated; the route of administration; and the required regimen. The amount of antigen in each dose is selected as an amount which induces an immune response. A physician will be able to determine the required route of administration and dosage for any particular individual. The dose may be provided as a single dose or may be provided as multiple doses, for example taken at regular intervals, for example 2, 3 or 4 doses administered weekly. Typically, peptides, polynucleotides or oligonucleotides are typically administered in the range of 1 pg to 1 mg, more typically 1 pg to 10 μg for particle mediated delivery and 1 μg to 1 mg, and more typically 1-150 μg. Generally, it is expected that each dose will comprise 0.01-3 mg of antigen. An optimal amount for a particular vaccine can be ascertained by studies involving observation of immune responses in individuals.

In preferred embodiments, the immunogenic composition contains a SARS-CoV-2 antigen VLP. Alternatively, in other embodiments, HR1 and HR2 domains of S protein and/or M protein derived antigens may exist as nucleic acids and may be formulated as a DNA vaccine. In some embodiments, DNA vaccines, or gene vaccines, comprise a plasmid with a promoter and appropriate transcription and translation control elements and a nucleic acid sequence encoding one or more polypeptides of the disclosure. In some embodiments, the plasmids also include sequences to enhance, for example, expression levels, intracellular targeting, or proteasomal processing. In some embodiments, DNA vaccines comprise a viral vector containing a nucleic acid sequence encoding one or more polypeptides of the disclosure. In additional aspects, the compositions disclosed herein comprise one or more nucleic acids encoding peptides determined to have immunoreactivity with a biological sample. For example, in some embodiments, the compositions comprise one or more nucleotide sequences encoding 1, 2, 3, 4, 5, 6, 7, 8, 9, 10, 11, 12, 13, 14, 15, 16, 17, 18, 19, 20, or more peptides comprising a polypeptide or a fragment that is a fusion antigen derived from S protein and M protein of SARS-CoV-2 coronavirus. The DNA or gene vaccine also encodes immunomodulatory molecules to manipulate the resulting immune responses, such as enhancing the potency of the vaccine, stimulating the immune system or reducing immunosuppression. Strategies for enhancing the immunogenicity of DNA or gene vaccines include encoding of xenogeneic versions of antigens, fusion of antigens to molecules that activate T cells or trigger associative recognition, priming with DNA vectors followed by boosting with viral vector, and utilization of immunomodulatory molecules. In some embodiments, the DNA vaccine is introduced by a needle, a gene gun, an aerosol injector, with patches, via microneedles, by abrasion, among other forms. In some forms the DNA vaccine is incorporated into liposomes or other forms of nanobodies. In some embodiments, the DNA vaccine includes a delivery system selected from the group consisting of a transfection agent; protamine; a protamine liposome; a polysaccharide particle; a cationic nanoemulsion; a cationic polymer; a cationic polymer liposome; a cationic nanoparticle; a cationic lipid and cholesterol nanoparticle; a cationic lipid, cholesterol, and PEG nanoparticle; a dendrimer nanoparticle. In some embodiments, the DNA vaccines is administered by inhalation or ingestion. In some embodiments, the DNA vaccine is introduced into the blood, the thymus, the pancreas, the skin, the muscle, a tumor, or other sites.

In yet other embodiments, the composition may be prepared as an RNA vaccine. In some embodiments, the RNA is non-replicating mRNA or virally derived, self-amplifying RNA. In some embodiments, the non-replicating mRNA encodes the peptides disclosed herein and contains 5' and 3' untranslated regions (UTRs). In some embodiments, the virally derived, self-amplifying RNA encodes not only the peptides disclosed herein but also the viral replication machinery that enables intracellular RNA amplification and abundant protein expression. In some embodiments, the RNA is directly introduced into the individual. In some embodiments, the RNA is chemically synthesized or transcribed in vitro. In some embodiments, the mRNA is produced from a linear DNA template using a T7, a T3, or a Sp6 phage RNA polymerase, and the resulting product contains an open reading frame that encodes the peptides disclosed herein, flanking UTRs, a 5' cap, and a poly(A) tail. In some embodiments, various versions of 5' caps are added during or after the transcription reaction using a vaccinia virus capping enzyme or by incorporating synthetic cap or anti-reverse cap analogues. In some embodiments, an optimal length of the poly(A) tail is added to mRNA either directly from the encoding DNA template or by using poly(A) polymerase. In some embodiments, the fragments are derived from an antigen that is expressed within the sequence of S and/or M proteins of SARS-CoV-2. In some embodiments, the RNA includes signals to enhance stability and translation. In some embodiments, the RNA also includes unnatural nucleotides to increase the half-life or modified nucleosides to change the immunostimulatory profile.

In some embodiments, the RNA is introduced by a needle, a gene gun, an aerosol injector, with patches, via microneedles, by abrasion, among other forms. In some forms the RNA vaccine is incorporated into liposomes or other forms of nanobodies that facilitate cellular uptake of RNA and protect it from degradation. In some embodiments, the RNA vaccine includes a delivery system selected from the group consisting of a transfection agent; protamine; a protamine liposome; a polysaccharide particle; a cationic nanoemulsion; a cationic polymer; a cationic polymer liposome; a cationic nanoparticle; a cationic lipid and cholesterol nanoparticle; a cationic lipid, cholesterol, and PEG nanoparticle; a dendrimer nanoparticle; and/or naked mRNA; naked mRNA with in vivo electroporation; protamine-complexed mRNA; mRNA associated with a positively charged oil-in-water cationic nanoemulsion; mRNA associated with a chemically modified dendrimer and complexed with polyethylene glycol (PEG)-lipid; protamine-complexed mRNA in a PEG-lipid nanoparticle; mRNA associated with a cationic polymer such as polyethylenimine (PEI); mRNA associated with a cationic polymer such as PEI and a lipid component; mRNA associated with a polysaccharide (for example, chitosan) particle or gel; mRNA in a cationic lipid nanoparticle (for example, 1,2 dioleoyloxy 3 trimethylammoniumpropane (DOTAP) or dioleoylphosphatidylethanolamine (DOPE) lipids); mRNA complexed with cationic lipids and cholesterol; or mRNA complexed with cationic lipids, cholesterol and PEG-lipid. In some embodiments, the RNA vaccine is administered by inhalation or ingestion. In some embodiments, the RNA is introduced into the blood, the thymus, the pancreas, the skin, the muscle, a tumor, or other sites, and/or by an intradermal, intramuscular, subcutaneous, intranasal, intranodal, intravenous, intrasplenic, intratumoral or other delivery route.

In some embodiments, the polynucleotide or oligonucleotide components are naked nucleotide sequences or be in combination with cationic lipids, polymers or targeting systems. They may be delivered by any available technique. For example, the polynucleotide or oligonucleotide may be introduced by needle injection, preferably intradermally, subcutaneously or intramuscularly. Alternatively, the polynucleotide or oligonucleotide may be delivered directly across the skin using a delivery device such as particle-mediated gene delivery. The polynucleotide or oligonucleotide may be administered topically to the skin, or to mucosal surfaces for example by intranasal, oral, or intrarectal administration. Uptake of polynucleotide or oligonucleotide constructs may be enhanced by several known transfection techniques, for example those including the use of transfection agents. Examples of these agents include cationic agents, for example, calcium phosphate and DEAE-Dextran and lipofectants, for example, lipofectam and transfectam. The dosage of the polynucleotide or oligonucleotide to be administered can be altered.

The immunogenic compositions or vaccines described herein comprise, in addition to one or more peptides, nucleic acids or vectors, a pharmaceutically acceptable excipient, carrier, diluent, buffer, stabilizer, preservative, adjuvant or other materials well known to those skilled in the art. Such materials are preferably non-toxic and preferably do not interfere with the pharmaceutical activity of the active ingredient(s). The pharmaceutical carrier or diluent may be, for example, water containing solutions. The precise nature of the carrier or other material may depend on the route of administration, e.g., oral, intravenous, cutaneous or subcutaneous, nasal, intramuscular, intradermal, and intraperitoneal routes. In some embodiments, the pharmaceutical compositions of the disclosure comprise one or more "pharmaceutically acceptable carriers". These are typically large, slowly metabolized macromolecules such as proteins, saccharides, polylactic acids, polyglycolic acids, polymeric amino acids, amino acid copolymers, sucrose (Paoletti et. al., 2001, Vaccine, 19:2118-2126), trehalose (WO 00/56365), lactose and lipid aggregates (such as oil droplets or liposomes). Such carriers are well known to those of ordinary skill in the art. In some embodiments, the pharmaceutical compositions contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier (Gennaro et. al., 2000, Remington: The Science and Practice of Pharmacy, 20th edition, ISBN:0683306472).

In some embodiments, the immunogenic compositions of the disclosure are lyophilized or in aqueous form, i.e., solutions or suspensions. Liquid formulations of this type allow the compositions to be administered direct from their packaged form, without the need for reconstitution in an aqueous medium, and are thus ideal for injection. In some embodiments, the immunogenic compositions are presented in vials, or they may be presented in ready filled syringes. The syringes may be supplied with or without needles. A syringe will include a single dose, whereas a vial may include a single dose or multiple doses. Liquid formulations of the disclosure are also suitable for reconstituting other medicaments from a lyophilized form. Where a immunogenic composition is to be used for such extemporaneous reconstitution, the disclosure provides a kit, which may comprise two vials, or may comprise one ready-filled syringe and one vial, with the contents of the syringe being used to reconstitute the contents of the vial prior to injection.

In some embodiments, the immunogenic compositions of the disclosure include an antimicrobial, particularly when packaged in a multiple dose format. Antimicrobials may be used, such as 2-phenoxyethanol or parabens (methyl, ethyl, propyl parabens). Any preservative is preferably present at low levels. Preservative may be added exogenously and/or may be a component of the bulk antigens which are mixed to form the composition (e.g., present as a preservative in pertussis antigens).

In some embodiments, the immunogenic compositions of the disclosure comprise detergent e.g., Tween (polysorbate), DMSO (dimethyl sulfoxide), DMF (dimethylformamide). Detergents are generally present at low levels, e.g., <0.01%, but may also be used at higher levels, e.g., 0.01-50%. In some embodiments, the immunogenic compositions of the disclosure include sodium salts (e.g., sodium chloride) and free phosphate ions in solution (e.g., by the use of a phosphate buffer).

In some embodiments, the immunogenic compositions are encapsulated in a suitable vehicle either to deliver the peptides into antigen presenting cells or to increase the stability. As will be appreciated by a skilled artisan, a variety of vehicles are suitable for delivering a immunogenic composition of the disclosure. Non-limiting examples of suitable structured fluid delivery systems may include nanoparticles, liposomes, microemulsions, micelles, dendrimers and other phospholipid-containing systems. Methods of incorporating immunogenic compositions into delivery vehicles are known in the art.

Other aspects of the present invention relate to methods of inducing an immune response to at least one coronavirus polypeptide or fragment antigen as described above in a subject in need thereof, comprising the steps of: administering to the subject an effective amount of the immunogenic composition of antigenic polypeptide or fragments derived from coronavirus S protein, coronavirus M protein or combinations thereof; allowing a suitable period of time to elapse; and optionally administering at least one additional dose of the immunogenic composition. A "suitable period of time" is defined herein as a sufficient time for a subject to produce antibodies against the administered antigens described herein. A sufficient time for a subject to acquire ability to produce antibodies may be days (e.g., 2, 3, 4, 5, 6 or 7 days), weeks (e.g., 1, 2, 3 or 4 weeks), months (e.g., 1, 2, 3, 4, 5, or 6 months), or years (e.g. 1, 2, 3, 4, or 5 years) after a first, second or third dose of the immunogenic composition is administered.

As used herein, the term "effective amount" refers to an amount of VLPs necessary or sufficient to realize a desired biologic effect. An effective amount of the composition would be the amount that achieves a selected result, and such an amount could be determined as a matter of routine experimentation by a person skilled in the art. For example, an effective amount for preventing, treating and/or ameliorating an infection could be that amount necessary to cause activation of the immune system, resulting in the development of an antigen specific immune response upon exposure to VLPs of the invention. The term is also synonymous with "sufficient amount" or "therapeutically effective amount".

In some embodiments, the coronavirus polypeptide or fragment antigen has a sequence identity selected from the group consisting of SEQ ID NOs:1 to 166.

In some embodiments, the method of treatment comprises administration to an individual of more than one peptide, polynucleic acid in a VLP or vector. These may be administered together/simultaneously and/or at different times or sequentially. The use of combinations of different peptides, optionally targeting different antigens, may be important to overcome the challenges of viral or individual heterogeneity. The use of peptides of the disclosure in combination expands the group of individuals who can experience clinical benefit from vaccination. Multiple immunogenic compositions, manufactured for use in one regimen, may define a drug product. In some cases, different peptides, polynucleic acids or vectors of a single treatment may be administered to the individual within a period of, for example, 1 year, or 6 months, or 3 months, or 60 or 50 or 40 or 30 days.

Preferably, the sequence employed to form the VLP immunogenic composition exhibits between about 60-80% sequence identity to a naturally occurring coronavirus polynucleotide or polypeptide sequence or conformational epitope sequence and more preferably the sequences exhibit between about 80-100% sequence identity, e.g., at least about 85%, 90%, 95%, 96%, 97%, 98%, or 99% sequence identity to a naturally occurring polynucleotide or polypeptide sequence or a sequence as disclosed herein. In addition, the sequences described herein can be operably linked to each other in any combinations. For example, one or more sequences may be expressed from the same promoter and/or from different promoters.

Routes of administration include but are not limited to ocular, intranasal, oral, subcutaneous, intradermal, and intramuscular. The subcutaneous administration is particularly preferred. Subcutaneous administration may for example be by injection into the abdomen, lateral and anterior aspects of upper arm or thigh, scapular area of back, or upper ventrodorsal gluteal area. In some embodiments, the compositions of the disclosure are administered in one, or more doses, as well as, by other routes of administration. For example, such other routes include, intracutaneously, intravenously, intravascularly, intraarterially, intraperitnoeally, intrathecally, intratracheally, intracardially, intralobally, intramedullarly, intrapulmonarily, and intravaginally. Depending on the desired duration of the treatment, the compositions according to the disclosure may be administered once or several times, also intermittently, for instance on a monthly basis for several months or years and in different dosages. Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

In some embodiments, the compositions of the disclosure are administered, or the methods and uses for treatment according to the disclosure are performed, alone or in combination with other pharmacological compositions or treatments, for example other immunotherapy, vaccine or anti-viral. In some embodiments, the other therapeutic compositions or treatments are administered either simultaneously or sequentially with (before or after) the composition(s) or treatment of the disclosure.

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope of the present invention.

Example 1

The primary objective of designing a safer vaccine against SARS-CoV-2 using a rational approach is to minimize the possibility of inducing ADE upon vaccination, to reduce or eliminate off target penetration of the virus into immune cells and to prevent endothelial damage and thereby minimize the risk of vascular dysfunction in infected patients. A secondary objective is to create a stable formulation and affordable manufacture of the vaccine by using appropriate adjuvants and vaccine stabilization techniques.

Figure 2:
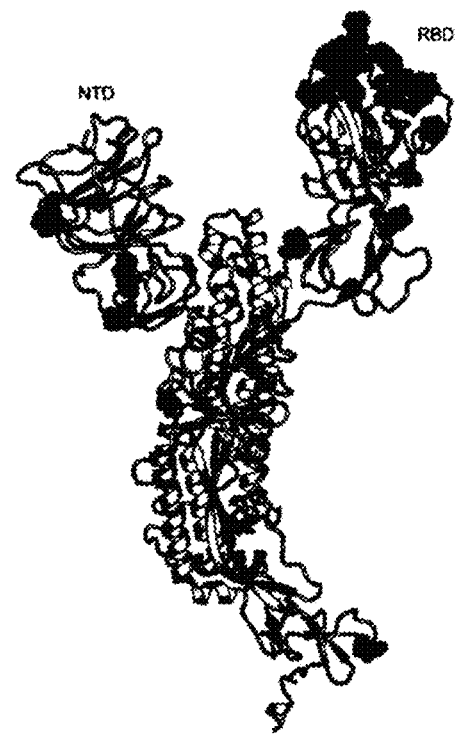
FIG. 2 shows a sequence variability within N-terminal domains of SARS-CoV-2 S protein.
Figure 4A:
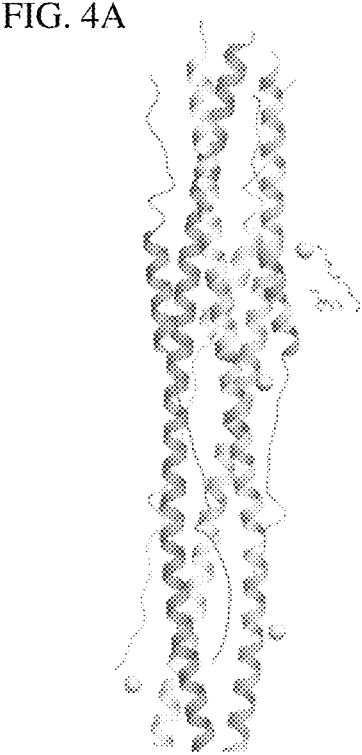
FIG. 4A-B show a 6-helix bundle fusion complex formed between HR1 and HR2, front view (A) and top view (B). The long HR1 helixes are packed in the interior of the bundle whereas the short HR2 helices are located on the exterior.
Figure 4B:
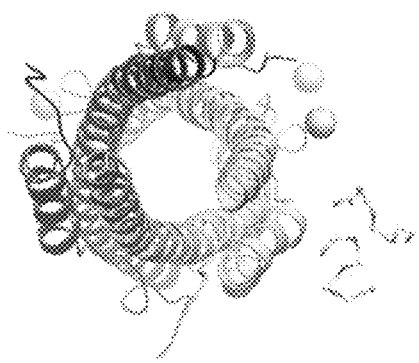
Figure 5A:
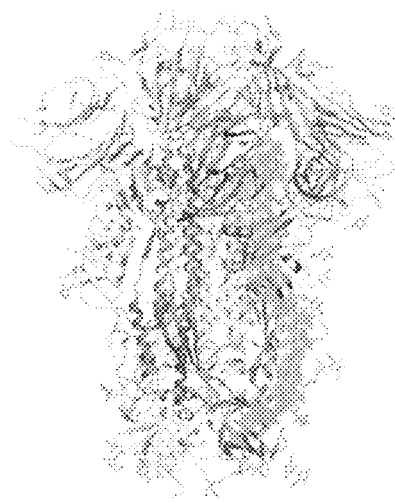
FIG. 5A-D show a composition of the proposed antigens SC2SHR1 (A), SC2HSHRL (B), SC2HSHR2 (C) and SC2HSHR2L (D) in the cases where high-resolution structures of S or M protein are available. 6VXX.PDB, 6LXT.PDB and 6M3W.PDB are shown in the figure.
Figure 5B:
Figure 5C:
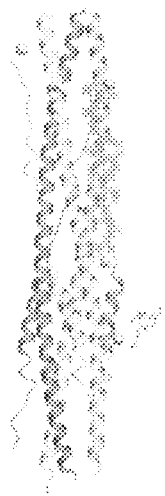
Figure 5D:

The receptor binding domain (RBD) in the spike protein is the most variable part of the virus genome (Anderson et. al., 2020). Blue spheres in FIG. 2 depict the variability of the RBD as well as the N-terminal domain (NTD) of S protein monomer based on sequence analysis of approximately 60 clinical isolates (Wrapp et. al., 2020). This RBD variability is thought to allows SARS-CoV-2 gain antigen drift, thereby permitting immune escape, while still allowing high-affinity binding to ACE2 receptor (Yang et. al., 2005). Surprisingly, convalescent plasma of COVID-19 patients who recovered without hospitalization do not contain high levels of neutralizing antibodies against RBD (Robbiani et. al., 2020). As discussed above, should variability in regions of S protein produce non-neutralizing or sub-neutralizing antibodies, that might prove detrimental through induction of ADE.

In contrast, the C-terminal region of the S protein is relatively conserved, not only among distinct SARS-CoV-2 strains isolated till date, but also across other members of the sarbecovirus family members as shown below (FIG. 3, Wec et. al., 2020). The SARS-CoV-2 HR1 domain (aa 908-986) has 7 amino acids different with SARS-CoV-1 or bat coronavirus RaTG13, while HR2 (aa 1107-1175) is 100% identical at amino acid level between the three. The CH domain (aa 986-1035) is also 100% conserved whereas the CD domain (aa 1076-1141) has 9 amino acid changes against the SARS-CoV-1 or bat coronavirus RaTG1 sequences (Ceraolo et. al., 2020).

The S protein is activated by proteolytic cleavage at two sites, S1/S2 and S2' (FIG. 1) by both TMPRSS2 as well as the proprotein convertase, furin (Bestle et. al., 2020; Shang et. al., 2020). The S1 subunit contains the RBD while the S2 subunit contains the hydrophobic heptad repeats HR1 and HR2 that are essential for membrane fusion. Once the RBD binds to the ACE2 receptor on target cells, the HR1 and HR2 domains interact with one another forming a six-helix bundle complex. The connector domain between HR1 and HR2 forms a loop inducing a conformational change that allows the fusion peptide on the virus insert into the target cell membrane causing virus-cell fusion.

Membrane protein (M) is a type III transmembrane glycoprotein and is the most abundant protein in SARS-CoV-2. The M protein has a short amino terminus domain located outside the virus, three transmembrane domains and a carboxy terminus domain located inside the viral envelope. On the viral surface, M protein is juxtaposed alongside the S protein and plays a role in the budding process (Alsaadi et. al., 2019). In alpha coronavirus, the M protein has been shown to participate in viral entry into host cells by facilitating membrane fusion (Naskalska et. al., 2019). While the M protein is highly conserved within SARS-CoV-2 family, there is sequence heterogeneity at the N-terminus of the protein where an insertion of a serine residue is unique to SARS-CoV-2 compared to bat or pangolin homologs (Bianchi et. al., 2020). Such mutations at the amino terminus region of the M protein could probably play a role in the host cell interactions.

One aim of the present disclosure is to prevent viral fusion with cell membrane by targeting a vaccine immune response against conserved C-terminal membrane-proximal fragments of SARS-CoV-2, specifically the HR1 and HR2 regions and the spacer in between.

Such a targeted approach has several advantages. First, by limiting the exposure of the host immune system, unwanted antibodies against undesirable regions of the S protein are eliminated. This in turn proves advantageous since virus bound, non-neutralizing antibodies cannot be taken up in immune effector cells such as macrophages, dendritic cells and T-cells, thereby diminishing the possibility of unwanted cytokine production and immunopathology. Second, by presenting short, rationally designed antigens to block viral fusion, the off-target entry of virus into immune cells or vascular endothelial cells can be prevented. Third, simple antigens lend themselves to simpler, cost-effective production with the possibility of easier scale up but without the need of BSL3 manufacturing and testing facilities, thereby lowering cost of goods. Fourth, antigen design will allow facile use of established adjuvants such as alum to skew host response away from a Th2 type which is linked to eosinophil-derived immunopathology (Chen et. al., 2020). The simpler, rationally designed antigens will be possessing a much better shelf life, enabling easy storage and distribution of vaccine with the need of complex logistics that are poorly available in low-income countries.

Human antibodies isolated from transgenic mice against the SARS-CoV-1 S2 domain have been shown to successfully neutralize pseudo-typed viruses expressing different S proteins of various clinical isolates on SARS-CoV-1 in an RBD-independent manner (Elshabrawy et. al., 2012). In addition, monoclonal antibodies raised against SARS-CoV-1 S protein were found to neutralize viral infection by inhibiting virus entry into Vero E6 cells, a mechanism distinct from virus-ACE2 receptor binding blockade, demonstrating the feasibility of preventing viral fusion as a viable vaccine strategy (Lai et. al., 2005, Lip et. al., 2006). Similarly, anti-M protein monoclonal antibodies have been identified from lymphocytes of convalescent patients infected with SARS-CoV-1 that potently neutralize viral entry into Vero-E6 cells (Liang et. al., 2005). In addition, sera from SARS-CoV-1 have been shown to bind both amino as well as carboxy terminus of M protein (Hu et. al., 2003; Vob et. al., 2009).

Example 2

Antigen Design

One of the important aspects of the antigen design is to represent the prefusion state for the S protein. This is because conversion of the S protein to post-fusion state involves a significant conformational change wherein the HR1 and HR2 domains pack against one another to form an anti-parallel six-helix bundle. This rearrangement triggers fusion of the viral membrane with the host cell. Thus, the rational design strategy is to block the virus in the prefusion state and prevent conversion into the post fusion state. In such a case, the viral entry and spread can be stopped irrespective of the cell the virus infects. Indeed, it has been shown that the SARS-CoV-1 HR2 domain forms a coiled coil structure in solution consisting of three helices folded as a parallel trimer, as in prefusion state (Hakkanson et. al., 2006). Thus, even targeting HR2 as a standalone antigen may be possible.

Seven distinct antigens were designed based on M protein and the heptad repeat structure within the prefusion SARS-CoV-2 S protein as follows:

SC2MN1: Amino acids 1-31 covering amino terminus of M protein

SC2MC1: Amino acids 130-160 from carboxy terminus of M protein

SC2SHR1: Amino acids 913-984 covering the first heptad repeat HR1 of S protein

SC2HSHRL: Amino acids 1147-1170 covering the linker region connecting HR1 and HR2

SC2HSHR2: Amino acids 1171-1212 covering the second heptad repeat HR2 of S protein SC2HSHR2L: Amino acids 1147-1212 covering both the linker as well as HR2 regions SC2RBD (control antigen): Amino acids 318-541 representing RBD of S protein In reference to FIG. 2, the composition of the proposed antigens in those cases where high-resolution structures of S or M protein are available (6VXX.PDB, 6LXT.PDB, 6M3W.PDB). These antigens were created in the form of fusion protein expressed on virus like particles (VLP) using the Hepatitis B surface antigen S protein HBV-S. Presenting viral antigens on VLPs will result in enhanced quality of host immune response because VLPs can present antigen in draining lymph nodes and efficiently engage B cell receptors due to their repetitive structure resulting in a higher abundance of neutralizing antibodies (Coleman et. al., 2014). The HBV-S core protein is a very well-established system for VLP generation (Martini et. al., 2019).

A widely used approach for presenting antigens on VLPs is through the use of genetic fusion. However, while this technique can result in virus-like configuration of the antigen, longer peptides or those with charge or significant hydrophobicity can interfere with the actual assembly of the VLPs. To circumvent this problem, a mosaic approach was undertaken to construct VLPs (Ramasamy et. al., 2018). Specifically, the HBV S protein was coexpressed with proposed antigens in a fixed stoichiometry. In some embodiments, the ratio of HBV S protein to a SARS-CoV-2 polypeptide may be 6:1, preferably 5:1, more preferably 4:1. Microscopic as well as immunological assessment were carried out to ensure bona fide VLP formation. Because the HR1, linker and HR2 regions are conserved between SARS CoV-1 and SAR-CoV-2, monoclonal antibodies previously made using SARS-CoV-1 were used as analytical and immunological tools to ensure proper VLP assembly. Each of the antigens will be produced and tested, in vitro and in vivo.

Example 3

Production of Immunogens

VLPs contained within formulations of approved vaccines such as those against human papillomavirus (HPV) or hepatitis B virus (HBV) are produced in yeast cells. These vaccines have proven to be safe and effective, and their manufacturing processes are very well established. Separately, VLPs expressed in recombinant baculovirus systems covering multi-component antigens such as HA and matrix 1 for influenza vaccine have also been established. The antigens proposed in our strategy are glycosylated at multiple sites and it becomes important to ensure glycosylation in antigen preparation as close to the human system as possible (Wu et. al., 2010). Therefore, immunogen production in Vero cells is proposed (Ammerman et. al., 2008).

Vero cells are derived from African green monkeys and are a close approximation to human cells. Vero cell lines have been approved in the US for production of licensed viral vaccines such as those against rotavirus, smallpox and inactivated poliovirus. Worldwide, Vero cells have also been used for the production of vaccines against Rabies virus, Reovirus and Japanese encephalitis virus. Commercially, Vero cells have been scaled up to 660 m2 with cell density approaching 2.3×105 cells/cm3. As such Vero cell technology, is cheap, scalable and well-established vaccine production technology worldwide.

Example 4

Epitope Prediction for SARS-CoV-2 M and S Antigens
1: M protein (UniProt: P59596)
The results presented below for T cell epitopes (Table 1) are derived from experimental data deposited at the IEDB ImmunoBrowser (Vita et al., 2014). Due to the unavailability of a structure for the M protein, a sequence-based algorithm for B cell epitope prediction was used (BepiPred 2.0, Table 2; Jespersen et al., 2017).

TABLE 1

T cell epitope prediction for the N (top) and C terminus (bottom) of SARS-CoV-2 M protein based on experimental data available at the IEDB. Epitopes tested immediately downstream or upstream of these sequences did not give positive responses.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
| 1 | MADNGTITVEELKQL | 1 | 15 | 4 | 1 | 1 | 1 | 0.25 |
| 2 | MADNGTITVEELKQLL | 1 | 16 | 40 | 10 | 1 | 0 | 0.25 |
| 3 | MADNGTITVEELKQLLEQ | 1 | 18 | 1 | 1 | 1 | 0 | 1 |
| 4 | MADNGTITVEELKQLLEQWN | 1 | 20 | 32 | 1 | 1 | 1 | 0.03 |
| 5 | MADNGTITVEELKQLLEQWNLVIGFLFLAWI | 1 | 31 | 40 | 40 | 1 | 0 | 1 |
| 6 | ITVEELKQ | 7 | 14 | 4 | 3 | 1 | 0 | 0.75 |
| 7 | ITVEELKQLLEQWNLVI | 7 | 23 | 40 | 28 | 1 | 0 | 0.7 |
| 8 | KLNTDHAGSNDNIALLVQ | 204 | 221 | 1 | 1 | 1 | 0 | 1 |
| 9 | TDHAGSNDNIALLVQ | 207 | 221 | 48 | 27 | 1 | 1 | 0.56 |

Sequence-Based B Cell Epitope Prediction Using the BepiPred 2.0 Server

TABLE 2

B cell epitope prediction for the N (left) and C terminus (center, right) of SARS-CoV-2M protein based on the BepiPred algorithm, a server for sequence-based epitope prediction (cbs.dtu.dk/services/BepiPred/). Residues immediately downstream or upstream of these were not identified as predicted epitopes (default threshold of 0.5).

| Position | AminoAcid | Exposed/Buried | EpitopeProbability |
|---|---|---|---|
| 5 | G | E | 0.501 |
| 6 | T | E | 0.522 |
| 7 | I | B | 0.535 |
| 8 | T | E | 0.524 |
| 9 | V | B | 0.531 |
| 10 | E | E | 0.539 |
| 11 | E | E | 0.538 |
| 12 | L | B | 0.518 |
| 13 | K | B | 0.519 |
| 14 | Q | E | 0.541 |
| 15 | L | B | 0.541 |
| 16 | L | B | 0.530 |
| 17 | E | E | 0.540 |
| 18 | Q | E | 0.521 |
| 180 | L | B | 0.519 |

TABLE 2-continued

B cell epitope prediction for the N (left) and C terminus (center, right) of SARS-CoV-2M protein based on the BepiPred algorithm, a server for sequence-based epitope prediction (cbs.dtu.dk/services/BepiPred/). Residues immediately downstream or upstream of these were not identified as predicted epitopes (default threshold of 0.5).

| Position | AminoAcid | Exposed/Buried | EpitopeProbability |
|---|---|---|---|
| 181 | G | E | 0.530 |
| 182 | A | E | 0.549 |
| 183 | S | E | 0.572 |
| 184 | Q | E | 0.587 |
| 185 | R | E | 0.595 |
| 186 | V | B | 0.600 |
| 187 | G | E | 0.598 |
| 188 | T | E | 0.576 |
| 189 | D | E | 0.555 |
| 190 | S | B | 0.540 |
| 191 | G | B | 0.522 |
| 192 | F | B | 0.501 |
| 195 | Y | B | 0.505 |
| 196 | N | B | 0.509 |
| 197 | R | B | 0.531 |
| 198 | Y | E | 0.549 |
| 199 | R | E | 0.560 |
| 200 | I | B | 0.571 |
| 201 | G | E | 0.567 |
| 202 | N | E | 0.564 |
| 203 | Y | B | 0.563 |
| 204 | K | E | 0.563 |
| 205 | L | B | 0.580 |
| 206 | N | E | 0.594 |
| 207 | T | B | 0.606 |
| 208 | D | E | 0.613 |
| 209 | H | E | 0.621 |
| 210 | A | E | 0.630 |
| 211 | G | E | 0.636 |
| 212 | S | E | 0.626 |
| 213 | N | E | 0.617 |
| 214 | D | E | 0.594 |
| 215 | N | E | 0.568 |
| 216 | I | B | 0.538 |
| 217 | A | E | 0.506 |

2: S Protein (UniProt: P59594)

The results presented below for T cell epitopes (Tables 3 and 5) are derived from experimental data available at the IEDB ImmunoBrowser (Vita et al., 2014). Structure-based B cell epitope predictions (Tables 4 and 6) were generated with SEPPA 3.0 (Zhou et al., 2019). Table 7 shows a sequence-based epitope prediction using BepiPred 2.0 (Jespersen et al., 2017) for amino acids 1104-1184 as the structures available did not span that region.

TABLE 3

T cell epitope prediction for the receptor binding domain of SARS-CoV-1 S protein (residues 306-527) with peptides spanning the receptor-binding motif (424-494) highlighted in blue. Response frequency is based on experimental data available at the IEDB. Tested epitopes that did not give positive responses are absent.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
| 10 | EIDKGIYQTSNFRVVPS | 294 | 310 | 42 | 21 | 1 | 0 | 0.5 |
| 11 | KGIYQTSNFRVVPSGDVVRF | 297 | 316 | 1 | 1 | 1 | 0 | 1 |
| 12 | KGIYQTSN | 297 | 304 | 4 | 2 | 1 | 0 | 0.5 |
| 13 | IYQTSNFRVVPSGDVVRF | 299 | 316 | 3 | 1 | 1 | 2 | 0.33 |
| 14 | TSNFRVVPSGDVVRFPN | 302 | 318 | 42 | 20 | 1 | 0 | 0.48 |
| 15 | SGDVVRFPNITNLCPFG | 310 | 326 | 42 | 13 | 1 | 0 | 0.31 |
| 16 | VRFPNITNLCPFGEVFN | 314 | 330 | 42 | 10 | 1 | 0 | 0.24 |
| 17 | LCPFGEVFNATKFPSVY | 322 | 338 | 42 | 11 | 1 | 0 | 0.26 |
| 18 | FGEVFNAT | 325 | 332 | 4 | 2 | 1 | 0 | 0.5 |
| 19 | FNATKFPSVYAWERKKI | 329 | 345 | 3 | 2 | 1 | 0 | 0.67 |
|  | N330, A331, T332, K333, F360, W423, N424, N427, I428, A430, | 330 | 485 | 1 | 1 | 1 | 0 | 1 |

TABLE 3-continued

T cell epitope prediction for the receptor binding domain of SARS-CoV-1 S protein
(residues 306-527) with peptides spanning the receptor-binding motif (424-494) highlighted in
blue. Response frequency is based on experimental data available at the IEDB. Tested epitopes
that did not give positive responses are absent.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
| | T431, S432, N435, N437, T485 | | | | | | | |
| 20 | TKFPSVYAWERKKISNCVAD | 332 | 351 | 1 | 1 | 1 | 0 | 1 |
| 21 | PSVYAWERKKISNCVAD | 335 | 351 | 42 | 12 | 1 | 0 | 0.29 |
| 22 | SVYAWERKKISNCVADY | 336 | 352 | 3 | 1 | 1 | 2 | 0.33 |
| 23 | VYAWERKKISNCVADYSVLYNSTF | 337 | 360 | 1 | 1 | 1 | 0 | 1 |
| | K343, K344, I345, S346, N347, C348, V349, A350, D351, Y352, S353, V354, L355, Y356, N357, S358, T359, F360, F361, S362, T363, F364, K365, C366, Y367, K373, L374, N375, D376, L377, C378, F379, S380, N381, V382, Y383, A384, D385, S386, F387, V388, V389, K390, K411, L412, P413, D414, D415, F416, M417, G418, C419, V420, L421, A422, W423, N424, T425, R426, N427, I428 | 343 | 428 | 1 | 1 | 1 | 0 | 1 |
| 24 | KKISNCVADYSVLYNSTF | 343 | 360 | 5 | 1 | 1 | 2 | 0.2 |
| 25 | KKISNCVADYSVLYNST | 343 | 359 | 42 | 5 | 1 | 0 | 0.12 |
| | K344, F360, Y442, L472, D480, T487 | 344 | 487 | 1 | 1 | 1 | 0 | 1 |
| 26 | CVADYSVLY | 348 | 356 | 11 | 3 | 2 | 0 | 0.27 |
| 27 | YSVLYNSTFFSTFKCYG | 352 | 368 | 42 | 12 | 1 | 0 | 0.29 |
| | Y356, N357, S358, T359, F361, S362, T363, F364, K365, C366, A371, T372, G391, R395, N424, I489, Y494 | 356 | 494 | 1 | 1 | 1 | 0 | 1 |

TABLE 3-continued

T cell epitope prediction for the receptor binding domain of SARS-CoV-1 S protein (residues 306-527) with peptides spanning the receptor-binding motif (424-494) highlighted in blue. Response frequency is based on experimental data available at the IEDB. Tested epitopes that did not give positive responses are absent.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
|  | Y356, N357, S362, T363, F364, K365, C366, Y367, G368, V369, S370, A371, T372, K373, D376, L377, R395, D415, M417 | 356 | 417 | 1 | 1 | 1 | 0 | 1 |
| 28 | STFFSTFKCYGVSATKL | 358 | 374 | 4 | 2 | 2 | 2 | 0.5 |
|  | T359, S362, G391, D392, N424, R426, N427, T486, T487, G488, I489, G490, Y491, Q492, Y494 | 359 | 494 | 1 | 1 | 1 | 0 | 1 |
|  | T359, T363, K365, K390, G391, D392, R395, R426, Y436, G482, Y484, T485, T486, T487, G488, I489, G490, Y491, Q492, Y494 | 359 | 494 | 2 | 1 | 1 | 1 | 0.5 |
| 29 | FFSTFKCYGVSATKLND | 360 | 376 | 42 | 5 | 1 | 0 | 0.12 |
| 30 | KCYGVSATKL | 365 | 374 | 4 | 3 | 3 | 1 | 0.75 |
| 31 | CYGVSATKL | 366 | 374 | 3 | 3 | 3 | 0 | 1 |
| 32 | CYGVSATKLNDLCFSNV | 366 | 382 | 42 | 13 | 1 | 0 | 0.31 |
| 33 | YGVSATKL | 367 | 374 | 1 | 1 | 1 | 0 | 1 |
| 34 | KLNDLCFSNVYADSFVV | 373 | 389 | 42 | 8 | 1 | 0 | 0.19 |
| 35 | SNVYADSFVVKGDDVRQIAP | 380 | 399 | 1 | 1 | 1 | 0 | 1 |
| 36 | NVYADSFVVKGDDVRQI | 381 | 397 | 43 | 13 | 1 | 1 | 0.3 |
|  | D392, V394 | 392 | 394 | 1 | 1 | 1 | 0 | 1 |
|  | D392, V394, D414, F416, R441, D454 | 392 | 454 | 1 | 1 | 1 | 0 | 1 |
| 37 | IAPGQTGVIADYNYKLP | 397 | 413 | 42 | 10 | 1 | 0 | 0.24 |
| 38 | IADYNYKLPDDFMGCVL | 405 | 421 | 42 | 5 | 1 | 0 | 0.12 |
| 39 | KLPDDFMGCVLAWNTRN | 411 | 427 | 42 | 9 | 1 | 0 | 0.21 |
| 40 | KLPDDFMGCV | 411 | 420 | 20 | 4 | 1 | 1 | 0.2 |

TABLE 3-continued

T cell epitope prediction for the receptor binding domain of SARS-CoV-1 S protein (residues 306-527) with peptides spanning the receptor-binding motif (424-494) highlighted in blue. Response frequency is based on experimental data available at the IEDB. Tested epitopes that did not give positive responses are absent.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
| 41 | CVLAWNTRNIDATSTGN | 419 | 435 | 42 | 8 | 1 | 0 | 0.19 |
| 42 | NTRNIDATSTGN | 424 | 435 | 8 | 8 | 1 | 0 | 1 |
|  | R426, S432, T433, Y436, N437, K439, Y440, Y442, P469, P470, A471, L472, N473, C474, Y475, W476, L478, N479, D480, Y481, G482, Y484, T485, T486, T487, G488, I489, Y491, Q492 | 426 | 492 | 1 | 1 | 1 | 0 | 1 |
| 43 | NIDATSTGNYNYKYRYLR | 427 | 444 | 3 | 1 | 1 | 2 | 0.33 |
| 44 | NIDATSTGNYNYKYRYL | 427 | 443 | 42 | 11 | 1 | 0 | 0.26 |
|  | I428, A430, K439 | 428 | 439 | 1 | 1 | 1 | 0 | 1 |
|  | D429, R441, D454 | 429 | 454 | 1 | 1 | 1 | 0 | 1 |
|  | D429, R441, E452, D454 | 429 | 454 | 1 | 1 | 1 | 0 | 1 |
|  | D429, R441, D454 | 429 | 454 | 1 | 1 | 1 | 0 | 1 |
|  | D429, R441, D454, D463 | 429 | 463 | 1 | 1 | 1 | 0 | 1 |
|  | D429, R441, E452, D454 | 429 | 454 | 1 | 1 | 1 | 0 | 1 |
|  | T431, S432, K439, G446 | 431 | 446 | 1 | 1 | 1 | 0 | 1 |
| 45 | TSTGNYNYKYRYLRH | 431 | 445 | 4 | 1 | 1 | 1 | 0.25 |
| 46 | GNYNYKYRYLRHGKL | 434 | 448 | 1 | 1 | 1 | 0 | 1 |
| 47 | GNYNYKYRYLRHGKLRPFER | 434 | 453 | 1 | 1 | 1 | 0 | 1 |
| 48 | NYNYKYRYLR | 435 | 444 | 3 | 2 | 2 | 1 | 0.67 |
| 49 | NYNYKYRYLRHGKLRPF | 435 | 451 | 46 | 12 | 3 | 2 | 0.26 |
| 50 | YNYKYRYL | 436 | 443 | 2 | 2 | 2 | 0 | 1 |
| 51 | YNYKYRYLRHGKLRPFERDI | 436 | 455 | 1 | 1 | 1 | 0 | 1 |
| 52 | HNYKYRYL | 436 | 443 | 18 | 12 | 3 | 0 | 0.67 |
| 53 | YNYKYRYLRHGKLRP | 436 | 450 | 4 | 1 | 1 | 1 | 0.25 |
| 54 | NYKYRYLRHGKLRPFERDISNVP | 437 | 459 | 1 | 1 | 1 | 0 | 1 |

TABLE 3-continued

T cell epitope prediction for the receptor binding domain of SARS-CoV-1 S protein
(residues 306-527) with peptides spanning the receptor-binding motif (424-494) highlighted in
blue. Response frequency is based on experimental data available at the IEDB. Tested epitopes
that did not give positive responses are absent.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
| 55 | KYRYLRHGKLRPFERD | 439 | 454 | 1 | 1 | | | |
| | K439, G446, S461, D463 | 439 | 463 | 1 | 1 | 1 | 0 | 1 |
| | R441 | 441 | 441 | 2 | 2 | 1 | 0 | 1 |
| | Y442 | 442 | 442 | 1 | 1 | 2 | 0 | 1 |
| | Y442, A834 | 442 | 834 | 1 | 1 | 1 | 0 | 1 |
| | Y442, D757 | 442 | 757 | 1 | 1 | 1 | 0 | 1 |
| 56 | YLRHGKLRPFERDISNV | 442 | 458 | 4 | 2 | 2 | 2 | 0.5 |
| 57 | YLRHGKLRPFERDISNVP | 442 | 459 | 4 | 2 | 1 | 0 | 0.5 |
| 58 | LRHGKLRPFERDISNVP | 443 | 459 | 3 | 2 | 1 | 0 | 0.67 |
| | G446, P462, D463, Y475 | 446 | 475 | 1 | 1 | 1 | 0 | 1 |
| 59 | KLRPFERDI | 447 | 455 | 1 | 1 | 1 | 0 | 1 |
| 60 | KLRPFERDISNV | 447 | 458 | 1 | 1 | 1 | 0 | 1 |
| 61 | RPFERDISNV | 449 | 458 | 2 | 2 | 2 | 0 | 1 |
| 62 | RPFERDISNVPFS | 449 | 461 | 4 | 2 | 1 | 0 | 0.5 |
| 63 | RPFERDISNVPFSPDGK | 449 | 465 | 44 | 11 | 1 | 2 | 0.25 |
| | D454 | 454 | 454 | 1 | 1 | 1 | 0 | 1 |
| 64 | SNVPFSPDGKPCTPPAL | 456 | 472 | 44 | 11 | 1 | 2 | 0.25 |
| 65 | PFSPDGKPCTPP | 459 | 470 | 8 | 8 | 1 | 0 | 1 |
| 66 | FSPDGKPCTPPALNCYW | 460 | 476 | 1 | 1 | 1 | 0 | 1 |
| 67 | SPDGKPCTPPALNCYWP | 461 | 477 | 42 | 5 | 1 | 0 | 0.12 |
| | P462 | 462 | 462 | 1 | 1 | 1 | 0 | 1 |
| 68 | CTPPALNCYWPLNDYGF | 467 | 483 | 42 | 8 | 1 | 0 | 0.19 |
| 69 | ALNCYWPLNDYGFYTTTGIGYQPYRVVVLSFEL | 471 | 503 | 1 | 1 | 1 | 0 | 1 |
| 70 | ALNCYWPLNDYGFYTTTGIGYQPYRVVVLSFEL | 471 | 503 | 42 | 30 | 1 | 0 | 0.71 |
| 71 | ALNCYW | 471 | 476 | 4 | 1 | 1 | 0 | 0.25 |
| 72 | CYWPLNDYGFYTTTGIG | 474 | 490 | 42 | 7 | 1 | 0 | 0.17 |
| | N479 | 479 | 479 | 1 | 1 | 1 | 0 | 1 |
| | D480, Y484 | 480 | 484 | 1 | 1 | 1 | 0 | 1 |
| 73 | GFYTTTGIGYQPYRVVV | 482 | 498 | 42 | 8 | 1 | 0 | 0.19 |
| | Y484, T487 | 484 | 487 | 1 | 1 | 1 | 0 | 1 |

TABLE 3-continued

T cell epitope prediction for the receptor binding domain of SARS-CoV-1 S protein (residues 306-527) with peptides spanning the receptor-binding motif (424-494) highlighted in blue. Response frequency is based on experimental data available at the IEDB. Tested epitopes that did not give positive responses are absent.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
| 74 | TTGIGYQ | 486 | 492 | 1 | 1 | 1 | 0 | 1 |
| 75 | GYQPYRVVV LSFELLNAPA TV | 490 | 510 | 2 | 2 | 2 | 0 | 1 |
| 76 | GYQPYRVVV LSFELLNA | 490 | 506 | 44 | 9 | 2 | 1 | 0.2 |
| 77 | QPYRVVVLS F | 492 | 501 | 4 | 1 | 1 | 0 | 0.25 |
| 78 | VVLSFELLN APATVCGPK | 497 | 514 | 2 | 1 | 1 | 1 | 0.5 |
| 79 | VLSFELLNAP ATVCGPK | 498 | 514 | 42 | 8 | 1 | 0 | 0.19 |
| 80 | NAPATVCGP KLSTDLIK | 505 | 521 | 44 | 7 | 1 | 2 | 0.16 |
| 81 | CGPKLSTDLI KNQCVNF | 511 | 527 | 42 | 7 | 1 | 0 | 0.17 |

Sequence-Based B Cell Epitope Prediction Using the SEPPA 3.0 Server and the Atomic Coordinates Deposited as 5X58.Pdb.

TABLE 4

B cell epitope prediction for the receptor binding domain of SARS-CoV-2 S protein (residues 306-527) with peptides spanning the receptor-binding motif (424-494) highlighted in blue. The server SEPPA 3.0 was used with the default threshold of 0.064. Absent residues did not rank as epitope residues.

| resS eq | resName | score | location |
|---|---|---|---|
| 314 | VAL | 0.100 | surface |
| 315 | ARG | 0.081 | surface |
| 316 | PHE | 0.152 | surface |
| 317 | PRO | 0.101 | surface |
| 318 | ASN | 0.155 | surface |
| 331 | ALA | 0.115 | surface |
| 332 | THR | 0.158 | surface |
| 334 | PHE | 0.097 | surface |
| 335 | PRO | 0.110 | surface |
| 336 | SER | 0.083 | surface |
| 337 | VAL | 0.073 | surface |
| 338 | TYR | 0.077 | surface |
| 347 | ASN | 0.127 | surface |
| 378 | CYS | 0.179 | surface |
| 379 | PHE | 0.104 | surface |
| 380 | SER | 0.258 | surface |
| 381 | ASN | 0.072 | surface |
| 382 | VAL | 0.070 | surface |
| 391 | GLY | 0.073 | surface |
| 400 | GLY | 0.071 | surface |
| 401 | GLN | 0.068 | surface |
| 403 | GLY | 0.071 | surface |
| 405 | ILE | 0.085 | surface |
| 406 | ALA | 0.073 | surface |
| 407 | ASP | 0.079 | surface |
| 408 | TYR | 0.097 | surface |
| 409 | ASN | 0.080 | surface |
| 411 | LYS | 0.083 | surface |
| 424 | ASN | 0.066 | surface |
| 425 | THR | 0.072 | surface |
| 426 | ARG | 0.162 | surface |
| 427 | ASN | 0.078 | surface |
| 428 | ILE | 0.084 | surface |
| 429 | ASP | 0.083 | surface |
| 430 | ALA | 0.122 | surface |
| 431 | THR | 0.174 | surface |
| 432 | SER | 0.222 | surface |
| 433 | THR | 0.145 | surface |
| 434 | GLY | 0.202 | surface |
| 435 | ASN | 0.166 | surface |
| 436 | TYR | 0.220 | surface |
| 437 | ASN | 0.096 | surface |
| 438 | TYR | 0.101 | surface |
| 439 | LYS | 0.181 | surface |
| 440 | TYR | 0.081 | surface |
| 441 | ARG | 0.071 | surface |
| 442 | TYR | 0.093 | surface |
| 443 | LEU | 0.105 | surface |
| 444 | ARG | 0.087 | surface |
| 445 | HIS | 0.118 | surface |
| 446 | GLY | 0.073 | surface |
| 447 | LYS | 0.075 | surface |
| 448 | LEU | 0.066 | surface |
| 451 | PHE | 0.067 | surface |
| 454 | ASP | 0.083 | surface |
| 456 | SER | 0.114 | surface |
| 457 | ASN | 0.117 | surface |
| 458 | VAL | 0.116 | surface |
| 459 | PRO | 0.110 | surface |
| 460 | PHE | 0.130 | surface |
| 461 | SER | 0.171 | surface |
| 462 | PRO | 0.165 | surface |

TABLE 4-continued

B cell epitope prediction for the receptor binding domain of SARS-CoV-2 S protein (residues 306-527) with peptides spanning the receptor-binding motif (424-494) highlighted in blue. The server SEPPA 3.0 was used with the default threshold of 0.064. Absent residues did not rank as epitope residues.

| resSeq | resName | score | location |
|---|---|---|---|
| 463 | ASP | 0.173 | surface |
| 464 | GLY | 0.185 | surface |
| 465 | LYS | 0.174 | surface |
| 466 | PRO | 0.178 | surface |
| 467 | CYS | 0.161 | surface |
| 468 | THR | 0.195 | surface |
| 469 | PRO | 0.189 | surface |
| 470 | PRO | 0.225 | surface |
| 471 | ALA | 0.233 | surface |
| 472 | LEU | 0.242 | surface |
| 473 | ASN | 0.186 | surface |
| 474 | CYS | 0.193 | surface |
| 475 | TYR | 0.116 | surface |
| 476 | TRP | 0.106 | surface |
| 478 | LEU | 0.179 | surface |
| 479 | ASN | 0.172 | surface |
| 480 | ASP | 0.100 | surface |
| 481 | TYR | 0.144 | surface |
| 482 | GLY | 0.255 | surface |
| 483 | PHE | 0.138 | surface |
| 484 | TYR | 0.236 | surface |
| 485 | THR | 0.206 | surface |
| 486 | THR | 0.203 | surface |
| 487 | THR | 0.238 | surface |
| 488 | GLY | 0.210 | surface |
| 489 | ILE | 0.115 | surface |
| 490 | GLY | 0.105 | surface |
| 491 | TYR | 0.117 | surface |
| 492 | GLN | 0.096 | surface |
| 494 | TYR | 0.070 | surface |
| 501 | PHE | 0.072 | surface |
| 502 | GLU | 0.254 | surface |
| 503 | LEU | 0.261 | surface |
| 504 | LEU | 0.434 | surface |
| 505 | ASN | 0.324 | surface |
| 506 | ALA | 0.362 | surface |
| 507 | PRO | 0.441 | surface |
| 508 | ALA | 0.259 | surface |
| 509 | THR | 0.147 | surface |

Heptad Repeat 1 (902-952), Heptad Repeat 2 (1145-1184) and a Linker T Cell Epitopes Based on Data Available at the IEDB immunoBrowser.

TABLE 5

T cell epitope prediction for heptad repeat 1, linker and heptad repeat 2 of SARS-CoV-2 S protein (residues 902-1184). Response frequency is based on experimental data available at the IEDB. Tested epitopes that did not give positive responses are absent.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
| 82 | VLYENQKQIANQFNKAI | 897 | 913 | 43 | 20 | 1 | 1 | 0.47 |
| 83 | QIANQFNKAISQIQESL | 904 | 920 | 43 | 5 | 1 | 1 | 0.12 |
| 84 | KAISQIQESLTTTSTAL | 911 | 927 | 43 | 6 | 1 | 1 | 0.14 |
|  | Q917, E918, S919, T921, T922, S924, T925, A926, G928, K929, Q931, D932, V933, N935, Q936, A938, Q939, A940 | 917 | 940 | 1 | 1 | 1 | 0 | 1 |
| 85 | ESLTTTSTALGKLQDVV | 918 | 934 | 45 | 13 | 2 | 1 | 0.29 |
|  | T921, T922, T923, T925, A926, G928, K929, L930, D932, V933, N935, Q936, N937, Q939, A940, N942, T943, L944 | 921 | 944 | 1 | 1 | 1 | 0 | 1 |
| 86 | TALGKLQDVVNQNAQAL | 925 | 941 | 43 | 8 | 1 | 1 | 0.19 |

TABLE 5-continued

T cell epitope prediction for heptad repeat 1, linker and heptad repeat 2 of SARS-CoV-2 S protein (residues 902-1184). Response frequency is based on experimental data available at the IEDB. Tested epitopes that did not give positive responses are absent.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
| 87 | DVVNQNAQALNTLVKQL | 932 | 948 | 43 | 9 | 1 | 1 | 0.21 |
| 88 | QALNTLVKQLSSNFGAI | 939 | 955 | 46 | 17 | 2 | 2 | 0.37 |
| 89 | ALNTLVKQL | 940 | 948 | 52 | 3 | 3 | 4 | 0.06 |
| 90 | KQLSSNFGAISSVLNDI | 946 | 962 | 3 | 1 | 1 | 0 | 0.33 |
| 91 | AISSVLNDILSRLDKVEA | 954 | 971 | 1 | 1 | 1 | 0 | 1 |
| 92 | AISSVLNDILSRLDKVE | 954 | 970 | 42 | 11 | 1 | 0 | 0.26 |
| 93 | SVLNDILSR | 957 | 965 | 13 | 1 | 1 | 1 | 0.08 |
| 94 | VLNDILSRL | 958 | 966 | 166 | 12 | 6 | 3 | 0.07 |
| 95 | ILSRLDKVEAEVQIDRL | 962 | 978 | 3 | 1 | 1 | 0 | 0.33 |
| 96 | RLDKVEAEV | 965 | 973 | 41 | 5 | 2 | 2 | 0.12 |
| 97 | EAEVQIDRLITGRLQSL | 970 | 986 | 43 | 6 | 1 | 1 | 0.14 |
| 98 | AEVQIDRLIRLITGRLQS | 971 | 979 | 5 | 1 | 1 | 0 | 0.2 |
| 99 | LQTYVTQQ | 977 | 993 | 42 | 19 | 1 | 0 | 0.45 |
| 100 | LITGRLAAL | 978 | 986 | 2 | 1 | 1 | 1 | 0.5 |
| 101 | LITGRLQSL | 978 | 986 | 67 | 5 | 5 | 5 | 0.07 |
| 102 | RLQSLQTYV | 982 | 990 | 63 | 18 | 4 | 3 | 0.29 |
| 103 | SLQTYVTQQLIRAAEIR | 985 | 1001 | 42 | 16 | 1 | 0 | 0.38 |
| 104 | QLIRAAEIRASANLAATK | 993 | 1010 | 4 | 3 | 3 | 0 | 0.75 |
| 105 | QLIRAAEIRASANLAAT | 993 | 1009 | 42 | 8 | 1 | 0 | 0.19 |
| 106 | RASANLAATKMSECVLG | 1001 | 1017 | 42 | 7 | 1 | 0 | 0.17 |
| 107 | AATKMSECVLGQSKRVD | 1007 | 1023 | 42 | 13 | 1 | 0 | 0.31 |
| 108 | VLGQSKRVDFCGKGYHL | 1015 | 1031 | 3 | 1 | 1 | 0 | 0.33 |
| 109 | RVDFCGKGY | 1021 | 1029 | 36 | 2 | 1 | 0 | 0.06 |

TABLE 5-continued

T cell epitope prediction for heptad repeat 1, linker and heptad repeat 2 of SARS-CoV-2 S protein (residues 902-1184). Response frequency is based on experimental data available at the IEDB. Tested epitopes that did not give positive responses are absent.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
| 110 | DFCGKGYHLMSFPQAAP | 1023 | 1039 | 42 | 11 | 1 | 0 | 0.26 |
| 111 | LMSFPQAAPHGVVFLHV | 1031 | 1047 | 44 | 14 | 2 | 1 | 0.32 |
| 112 | APHGVVFLHV | 1038 | 1047 | 13 | 3 | 1 | 0 | 0.23 |
| 113 | PHGVVFLHVTYVPSQER | 1039 | 1055 | 42 | 11 | 1 | 0 | 0.26 |
| 114 | GVVFLHVTY | 1041 | 1049 | 2 | 1 | 1 | 0 | 0.5 |
| 115 | VVFLHVTYV | 1042 | 1050 | 37 | 4 | 4 | 2 | 0.11 |
| 116 | VTYVPSQERNFTTAPAI | 1047 | 1063 | 42 | 10 | 1 | 0 | 0.24 |
| 117 | ERNFTTAPAICHEGKAYF | 1054 | 1071 | 2 | 1 | 1 | 1 | 0.5 |
| 118 | RNFTTAPAICHEGKAYF | 1055 | 1071 | 42 | 7 | 1 | 0 | 0.17 |
| 119 | PAICHEGKAYFPREGVFVFNGTSWFITQRNFFS | 1061 | 1093 | 15 | 12 | 1 | 0 | 0.8 |
| 120 | HEGKAYFPREGV | 1065 | 1076 | 8 | 8 | 1 | 0 | 1 |
| 121 | AYFPREGVFVFNGTSWF | 1069 | 1085 | 42 | 2 | 1 | 0 | 0.05 |
| 122 | FVFNGTSWFITQRNFFS | 1077 | 1093 | 42 | 2 | 1 | 0 | 0.05 |
| 123 | GTSWFITQRNFFSPQ | 1081 | 1095 | 3 | 1 | 1 | 0 | 0.33 |
| 124 | SWFITQRNFFSPQII | 1083 | 1097 | 5 | 3 | 2 | 1 | 0.6 |
| 125 | NFFSPQIITTDNTFVSG | 1090 | 1106 | 3 | 1 | 1 | 0 | 0.33 |
| 126 | FFSPQIITTDNTFVSGN | 1091 | 1130 | 1 | 1 | 1 | 0 | 1 |
| 127 | CDVVIGIINNTVYDPLQPELDSFIITTDNTFV | 1096 | 1104 | 18 | 1 | 1 | 0 | 0.06 |
| 128 | ITTDNTFVSGNCDVVIG | 1097 | 1113 | 3 | 1 | 1 | 0 | 0.33 |
| 129 | FVSGNCDVVIGIINNTVY | 1103 | 1120 | 2 | 1 | 1 | 1 | 0.5 |

TABLE 5-continued

T cell epitope prediction for heptad repeat 1, linker and heptad repeat 2 of SARS-CoV-2 S protein (residues 902-1184). Response frequency is based on experimental data available at the IEDB. Tested epitopes that did not give positive responses are absent.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
| 130 | SGNCDVVIGIINNTVYD | 1105 | 1121 | 42 | 6 | 1 | 0 | 0.14 |
| 131 | VIGIINNTVYDPLQPELDSF | 1111 | 1130 | 2 | 2 | 2 | 0 | 1 |
| 132 | VIGIINNTVYDPLQPEL | 1111 | 1127 | 44 | 9 | 2 | 1 | 0.2 |
| 133 | TVYDPLQPELDSFKEEL | 1118 | 1134 | 43 | 2 | 1 | 1 | 0.05 |
| 134 | PELDSFKEELDKYFKNH | 1125 | 1141 | 4 | 1 | 1 | 1 | 0.25 |
| 135 | DSFKEELDKYFKNHTSPDVDLGDISGINASVV | 1128 | 1159 | 2 | 1 | 1 | 1 | 0.5 |
| 136 | DSFKEELDKY | 1128 | 1137 | 36 | 1 | 1 | 0 | 0.03 |
| 137 | EELDKYFKNHTSPDVDL | 1132 | 1148 | 4 | 1 | 1 | 1 | 0.25 |
| 138 | DKYFKNHTSPDVDLGD | 1135 | 1150 | 1 | 1 | 1 | 0 | 1 |
| 139 | KNHTSPDVDLGDISGIN | 1139 | 1155 | 42 | 4 | 1 | 0 | 0.1 |
| 140 | SPDVDLGDISGINAS | 1143 | 1157 | 65 | 2 | 2 | 2 | 0.03 |
| 141 | VDLGDISGI | 1146 | 1154 | 1 | 1 | 1 | 0 | 1 |
| 142 | DLGDISGINASVVNIQK | 1147 | 1163 | 43 | 6 | 1 | 1 | 0.14 |
| 143 | LGDISGINASVVNIQ | 1148 | 1162 | 17 | 1 | 1 | 0 | 0.06 |
| 144 | ISGINASVVNIQKEIDRLNE | 1151 | 1170 | 1 | 1 | 1 | 0 | 1 |
| 145 | ISGINASVVNIQKEIDRLNEVAKNLNESLIDLQELGKYEQYI | 1151 | 1192 | 1 | 1 | 1 | 0 | 1 |
| | N1155, A1156, S1157, V1159, N1160, Q1162, K1163, E1164, D1166, R1167, N1169, E1170, V1171, K1173, N1174, | 1155 | 1178 | 1 | 1 | 1 | 0 | 1 |

TABLE 5-continued

T cell epitope prediction for heptad repeat 1, linker and heptad repeat 2 of SARS-CoV-2 S protein (residues 902-1184). Response frequency is based on experimental data available at the IEDB. Tested epitopes that did not give positive responses are absent.

| SEQ ID NO | Sequence | Mapped Start Position | Mapped End Position | Subjects Tested | Subjects Responded | Assay Positive | Assay Negative | Response Freq. |
|---|---|---|---|---|---|---|---|---|
| | N1176, E1177, S1178 | | | | | | | |
| | Q1162, K1163, E1164, D1166, R1167, N1169, E1170, V1171, K1173, N1174, N1176, E1177, S1178, I1180, D1181, Q1183, E1184, L1185 | 1162 | 1185 | 1 | 1 | 1 | 0 | 1 |
| 146 | KEIDRLNEVAKNLNESL | 1163 | 1179 | 3 | 1 | 1 | 0 | 0.33 |
| 147 | EIDRLNEVAKNLNESLIDLQELGKYEQY | 1164 | 1191 | 1 | 1 | 1 | 0 | 1 |
| 148 | EIDRLNEVAKNLNESLIDLQELGKYEQY | 1164 | 1191 | 42 | 28 | 1 | 0 | 0.67 |
| 149 | RLNEVAKNL | 1167 | 1175 | 246 | 17 | 7 | 6 | 0.07 |
| 150 | EVAKNLNESLIDLQELG | 1170 | 1186 | 42 | 6 | 1 | 0 | 0.14 |

Structure-based B cell epitope prediction using the SEPPA 3.0 server and the atomic coordinates deposited as 5X58.pdb: For amino acids downstream of 1104, a sequence-based method (BepiPred 2.0) was used due to the lack of a solved structure encompassing that region.

TABLE 6

B cell epitope prediction for heptad repeat 1 (residues 902-952) and linker up to residue 1104 of SARS-CoV-2 S protein (remaining linker region and heptad repeat 2 are absent from the atomic coordinates of 5X58.pdb). The server SEPPA 3.0 was used with the default threshold of 0.064. Absent residues did not rank as epitope residues.

| resSeq | resName | score | location |
|---|---|---|---|
| 902 | GLN | 0.702 | surface |
| 903 | LYS | 0.515 | surface |
| 904 | GLN | 0.486 | surface |
| 906 | ALA | 0.430 | surface |
| 907 | ASN | 0.313 | surface |
| 908 | GLN | 0.302 | surface |
| 909 | PHE | 0.146 | surface |
| 910 | ASN | 0.136 | surface |
| 912 | ALA | 0.089 | surface |
| 913 | ILE | 0.122 | surface |
| 914 | SER | 0.104 | surface |
| 915 | GLN | 0.098 | surface |
| 916 | ILE | 0.068 | surface |
| 917 | GLN | 0.073 | surface |
| 918 | GLU | 0.099 | surface |
| 919 | SER | 0.109 | surface |
| 920 | LEU | 0.084 | surface |
| 921 | THR | 0.104 | surface |
| 941 | LEU | 0.097 | surface |
| 942 | ASN | 0.134 | surface |
| 943 | THR | 0.134 | surface |
| 944 | LEU | 0.107 | surface |
| 945 | VAL | 0.113 | surface |
| 947 | GLN | 0.174 | surface |
| 948 | LEU | 0.222 | surface |
| 949 | SER | 0.151 | surface |
| 950 | SER | 0.157 | surface |

TABLE 6-continued

B cell epitope prediction for heptad repeat 1 (residues 902-952) and linker up to residue 1104 of SARS-CoV-2 S protein (remaining linker region and heptad repeat 2 are absent from the atomic coordinates of 5X58.pdb). The server SEPPA 3.0 was used with the default threshold of 0.064. Absent residues did not rank as epitope residues.

| resSeq | resName | score | location |
|---|---|---|---|
| 952 | PHE | 0.236 | surface |
| 953 | GLY | 0.183 | surface |
| 954 | ALA | 0.172 | surface |
| 955 | ILE | 0.097 | surface |
| 956 | SER | 0.080 | surface |
| 957 | SER | 0.117 | surface |
| 958 | VAL | 0.089 | surface |
| 959 | LEU | 0.258 | surface |
| 960 | ASN | 0.115 | surface |
| 961 | ASP | 0.111 | surface |
| 962 | ILE | 0.115 | surface |
| 963 | LEU | 0.090 | surface |
| 964 | SER | 0.147 | surface |
| 965 | ARG | 0.144 | surface |
| 966 | LEU | 0.133 | surface |
| 967 | ASP | 0.135 | surface |
| 968 | LYS | 0.208 | surface |
| 969 | VAL | 0.177 | surface |
| 970 | GLU | 0.194 | surface |
| 972 | GLU | 0.236 | surface |
| 973 | VAL | 0.366 | surface |
| 974 | GLN | 0.237 | surface |
| 975 | ILE | 0.395 | surface |
| 976 | ASP | 0.401 | surface |
| 977 | ARG | 0.283 | surface |
| 978 | LEU | 0.270 | surface |
| 979 | ILE | 0.413 | surface |
| 980 | THR | 0.432 | surface |
| 981 | GLY | 0.360 | surface |
| 982 | ARG | 0.240 | surface |
| 983 | LEU | 0.288 | surface |
| 984 | GLN | 0.344 | surface |
| 985 | SER | 0.176 | surface |
| 987 | GLN | 0.098 | surface |
| 988 | THR | 0.070 | surface |
| 1028 | GLY | 0.149 | surface |
| 1029 | TYR | 0.255 | surface |
| 1050 | VAL | 0.513 | surface |
| 1051 | PRO | 0.432 | surface |
| 1052 | SER | 0.479 | surface |
| 1053 | GLN | 0.427 | surface |
| 1054 | GLU | 0.159 | surface |
| 1058 | THR | 0.073 | surface |
| 1059 | THR | 0.107 | surface |
| 1060 | ALA | 0.135 | surface |
| 1061 | PRO | 0.131 | surface |
| 1062 | ALA | 0.261 | surface |
| 1063 | ILE | 0.245 | surface |
| 1064 | CYS | 0.146 | surface |
| 1065 | HIS | 0.230 | surface |
| 1066 | GLU | 0.249 | surface |
| 1067 | GLY | 0.237 | surface |
| 1068 | LYS | 0.211 | surface |
| 1069 | ALA | 0.268 | surface |
| 1070 | TYR | 0.218 | surface |
| 1071 | PHE | 0.274 | surface |
| 1072 | PRO | 0.297 | surface |
| 1073 | ARG | 0.269 | surface |
| 1074 | GLU | 0.214 | surface |
| 1075 | GLY | 0.201 | surface |
| 1076 | VAL | 0.085 | surface |
| 1079 | PHE | 0.091 | surface |
| 1080 | ASN | 0.093 | surface |
| 1082 | THR | 0.090 | surface |
| 1083 | SER | 0.103 | surface |
| 1084 | TRP | 0.076 | surface |
| 1085 | PHE | 0.080 | surface |
| 1086 | ILE | 0.137 | surface |
| 1087 | THR | 0.170 | surface |
| 1088 | GLN | 0.147 | surface |
| 1089 | ARG | 0.168 | surface |
| 1090 | ASN | 0.253 | surface |
| 1091 | PHE | 0.398 | surface |
| 1092 | PHE | 0.136 | surface |
| 1093 | SER | 0.169 | surface |
| 1094 | PRO | 0.105 | surface |
| 1095 | GLN | 0.130 | surface |
| 1096 | ILE | 0.146 | surface |
| 1097 | ILE | 0.210 | surface |
| 1098 | THR | 0.233 | surface |
| 1099 | THR | 0.328 | surface |
| 1100 | ASP | 0.376 | surface |
| 1101 | ASN | 0.273 | surface |
| 1102 | THR | 0.321 | surface |
| 1103 | PHE | 0.322 | surface |
| 1104 | VAL | 0.320 | surface |

TABLE 7

B cell epitope prediction for amino acids 1105-1184 of SARS-CoV-2 S comprising the heptad repeat 2 and part of the upstream linker protein (based on the BepiPred algorithm, a server for sequence-based analysis (cbs.dtu.dk/services/BepiPred/). Residues immediately downstream or upstream of these were not identified as predicted epitopes (default threshold of 0.5).

| Position | AminoAcid | Exposed/Buried | EpitopeProbability |
|---|---|---|---|
| 1115 | I | B | 0.515 |
| 1116 | N | E | 0.522 |
| 1117 | N | E | 0.548 |
| 1118 | T | E | 0.567 |
| 1119 | V | E | 0.575 |
| 1120 | Y | B | 0.586 |
| 1121 | D | E | 0.589 |
| 1122 | P | E | 0.582 |
| 1123 | L | B | 0.569 |
| 1124 | Q | B | 0.557 |
| 1125 | P | E | 0.559 |
| 1126 | E | E | 0.541 |
| 1127 | L | E | 0.529 |
| 1128 | D | B | 0.521 |
| 1129 | S | E | 0.531 |
| 1130 | F | B | 0.515 |
| 1131 | K | E | 0.508 |
| 1132 | E | E | 0.517 |
| 1133 | E | E | 0.527 |
| 1134 | L | B | 0.519 |
| 1135 | D | E | 0.544 |
| 1136 | K | E | 0.555 |
| 1137 | Y | B | 0.569 |
| 1138 | F | B | 0.576 |
| 1139 | K | E | 0.587 |
| 1140 | N | E | 0.595 |
| 1141 | H | B | 0.601 |
| 1142 | T | E | 0.604 |
| 1143 | S | E | 0.617 |
| 1144 | P | E | 0.601 |
| 1145 | D | E | 0.606 |
| 1146 | V | B | 0.607 |
| 1147 | D | E | 0.590 |
| 1148 | L | B | 0.600 |
| 1149 | G | E | 0.593 |
| 1150 | D | E | 0.572 |
| 1151 | I | B | 0.574 |
| 1152 | S | E | 0.564 |
| 1153 | G | E | 0.560 |
| 1154 | I | B | 0.535 |
| 1155 | N | E | 0.516 |
| 1156 | A | B | 0.517 |
| 1177 | E | E | 0.501 |

TABLE 7-continued

B cell epitope prediction for amino acids 1105-1184 of SARS-CoV-2 S comprising the heptad repeat 2 and part of the upstream linker protein (based on the BepiPred algorithm, a server for sequence-based analysis (cbs.dtu.dk/services/BepiPred/). Residues immediately downstream or upstream of these were not identified as predicted epitopes (default threshold of 0.5).

| Position | AminoAcid | Exposed/Buried | EpitopeProbability |
|---|---|---|---|
| 1180 | I | B | 0.508 |
| 1181 | D | B | 0.510 |
| 1182 | L | B | 0.511 |
| 1183 | Q | E | 0.517 |
| 1184 | E | E | 0.509 |

Example 5

Biochemical and Cell Based Assays

Immune sera from vaccinated animals will be tested using ELISA. Here, the binding of polyclonal sera derived from animals is tested against VLP antigen immobilized on wells using serial dilutions. Binding of ELISA positive sera will be tested against full length SARS-COV-2 S protein. This will be done in two ways. Using ELISA, binding of anti-sera will be verified against the ectodomain of S protein recombinantly-expressed in 293HEK cells and purified to homogeneity using affinity chromatography. Further, binding will be characterized against full length S protein transiently-expressed in CHO or COS-7 cells using flow cytometry. These assays address whether anti-sera from immunized animals bind prefusion, glycosylated and intact S protein. Finally, neutralizing activity of antisera will be verified using live virus neutralization assays wherein SARS-CoV-2 virus together with antisera are used to infect Vero cells followed by detection of internalized virus using commercially available, anti-S protein antibody such as CR3022 (Pinto et. al., 2020).

Example 6

Animal Studies

Mouse studies will be conducted to screen the antigen panel and identify a lead and backup vaccine candidate. Up to 3 dose strengths will be tested for each vaccine construct. All vaccine formulations will be alum adjuvanted. Groups of mice (n=10, 6-8 week old female Balb/c) will be vaccinated with VLP vaccine constructs intramuscularly followed by a booster at 14 day intervals. Sera will be collected prior to immunization as well after 7 days after each immunization cycle. 10 days after the booster, animals will be challenged intranasal with SARS-CoV-2 virus. Animals will be monitored for signs of disease. Animals will be euthanized at the end of the study and lung tissue are harvested for pathology and immunohistochemical staining.

Non-Human Primate (NHP) Studies:

NHP studies will be carried out on the lead and backup vaccine candidates. The lead and/or the backup mixture of more than one of the vaccine constructs, including the RBD construct, will be also considered for the study. Up to 2 doses (high dose and low dose) for each vaccine construct will be tested. All vaccine formulations will be alum adjuvated. Adult rhesus macaques (n=4 for each group, M/F) will be vaccinated intramuscularly followed by a booster 14 days later. Blood samples will be collected before and after vaccination. Seven days following the booster, animals will be challenged with live SARS-CoV-2 virus intratracheally, intranasally, orally and ocularly. Clinical exams will be performed at regular intervals and BAL fluid are collected on periodic days. At the end of the study, animals will be euthanized and necropsy are performed.

Vaccine Safety Evaluation:

Safety evaluation of the lead vaccine candidate will be conducted in macaques. Groups of animals (n=5 M/F) will be immunized with high dose of the lead vaccine. A total of 3 intramuscular injections will be made (immunization plus two boosters). Safety evaluation include clinical observations as well as gross pathology on lung, heart, spleen, liver, kidney and brain.

Example 7

Process Development

Upstream and downstream processes for vaccine manufacture will be established according to standard industry norms in a cGMP grade BSL2 facility (Alvim et. al., 2019). Vero cell lines initially grown in tissue culture flasks at the research scale will be scaled-up in 5 L benchtop, stirred-tank bioreactors (Knowles et. al., 2013). Microcarriers will be used to enhance attachment of the adherent Vero cells. The culture will be maintained in a fed-batch mode with medium replenished on days 3 and 5 with fresh media to boost cellular productivity. VLPs secreted during the cell culture fermentation will be separated from cell mass by tangential-flow filtration (TFF) and downstream purification are undertaken. Concentration and buffer exchange will be conducted using additional TFF steps. This is followed by hydrophobic interaction chromatography and an ion-exchange step to purify the VLP fraction. Purified VLPs will be formulated and sterile filtered as described below (Aravelo et. al., 2016).

Process robustness and reproducibility will be established by running at least 3 lots of VLP production for both USP and DSP steps. Analytical method development includes tests for purity and potency in addition to validation of physical characteristics (appearance, particle size, pH) and identity (ELISA or Western Blot). Purity assessment will be done by SDS-PAGE densitometry as well as total protein content measured by BCA assay. Potency assessment will be conducted by use of validated ELISA methods using antibodies specific to VLP antigens. Impurity testing includes host protein and DNA quantitation.

Vaccines will be tested using a panel of buffers and excipients to identify a stable formulation. Histidine Tris and PBS buffers will be mixed with excipients such as Polysorbate 80, amino acids, sucrose and trehalose. In addition, vaccines will be adsorbed on alum adjuvant for increased stability (as well as enhanced immunogenicity). Formulated vaccine will be sterile filtered and filled in 2 mL single dose glass vials. Multi dose vials will be tested once vaccine PoC was established. An initial goal is to establish a formulation compatible with a vaccine vial monitor (VMM) 14 label. To do so, formal stability studies will be conducted as described below.

Accelerated stability studies will be conducted at 4° C., 25° C., 37° C. and 40° C. followed by potency assessment allowed selection of the lead formulation from the panel above. For formal stability studies, a minimum of three lots of lead vaccine formulation will be placed on stability study for 3 to 6 months. Stability-indicating assays including pH, physical appearance, potency and sterility will be conducted.

It is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

REFERENCES

Each of the references cited herein is expressly incorporated herein by reference in its entirety.

Alsaadi, E. A. J., "Membrane binding proteins of coronaviruses" FutureVirol 14:4 (275-286) 2019.

Alvim, R. G. F., "Zika virus-like particles (VLPs): Stable cell lines and continuous perfusion processes as a new potential vaccine manufacturing platform", Vaccine 37 (6970-6977) 2019.

Ammerman, N. C., "Growth and Maintenance of Vero Cell Lines", Curr Protoc Microbiol. November 2008 Andersen, K. G., "The proximal origin of SARS-CoV-2", Nature Medicine, 26 (450-455) April 2020 Arevalo, M. T., "Expression and Purification of Virus-like Particles for Vaccination", Journal of Visualized Experiments June 2016|112|e54041|.

Bestle, D., "TMPRSS2 and furin are both essential for proteolytic activation and spread of SARS-CoV-2 in human airway epithelial cells and provide promising drug targets", bioRxiv preprint doi: doi.org/10.1101/2020.04.15.042085.

Bianchi, M. "SARS-CoV-2 Envelope and Membrane proteins: differences from closely related proteins linked to cross-species transmission?" doi:10.20944/preprints202004.0089.v1 Apr. 2020.

Blanco-Melo, D., "Imbalanced Host Response to SARS-CoV-2 Drives Development of COVID-19", Cell 181 (1-10) May 2020.

Burton, D. R. "Rational Vaccine Design in the Time of COVID-19", Cell Host & Microbe 27, May 13, 2020 Cao, X., "COVID-19: immunopathology and its implications for therapy", Nature Reviews Immunology, 20 (260) May 2020.

Ceraolo, C., "Genomic variance of the 2019-nCoV coronavirus", J Med Virol. 92 (522-528) 2020 Chakraborti, S. "Symptomatic SARS-CoV-2 infections display specific IgG Fc structures", medRxiv preprint doi: doi.org/10.1101/2020.05.15.20103341.

Chen, W. H., "Yeast-Expressed SARS-CoV Recombinant Receptor-Binding Domain (RBD219-N1) Formulated with Alum Induces Protective Immunity and Reduces Immune Enhancement", bioRxiv preprint doi: doi.org/10.1101/2020.05.15.098079.

Coleman, C. M., "Purified coronavirus spike protein nanoparticles induce coronavirus neutralizing antibodies in mice", Vaccine 32 (3169-3174) 2014.

Doremalen, N. V., "ChAdOx1 nCoV-19 vaccination prevents SARS-CoV-2 pneumonia in rhesus macaques", doi.org/10.1101/2020.05.13.093195.

Ejemel, M., "IgA MAb blocks SARS-CoV-2 Spike-ACE2 interaction providing mucosal immunity", bioRxiv preprint doi: doi.org/10.1101/2020.05.15.096719.

Elshabrawy, H. A., "Human Monoclonal Antibodies against Highly Conserved HR1 and HR2 Domains of the SARS-CoV Spike Protein Are More Broadly Neutralizing", PLOS ONE 7:11, e50366, November 2012 Feng Z., "The novel severe acute respiratory syndrome coronavirus 2 (SARS-CoV-2) directly decimates human spleens and lymph nodes" medRxiv doi: 10.1101/2020.03.27.20045427 2020.

Fleming, A. B., "Current studies of convalescent plasma therapy for COVID-19 may underestimate risk of antibody-T dependent enhancement", J Clin Virol 127, 104388 (2020).

Fox, S. E., "Pulmonary and Cardiac Pathology in Covid-19: The First Autopsy Series from New Orleans", medRxiv preprint doi: doi.org/10.1101/2020.04.06.20050575.

Gao, Q., "Rapid development of an inactivated vaccine for SARS-CoV-2", bioRxiv preprint doi: doi.org/10.1101/2020.04.17.046375.

Graham, B. S., "Rapid COVID-19 vaccine development", Science 10, 1126 (2020).

Hakkanson-McReynolds, S., "Solution Structure of the Severe Acute Respiratory Syndrome-Coronavirus Heptad Repeat 2 Domain in the Prefusion State" J Biol Chem 281:17 (2006).

Herold, T., "Level of IL-6 predicts respiratory failure in hospitalized symptomatic COVID-19 patients" medRxiv preprint doi: doi.org/10.1101/2020.04.01.20047381 2020.

Hotez, P. J., "COVID-19 vaccine design: the Janus face of immune enhancement", Nature Reviews Immunology.

Huang, C., "Clinical features of patients infected with 2019 novel coronavirus in Wuhan, China" Lancet 395 (497-506) 2020.

Iwasaki, A., "The potential danger of suboptimal antibody responses in COVID-19", Nature Reviews Immunology.

Jaume, M., "Anti-Severe Acute Respiratory Syndrome Coronavirus Spike Antibodies Trigger Infection of Human Immune Cells via a pH- and Cysteine Protease-Independent FcgR Pathway" J Virol, (10582-10597) 2011.

Jespersen, et al. BepiPred-2.0: improving sequence-based B-cell epitope prediction using conformational epitopes. Nucleic Acids Res. 45, W24-W29, 2017.

Jiang, S., "Don't rush to deploy COVID-19 vaccines and drugs", Nature 579 (321) 2020.

Kamikubo, Y., "Paradoxical dynamics of SARS-CoV-2 by herd immunity and antibody-dependent enhancement" Cambridge Open Engage doi:10.33774/coe-2020-fsnb3 2020.

Katzelnick, L. C., "Antibody-dependent enhancement of severe dengue disease in humans", Science 358 (929-932) 2017.

Knowles, S., "Linear scalability of virus production in the integrity@ iCELLis® single-use fixed-bed bioreactors from bench to industrial scale", BMC Proceedings 7:6 (60) 2013.

Liang, M. F., "SARS Patients-derived Human Recombinant Antibodies to S and M Proteins Efficiently Neutralize SARS-Coronavirus Infectivity" Biomed & Env Sci 18, (363-374) 2005.

Lip, K. M., "Monoclonal Antibodies Targeting the HR2 Domain and the Region Immediately Upstream of the HR2 of the S Protein Neutralize In Vitro Infection of Severe Acute Respiratory Syndrome Coronavirus", J Virol (941-950) 2006.

Liu, L., "Anti-spike IgG causes severe acute lung injury by skewing macrophage responses during acute SARS-CoV infection", JCI Insight. 4:4 (e123158) 2019.

Liu, Y., "2019-novel coronavirus (2019-nCoV) infections trigger an exaggerated cytokine response aggravating lung injury" ChinaXiv.

Martini, A., "A Universal Plug-and-Display Vaccine Carrier Based on HBsAg VLP to Maximize Effective Antibody Response", Frontiers in Immunology 10 (2931) 2019.

Monteil, V., "Inhibition of SARS-CoV-2 Infections in Engineered Human Tissues Using Clinical-Grade Soluble Human ACE2", Cell 181 (1-9) 2020.

Naskalsak, A. "Membrane Protein of Human Coronavirus NL63 Is Responsible for Interaction with the Adhesion Receptor" J Virol 93:19 (1-14) 2019.

Pinto, D., "Cross-neutralization of SARS-CoV-2 by a human monoclonal SARS-CoV antibody", Nature doi.org/10.1038/s41586-020-2349-y, April 2020.

Ramasamy, V. "A tetravalent virus-like particle vaccine designed to display domain III of dengue envelope proteins induces multi-serotype neutralizing antibodies in mice and macaques which confer protection against antibody dependent enhancement in AG129 mice", PLOS Neglected Tropical Diseases|doi.org/10.1371/journal.pntd.0006191 2018.

Richardson, S., "Presenting Characteristics, Comorbidities, and Outcomes Among 5700 Patients Hospitalized With COVID-19 in the New York City Area", JAMA doi: 10.1001/jama.2020.6775, Ricke, D. O., "Medical Countermeasures Analysis of 2019-nCoV and Vaccine Risks for Antibody-dependent Enhancement (ADE)".

Robianni, D. F., "Convergent Antibody Responses to SARS-CoV-2 Infection in Convalescent Individuals", bioRxiv preprint doi: doi.org/10.1101/2020.05.13.092619.

Sardu, C., "Is COVID-19 an endothelial disease? Clinical and basic evidence", doi:10.20944/preprints202004.0204.v1.

Shang, J., "Cell entry mechanisms of SARS-CoV-2", Proc Natl Acad Sci (USA) 117: 21 (11727-11734) 2020 Tan, L., "Lymphopenia predicts disease severity of COVID-19: a descriptive and predictive study", Signal Transduction and Targeted Therapy 5 (33) 2020.

Tetro, J., "Is COVID-19 receiving ADE from other coronaviruses?", Microbes and Infection 22:72 (e73) 20.

Tian, S., "Pathological study of the 2019 novel coronavirus disease (COVID-19) through postmortem core biopsies", Modern Pathology doi.org/10.1038/s41379-020-0536-x.

Tseng, C. T., "Immunization with SARS Coronavirus Vaccines Leads to Pulmonary Immunopathology on Challenge with the SARS Virus", PLoS ONE 7: 4 (e35421) 2012.

Varga, Z., "Endothelial cell infection and endotheliitis in COVID-19" Lancet doi.org/10.1016/S0140-6736(20) 30937-5.

Vita et. al., The immune epitope database (IEDB) 3.0. Nucleic Acids Res. 43, D405-D412, 2014.

Walls, A. C., "Structure, Function, and Antigenicity of the SARS-CoV-2 Spike Glycoprotein" Cell 180 (281-292) 2020.

Wang, Q., "Immunodominant SARS Coronavirus Epitopes in Humans Elicited both Enhancing and Neutralizing Effects on Infection in Non-human Primates" ACS Infect. Dis. 2 (361-376) 2016.

Wang, D., "Clinical Characteristics of 138 Hospitalized Patients With 2019 Novel Coronavirus-Infected Pneumonia in Wuhan, China" JAMA, doi:10.1001/jama.2020.1585 2020.

Wang, C., "A human monoclonal antibody blocking SARS-CoV-2 infection" NATURE COMMUNICATIONS doi.org/10.1038/s41467-020-16256-y, 2020 bioRxiv preprint doi: doi.org/10.1101/2020.05.15.096511.

Wec, A. Z., "Broad sarbecovirus neutralizing antibodies define a key site of vulnerability on the SARS-CoV-2 spike protein" bioRxiv preprint doi: doi.org/10.1101/2020.05.20.103325.

Wrapp, D., "Cryo-EM structure of the 2019-nCoV spike in the prefusion conformation" Science 367 (1260-1263) 2020.

Wu, F., "Neutralizing antibody responses to SARS-CoV-2 in a COVID-19 recovered patient cohort and their implications", medRxiv preprint doi: doi.org/10.1101/2020.03.30.20047365.

Wu, F., "A new coronavirus associated with human respiratory disease in China" Nature 579 (12) 2020 Wu, C. Y., "Mammalian Expression of Virus-Like Particles for Advanced Mimicry of Authentic Influenza Virus" PLoS ONE 5:3 (e9784) 2010.

Xia, S., "Inhibition of SARS-CoV-2 (previously 2019-nCoV) infection by a highly potent pan-coronavirus fusion inhibitor targeting its spike protein that harbors a high capacity to mediate membrane fusion" Cell Research 30 (343-355) 2020.

Xu, Z., "Pathological findings of COVID-19 associated with acute respiratory distress syndrome" Lancet Respir Med 8 (420-422) 2020.

Yang, Z. Y., "Evasion of antibody neutralization in emerging severe acute respiratory syndrome coronaviruses" Proc Natl Acad Sci (USA) 102:3 (797-801) 2005.

Yip, M. S., "Antibody-dependent infection of human macrophages by severe acute respiratory syndrome coronavirus", Virology Journal 11 (82) 2014.

Yuan, M., "A highly conserved cryptic epitope in the receptor binding domains of SARS-CoV-2 and SARS-CoV" Science 368 (630-633) 2020.

Zhao, J., et al "Antibody responses to SARS-CoV-2 in patients of novel coronavirus disease 2019" doi.org/10.1101/2020.03.02.20030189, 2020.

Zhou, et al. SEPPA 3.0—enhanced spatial epitope prediction enabling glycoprotein antigens. Nucleic Acids Res. 47, W388-W394, 2019.

I claim:

1. An immunogenic composition comprising a virus-like particle (VLP) and at least one antigenic polypeptide displayed on the surface of the VLP, wherein the at least one antigenic polypeptide is derived from one or more domains of a coronavirus spike(S) protein, a coronavirus membrane (M) protein or combinations thereof, wherein the VLP has at least 95% sequence identity to SEQ ID NO: 167.

2. A method of inducing an immune response to at least one coronavirus antigen in a subject in need thereof, comprising administering an effective amount of the immunogenic composition of claim 1 to the subject.

3. The method of claim 2, further comprising the steps of:
   allowing a suitable period of time to elapse; and
   administering at least one additional dose of the immunogenic composition of claim 1 to the subject.

* * * * *